(12) United States Patent
Lin et al.

(10) Patent No.: US 8,221,905 B2
(45) Date of Patent: Jul. 17, 2012

(54) CARBAZOLE-CONTAINING MATERIALS IN PHOSPHORESCENT LIGHT EMITTING DIODES

(75) Inventors: Chun Lin, Langhorne, PA (US); Alexey Borisovich Dyatkin, Ambler, PA (US); Zeinab Elshenawy, Holland, PA (US)

(73) Assignee: Universal Display Corporation, Ewing, NJ (US)

( * ) Notice: Subject to any disclaimer, the term of this patent is extended or adjusted under 35 U.S.C. 154(b) by 776 days.

(21) Appl. No.: 12/275,894

(22) Filed: Nov. 21, 2008

(65) Prior Publication Data

US 2009/0134784 A1 May 28, 2009

Related U.S. Application Data

(63) Continuation-in-part of application No. 12/209,928, filed on Sep. 12, 2008, now abandoned.

(60) Provisional application No. 61/017,480, filed on Dec. 28, 2007, provisional application No. 61/017,391, filed on Dec. 28, 2007.

(51) Int. Cl.
H01L 51/54 (2006.01)

(52) U.S. Cl. ........ 428/690; 428/917; 313/504; 313/505; 313/506; 257/40; 257/E51.05; 548/440; 544/234; 564/426; 564/434

(58) Field of Classification Search ............... 428/690, 428/917; 313/504, 505, 506; 257/40, E51.05; 564/426, 434; 548/440; 544/234
See application file for complete search history.

(56) References Cited

U.S. PATENT DOCUMENTS

| | | | |
|---|---|---|---|
| 4,769,292 | A | 9/1988 | Tang et al. |
| 5,061,569 | A | 10/1991 | VanSlyke et al. |
| 5,247,190 | A | 9/1993 | Friend et al. |
| 5,703,436 | A | 12/1997 | Forrest et al. |
| 5,707,745 | A | 1/1998 | Forrest et al. |
| 5,834,893 | A | 11/1998 | Bulovic et al. |
| 5,884,363 | A | 3/1999 | Tofts |
| 6,013,982 | A | 1/2000 | Thompson et al. |
| 6,087,196 | A | 7/2000 | Sturm et al. |
| 6,091,195 | A | 7/2000 | Forrest et al. |
| 6,097,147 | A | 8/2000 | Baldo et al. |
| 6,294,398 | B1 | 9/2001 | Kim et al. |
| 6,303,238 | B1 | 10/2001 | Thompson et al. |
| 6,337,102 | B1 | 1/2002 | Forrest et al. |
| 6,468,819 | B1 | 10/2002 | Kim et al. |
| 6,687,266 | B1 | 2/2004 | Ma et al. |
| 6,835,469 | B2 | 12/2004 | Kwong et al. |
| 7,087,321 | B2 | 8/2006 | Kwong et al. |
| 7,279,704 | B2 | 10/2007 | Walters et al. |
| 7,329,722 | B2 | 2/2008 | Vaitkeviciene et al. |
| 7,431,968 | B1 | 10/2008 | Shtein et al. |
| 2001/0046612 | A1 | 11/2001 | Lee et al. |
| 2002/0034656 | A1 | 3/2002 | Thompson et al. |
| 2002/0045061 | A1 | 4/2002 | Hosokawa |
| 2002/0134984 | A1 | 9/2002 | Igarashi |
| 2003/0175553 | A1 | 9/2003 | Thompson et al. |
| 2003/0230980 | A1 | 12/2003 | Forrest et al. |
| 2004/0174116 | A1 | 9/2004 | Lu et al. |
| 2005/0025993 | A1 | 2/2005 | Thompson et al. |
| 2005/0260441 | A1 | 11/2005 | Thompson et al. |
| 2005/0260449 | A1 | 11/2005 | Walters et al. |
| 2006/0008670 | A1 | 1/2006 | Lin et al. |
| 2006/0202194 | A1 | 9/2006 | Jeong et al. |
| 2006/0220011 | A1 | 10/2006 | Kitamura |
| 2006/0251923 | A1 | 11/2006 | Lin et al. |
| 2006/0280965 | A1 | 12/2006 | Kwong et al. |
| 2007/0015004 | A1 | 1/2007 | Nariyuki |
| 2007/0190359 | A1 | 8/2007 | Knowles et al. |

FOREIGN PATENT DOCUMENTS

| | | |
|---|---|---|
| EP | 0650955 | 5/1995 |
| JP | 62283341 | 12/1987 |
| JP | 200511610 | 1/2005 |
| JP | 2007123392 | 5/2007 |
| JP | 2007254297 | 10/2007 |
| JP | 2008074939 | 4/2008 |
| JP | 2008078362 | 4/2008 |
| WO | WO 0139234 | 5/2001 |
| WO | WO 0202714 | 1/2002 |
| WO | WO 03040257 | 5/2003 |
| WO | WO 03060956 | 7/2003 |
| WO | WO 2004093207 | 10/2004 |
| WO | WO 2004107822 | 12/2004 |
| WO | WO 2005014551 | 2/2005 |
| WO | WO 2005030900 | 4/2005 |
| WO | WO 2005089025 | 9/2005 |
| WO | WO 2005123873 | 12/2005 |
| WO | WO 2006009024 | 1/2006 |
| WO | WO 2006056418 | 6/2006 |
| WO | WO 2006082742 | 8/2006 |
| WO | WO 2006098120 | 9/2006 |
| WO | WO 2006103874 | 10/2006 |
| WO | WO 2006114966 | 11/2006 |
| WO | WO 2006132173 | 12/2006 |
| WO | WO 2007004380 | 1/2007 |
| WO | WO 2007029798 | 3/2007 |
| WO | WO 2007063754 | 6/2007 |
| WO | WO 2007063796 | 6/2007 |

OTHER PUBLICATIONS

Grazulevicius et al., Synthesis and Properties of Poly(3,9-carbazole) and low-molar mass glass-forming carbazole compounds, 2002, Polymer, vol. 43, pp. 2603-2603.*

(Continued)

Primary Examiner — Jennifer Chriss
Assistant Examiner — Gregory Clark
(74) Attorney, Agent, or Firm — Kilpatrick Townsend & Stockton LLP

(57) ABSTRACT

Carbazole-containing compounds are provided. In particular, the compounds are oligocarbazole-containing compounds having an unsymmetrical structure. The compounds may be useful in organic light emitting devices, in particular as hosts in the emissive layer of such devices.

37 Claims, 3 Drawing Sheets

OTHER PUBLICATIONS

Grazulevicius et al., Well defined Carbazol-3,9-diyl based oligomers with diphenylamino end-cap as novel amorphous molecular materials for optoelectronics, 2005, Journal of Photochemistry and Photobiology A: Chemistry, vol. 174, pp. 125-129.*

The International Search Report and Written Opinion corresponding to the PCT/US2008/087557 application, dated Jun. 26, 2009.

Baldo et al., "Highly Efficient Phosphorescent Emission from Organic Electroluminescent Devices," Nature, vol. 395, 151-154, 1998; ("Baldo-I").

Baldo et al., "Very high-efficiency green organic light-emitting devices based on electrophosphorescence," Appl. Phys. Lett., vol. 75, No. 3, 4-6 (1999) ("Baldo-II").

Xu et al. "Facile synthesis of novel monodisperse linear 3,9-linked oligocarbazoles," Tetrahedron Letters 46 (2005) p. 6883-6886.

Tsai et al. "3-(9-Carbazolyl)carbazoles and 3,6-Di(9-carbazolyl)carbazoles as effective host materials for efficient blue organic electrophosphorescence" Adv. Mater. 2007, 19, 862-866.

Kondakov et al., "Free-radical pathways in operational degradation of OLEDs" Journal of the Society for Information Display (2008), 16(1), 37-46.

U.S. Appl. No. 61/017,480, filed Dec. 28, 2007.
U.S. Appl. No. 61/017,506, filed Dec. 28, 2007.
U.S. Appl. No. 61/013,391, filed Dec. 28, 2007.
U.S. Appl. No. 11/443,586, filed May 31, 2006.
U.S. Appl. No. 12/209,928, filed Sep. 12, 2008.

Kuwabara, Yoshiyuki et al., "Thermally Stable Multilayered Organic Electroluminescent Devices Using Novel Starburst Molecules, 4,4',4"-Tri(N-carbazolyl)triphenylamine (TCTA) and 4,4',4"-Tris(3-methylphenylphenyl-amino)triphenylamine (m-MTDATA), as Hole-Transport Materials," Adv. Mater., 6(9):677-679 (1994).

Paulose, Betty Marie Jennifer S. et al., "First Examples of Alkenyl Pyridines as Organic Ligands for Phosphorescent Iridium Complexes," Adv. Mater., 16(22):2003-2007 (2004).

Tung, Yung-Liang et al., "Organic Light-Emitting Diodes Based on Charge-Neutral Ru$^{II}$ PHosphorescent Emitters," Adv. Mater., 17(8):1059-1064 (2005).

Huang, Jinsong et al., "Highly Efficient Red-Emission Polymer Phosphorescent Light-Emitting Diodes Based on Two Novel Tris(1-phenylisoquinolinato-C2,N)iridium(III) Derivatives," Adv. Mater., 19:739-743 (2007).

Wong, Wai-Yeung, "Multifunctional Iridium Complexes Based on Carbazole Modules as Highly Efficient Electrophosphors," Angew. Chem. Int. Ed., 45:7800-7803 (2006).

Tang, C.W. and VanSlyke, S.A., "Organic Electroluminescent Diodes," Appl. Phys. Lett., 51(12):913-915 (1987).

Adachi, Chihaya et al., "Organic Electroluminescent Device Having a Hole Conductor as an Emitting Layer," Appl. Phys. Lett., 55(15):1489-1491 (1989).

Ma, Yuguang et al., "Triplet Luminescent Dinuclear-Gold(/) Complex-Based Light-Emitting Diodes with Low Turn-On voltage," Appl. Phys. Lett., 74(10):1361-1363 (1999).

Gao, Zhiqiang et al., "Bright-Blue Electroluminescence From a Silyl-Substituted ter-(phenylene-vinylene) derivative," Appl. Phys. Lett., 74(6):865-867 (1999).

Baldo, M.A. et al., "Very High-Efficiency Green Organic Light-Emitting Devices Based on Electrophosphorescence," Appl. Phys. Lett., 75(1):4-6 (1999).

Lee, Chang-Lyoul et al., "Polymer Phosphorescent Light-Emitting Devices Doped with Tris(2-phenylpyridine) Iridium as a Triplet Emitter," Appl. Phys. Lett., 77(15):2280-2282 (2000).

Hung, L.S. et al., "Anode Modification in Organic Light-Emitting Diodes by Low-Frequency Plasma Polymerization of $CHF_3$," Appl. Phys. Lett., 78(5):673-675 (2001).

Ikai, Masamichi and Tokito, Shizuo, "Highly Efficient Phosphorescence From Organic Light-Emitting Devices with an Exciton-Block Layer," Appl. Phys. Lett., 79(2):156-158 (2001).

Wang, Y. et al., "Highly Efficient Electroluminescent Materials Based on Fluorinated Organometallic Iridium Compounds," Appl. Phys. Lett., 79(4):449-451 (2001).

Kwong, Raymond C. et al., "High Operational Stability of Electrophosphorescent Devices," Appl. Phys. Lett., 81(1):162-164 (2002).

Holmes, R.J. et al., "Blue Organic Electrophosphorescence Using Exothermic Host-Guest Energy Transfer," Appl. Phys. Lett., 82(15):2422-2424 (2003).

Sotoyama, Wataru et al., "Efficient Organic Light-Emitting Diodes with Phosphorescent Platinum Complexes Containing N^C^N-Co-ordinating Tridentate Ligand," Appl. Phys. Lett., 86:153505-1-153505-3 (2005).

Okumoto, Kenji et al., "Green Fluorescent Organic Light-Emitting Device with External Quantum Efficiency of Nearly 10%," Appl. Phys. Lett., 89:063504-1-063504-3 (2006).

Kanno, Hiroshi et al., "Highly Efficient and Stable Red Phosphorescent Organic Light-Emitting Device Using bis[2-(2-benzothiazoyl)phenolato]zinc(II) as host material," Appl. Phys. Lett., 90:123509-1-123509-3 (2007).

Aonuma, Masaki et al., "Material Design of Hole Transport Materials Capable of Thick-Film Formation in Organic Light Emitting Diodes," Appl. Phys. Lett., 90:183503-1-183503-3 (2007).

Sun, Yiru and Forrest, Stephen R., "High-Efficiency White Organic Light Emitting Devices with Three Separate Phosphorescent Emission Layers," Appl. Phys. Lett., 91:263503-1-263503-3 (2007).

Adachi, Chihaya et al., "High-Efficiency Red Electrophosphorescence Devices," Appl. Phys. Lett., 78(11):1622-1624 (2001).

Wong, Keith Man-Chung et al., A Novel Class of Phosphorescent Gold(III) Alkynyl-Based Organic Light-Emitting Devices with Tunable Colour, Chem. Commun., 2906-2908 (2005).

Hamada, Yuji et al., "High Luminance in Organic Electroluminescent Devices with Bis(10-hydroxybenzo[h]quinolinato)beryllium as an Emitter," Chem. Lett., 905-906 (1993).

Nishida, Jun-ichi et al., "Preparation, Characterization, and Electroluminescence Characteristics of α-Diimine-type Platinum(II) Complexes with Perfluorinated Phenyl Groups as Ligands," Chem. Lett., 34(4):592-593 (2005).

Mi, Bao-Xiu et al., "Thermally Stable Hole-Transporting Material for Organic Light-Emitting Diode: an Isoindole Derivative," Chem. Mater., 15(16):3148-3151 (2003).

Huang, Wei-Sheng et al., "Highly Phosphorescent Bis-Cyclometalated Iridium Complexes Containing Benzoimidazole-Based Ligands," Chem. Mater., 16(12):2480-2488 (2004).

Niu, Yu-Hua et al., "Highly Efficient Electrophosphorescent Devices with Saturated Red Emission from a Neutral Osmium Complex," Chem. Mater., 17(13):3532-3536 (2005).

Lo, Shih-Chun et al., "Blue Phosphorescence from Iridium(III) Complexes at Room Temperature," Chem. Mater., 18(21):5119-5129 (2006).

Takizawa, Shin-ya et al., "Phosphorescent Iridium Complexes Based on 2-Phenylimidazo[1,2-α]pyridine Ligands: Tuning of Emission Color toward the Blue Region and Application to Polymer Light-Emitting Devices," Inorg. Chem., 46(10):4308-4319 (2007).

Lamansky, Sergey et al., "Synthesis and Characterization of Phosphorescent Cyclometalated Iridium Complexes," Inorg. Chem., 40(7):1704-1711 (2001).

Ranjan, Sudhir et al., "Realizing Green Phosphorescent Light-Emitting Materials from Rhenium(I) Pyrazolato Diimine Complexes," Inorg. Chem., 42(4):1248-1255 (2003).

Noda, Tetsuya and Shirota,Yasuhiko, "5,5'-Bis(dimesitylboryl)-2,2'-bithiophene and 5,5"-Bis(dimesitylboryl)-2,2':5',2"-terthiophene as a Novel Family of Electron-Transporting Amorphous Molecular Materials," J. Am. Chem. Soc., 120 (37):9714-9715 (1998).

Sakamoto,Youichi et al., "Synthesis, Characterization, and Electron-Transport Property of Perfluorinated Phenylene Dendrimers," J. Am. Chem. Soc., 122(8):1832-1833 (2000).

Adachi, Chihaya et al., "Nearly 100% Internal Phosphorescence Efficiency in an Organic Light Emitting Device," J. Appl. Phys., 90(10):5048-5051 (2001).

Shirota, Yasuhiko et al., "Starburst Molecules Based on π-Electron Systems as Materials for Organic Electroluminescent Devices," Journal of Luminescence, 72-74:985-991 (1997).

Inada, Hiroshi and Shirota, Yasuhiko, "1,3,5-Tris[4-(diphenylamino)phenyl]benzene and its Methylsubstituted Derivatives as a Novel Class of Amorphous Molecular Materials," *J. Mater. Chem.*, 3(3):319-320 (1993).

Kido, Junji et al., 1,2,4-Triazole Derivative as an Electron Transport Layer in Organic Electroluminescent Devices, *Jpn. J. Appl. Phys.*, 32:L917-L920 (1993).

Van Slyke, S. A. et al., "Organic Electroluminescent Devices with Improved Stability," *Appl. Phys. Lett.*, 69(15):2160-2162 (1996).

Baldo, M. A. et al., "Highly Efficient Phosphorescent Emission From Organic Electroluminescent Devices," *Nature*, 395:151-154 (1998).

Guo, Tzung-Fang et al., "Highly Efficient Electrophosphorescent Polymer Light-Emitting Devices," *Organic Electronics*, 1:15-20 (2000).

Palilis, Leonidas C., "High Efficiency Molecular Organic Light-Emitting Diodes Based On Silole Derivatives And Their Exciplexes," *Organic Electronics*, 4:113-121 (2003).

Ikeda, Hisao et al., "P-185: Low-Drive-Voltage OLEDs with a Buffer Layer Having Molybdenum Oxide," *SID Symposium Digest*, 37:923-926 (2006).

T. Östergård et al., "Langmuir-Blodgett Light-Emitting Diodes Of Poly(3-Hexylthiophene): Electro-Optical Characteristics Related to Structure," *Synthetic Metals*, 87:171-177 (1997)

Hu, Nan-Xing et al., "Novel High $T_g$ Hole-Transport Molecules Based on Indolo[3,2-b]carbazoles for Organic Light-Emitting Devices," *Synthetic Metals*, 111-112:421-424 (2000).

Salbeck, J. et al., "Low Molecular Organic Glasses for Blue Electroluminescence," *Synthetic Metals*, 91:209-215 (1997).

Chinese Office Action in corresponding Chinese application No. 200880126458.4 dated Nov. 24, 2011.

\* cited by examiner

CARBAZOLE-CONTAINING MATERIALS IN PHOSPHORESCENT LIGHT EMITTING DIODES

This application is a continuation-in-part application and claims priority to and benefit under 35 U.S.C. §120 to U.S. application Ser. No. 12/209,928, filed Sep. 12, 2008, which claims priority to U.S. Provisional Application Ser. No. 61/017,480, filed Dec. 28, 2007. This application also claims priority to U.S. Provisional Application Ser. No. 61/017,391, filed Dec. 28, 2007. The contents of all of these applications are expressly incorporated fully herein by reference in their entirety.

The claimed invention was made by, on behalf of, and/or in connection with one or more of the following parties to a joint university corporation research agreement: Regents of the University of Michigan, Princeton University, The University of Southern California, and the Universal Display Corporation. The agreement was in effect on and before the date the claimed invention was made, and the claimed invention was made as a result of activities undertaken within the scope of the agreement.

FIELD OF THE INVENTION

The present invention relates to novel organic materials containing carbazole. In particular, the materials contain an oligocarbazole. The materials may be useful in organic light emitting devices (OLEDs).

BACKGROUND

Opto-electronic devices that make use of organic materials are becoming increasingly desirable for a number of reasons. Many of the materials used to make such devices are relatively inexpensive, so organic opto-electronic devices have the potential for cost advantages over inorganic devices. In addition, the inherent properties of organic materials, such as their flexibility, may make them well suited for particular applications such as fabrication on a flexible substrate. Examples of organic opto-electronic devices include organic light emitting devices (OLEDs), organic phototransistors, organic photovoltaic cells, and organic photodetectors. For OLEDs, the organic materials may have performance advantages over conventional materials. For example, the wavelength at which an organic emissive layer emits light may generally be readily tuned with appropriate dopants.

OLEDs make use of thin organic films that emit light when voltage is applied across the device. OLEDs are becoming an increasingly interesting technology for use in applications such as flat panel displays, illumination, and backlighting. Several OLED materials and configurations are described in U.S. Pat. Nos. 5,844,363, 6,303,238, and 5,707.745, which are incorporated herein by reference in their entirety.

One application for phosphorescent emissive molecules is a full color display. Industry standards for such a display call for pixels adapted to emit particular colors, referred to as "saturated" colors. In particular, these standards call for saturated red, green, and blue pixels. Color may be measured using CIE coordinates, which are well known to the art.

One example of a green emissive molecule is tris(2-phenylpyridine) iridium, denoted Ir(ppy)$_3$, which has the structure of Formula I:

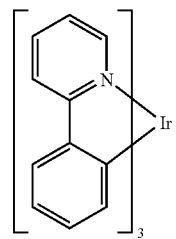

In this, and later figures herein, we depict the dative bond from nitrogen to metal (here, Ir) as a straight line.

As used herein, the term "organic" includes polymeric materials as well as small molecule organic materials that may be used to fabricate organic opto-electronic devices. "Small molecule" refers to any organic material that is not a polymer, and "small molecules" may actually be quite large. Small molecules may include repeat units in some circumstances. For example, using a long chain alkyl group as a substituent does not remove a molecule from the "small molecule" class. Small molecules may also be incorporated into polymers, for example as a pendent group on a polymer backbone or as a part of the backbone. Small molecules may also serve as the core moiety of a dendrimer, which consists of a series of chemical shells built on the core moiety. The core moiety of a dendrimer may be a fluorescent or phosphorescent small molecule emitter. A dendrimer may be a "small molecule," and it is believed that all dendrimers currently used in the field of OLEDs are small molecules.

As used herein, "top" means furthest away from the substrate, while "bottom" means closest to the substrate. Where a first layer is described as "disposed over" a second layer, the first layer is disposed further away from substrate. There may be other layers between the first and second layer, unless it is specified that the first layer is "in contact with" the second layer. For example, a cathode may be described as "disposed over" an anode, even though there are various organic layers in between.

As used herein, "solution processible" means capable of being dissolved, dispersed, or transported in and/or deposited from a liquid medium, either in solution or suspension form.

A ligand is referred to as "photoactive" when it is believed that the ligand contributes to the photoactive properties of an emissive material.

As used herein, the term "triplet energy" refers to an energy corresponding to the highest energy feature discernable in the phosphorescence spectrum of a given material. The highest energy feature is not necessarily the peak having the greatest intensity in the phosphorescence spectrum, and could, for example, be a local maximum of a clear shoulder on the high energy side of such a peak. Triplet energy is described in detail in U.S. Pat. No. 7,279,704 at col. 6, which is incorporated by reference.

More details on OLEDs, and the definitions described above, can be found in U.S. Pat. No. 7,279,704, which is incorporated herein by reference in its entirety.

SUMMARY OF THE INVENTION

A new class of carbazole-containing compounds are provided. In particular, compounds having a monodisperse linear 3,9-linked oligocarbazolyl (herein referred to as "oligocarbazole") are provided.

The carbazole-containing compounds described herein have the formula:

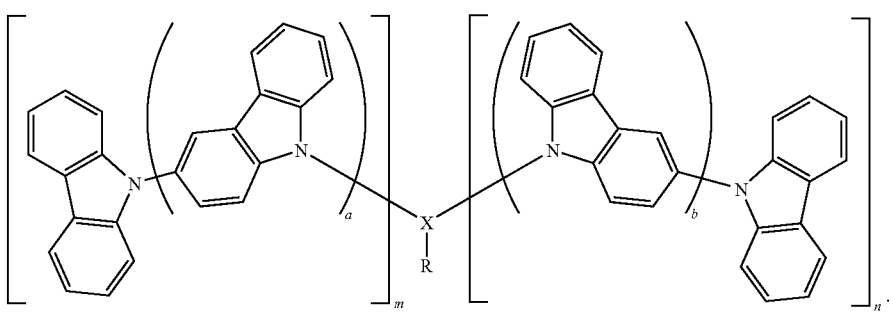

FORMULA I

Where a is 1 to 20, b is 0 to 20, m is 0 to 2, n is 0 to 2 and m+n is least 1. X is selected from biphenyl, terphenyl, naphthalene, triphenylene, phenanthrene, fluorene, chrysene, dibenzothiophene, dibenzofuran, benzofuran, benzothiophene, pyrazole, imidazole, triazole, oxazole, thiazole, oxadiazole, oxatriazole, dioxazole, thiadiazole, pyridine, pyridazine, pyrimidine, pyrazine, triazine, indole, benzimidazole, indazole, benzoxazole, benzisoxazole, benzothiazole, quinoline, isoquinoline, cinnoline, quinazoline, quinoxaline, naphthyridine, phthalazine, pteridine, xanthene, phenothiazine, phenoxazine, benzofuropyridine, furodipyridine, benzothienopyridine, and thienodipyridine. X is substituted by R, where R is selected from hydrogen, alkyl, heteroalkyl, benzene, biphenyl, terphenyl, naphthalene, phenalene, phenanthrene, fluorene, chrysene, dibenzothiophene, dibenzofuran, benzofuran, benzothiophene, pyrazole, imidazole, triazole, oxazole, thiazole, oxadiazole, oxatriazole, dioxazole, thiadiazole, pyridine, pyridazine, pyrimidine, pyrazine, triazine, indole, benzimidazole, indazole, benzoxazole, benzisoxazole, benzothiazole, quinoline, isoquinoline, cinnoline, quinazoline, quinoxaline, naphthyridine, phthalazine, pteridine, xanthene, phenothiazine, phenoxazine, benzofuropyridine, furodipyridine, benzothienopyridine, and thienodipyridine. Preferably, a is 1 to 20 and n is 0.

Examples of particular carbazole-containing materials include Compounds 1G-79G, as disclosed herein.

Additionally, an organic light emitting device is provided. The device has an anode, a cathode, and a first organic layer disposed between the anode and the cathode. The first organic layer further comprises an carbazole-containing compound having FORMULA I. Preferably the first organic layer is an emissive layer having a host and a phosphorescent emitter, and the carbazole-containing compound is the host. The device may contain 10-100 wt % of the carbazole-containing compound in an organic layer. Preferably, the carbazole-containing compound is present in an emissive layer at a concentration of 40-99.9 wt % and the emissive layer further comprises a phosphorescent emitter having a concentration of 0.1-30 wt %.

Moreover, the device may further comprise a non-emissive second organic layer and the carbazole-containing compound may also preferably be used as a material in the second layer of such a device.

A consumer product is also provided. The product contains a device that has an anode, a cathode, and an organic layer disposed between the anode and the cathode, where the organic layer further comprises a carbazole-containing compound having FORMULA I.

A method of fabricating an organic light emitting device is also provided. The method includes providing a first electrode, co-depositing a host and a phosphorescent emitter to form an emissive layer wherein the emissive layer comprises a carbazole-containing compound having FORMULA I, and depositing a second electrode. The first electrode may be an anode and the second electrode may be a cathode. An organic layer, preferably a hole transport layer, may be deposited after the anode and before the emissive layer.

DETAILED DESCRIPTION

Generally, an OLED comprises at least one organic layer disposed between and electrically connected to an anode and a cathode. When a current is applied, the anode injects holes and the cathode injects electrons into the organic layer(s). The injected holes and electrons each migrate toward the oppositely charged-electrode. When an electron and hole localize on the same molecule, an "exciton," which is a localized electron-hole pair having an excited energy state, is formed. Light is emitted when the exciton relaxes via a photoemissive mechanism. In some cases, the exciton may be localized on an excimer or an exciplex. Non-radiative mechanisms, such as thermal relaxation, may also occur, but are generally considered undesirable.

The initial OLEDs used emissive molecules that emitted light from their singlet states ("fluorescence") as disclosed, for example, in U.S. Pat. No. 4,769,292, which is incorporated by reference in its entirety. Fluorescent emission generally occurs in a time frame of less than 10 nanoseconds.

More recently, OLEDs having emissive materials that emit light from triplet states ("phosphorescence") have been demonstrated. Baldo et al., "Highly Efficient Phosphorescent Emission from Organic Electroluminescent Devices," Nature, vol. 395, 151-154, 1998; ("Baldo-I") and Baldo et al., "Very high-efficiency green organic light-emitting devices based on electrophosphorescence," Appl. Phys. Lett., vol. 75, No. 3, 4-6 (1999) ("Baldo-II"), which are incorporated by reference in their entireties. Phosphorescence is described in more detail in U.S. Pat. No. 7,279,704 at cols. 5-6, which are incorporated by reference.

Figure 1:
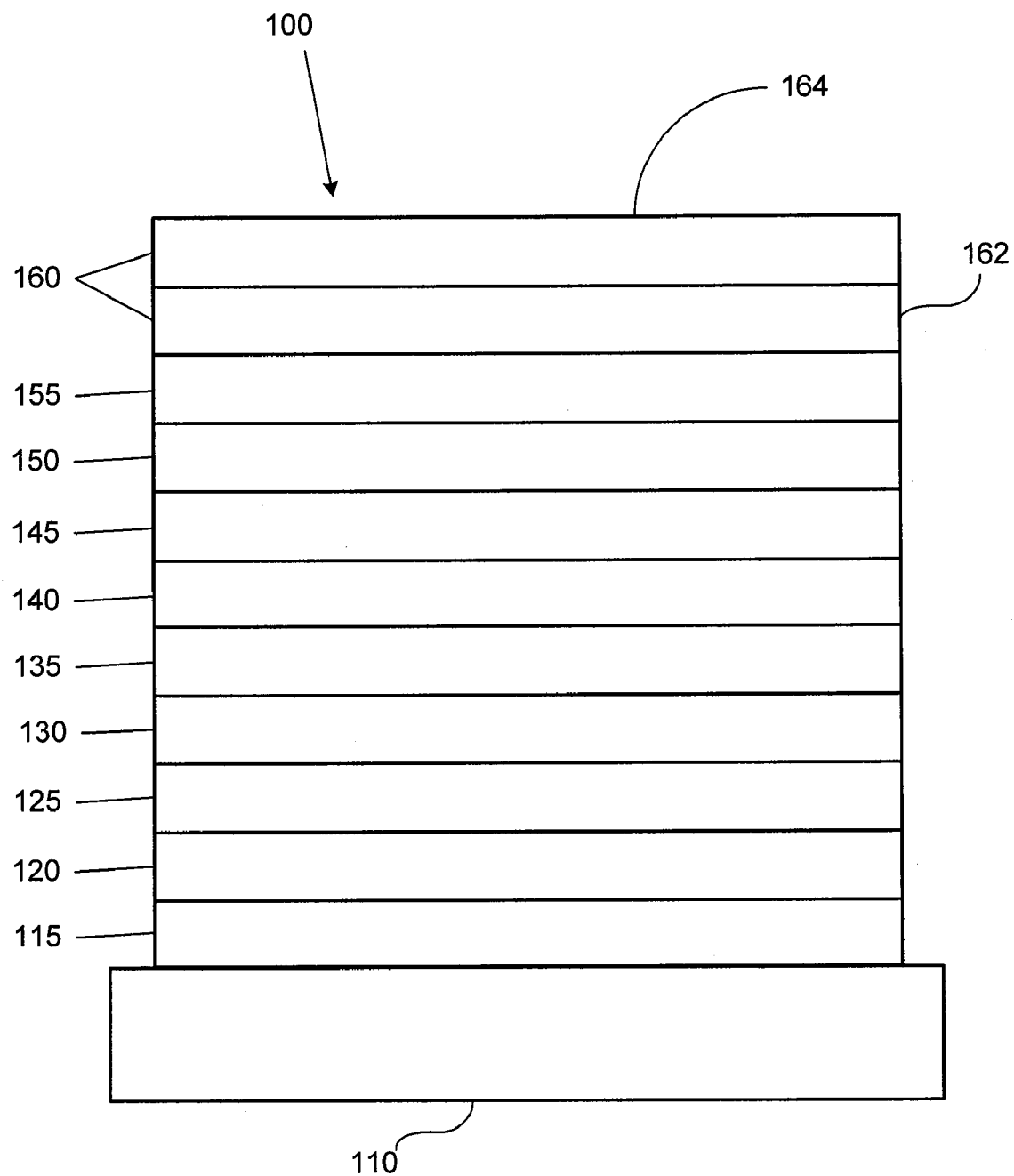
FIG. 1 shows an organic light emitting device.

FIG. 1 shows an organic light emitting device 100. The figures are not necessarily drawn to scale. Device 100 may include a substrate 110, an anode 115, a hole injection layer 120, a hole transport layer 125, an electron blocking layer 130, an emissive layer 135, a hole blocking layer 140, an electron transport layer 145, an electron injection layer 150, a protective layer 155, and a cathode 160. Cathode 160 is a compound cathode having a first conductive layer 162 and a second conductive layer 164. Device 100 may be fabricated by depositing the layers described, in order. The properties and functions of these various layers, as well as example materials, are described in more detail in U.S. Pat. No. 7,279,704 at cols. 6-10, which are incorporated by reference.

More examples for each of these layers are available. For example, a flexible and transparent substrate-anode combination is disclosed in U.S. Pat. No. 5,844,363, which is incorporated by reference in its entirety. An example of a p-doped hole transport layer is m-MTDATA doped with F.sub.4-TCNQ at a molar ratio of 50:1, as disclosed in U.S. Patent Application Publication No. 2003/0230980, which is incorporated by reference in its entirety. Examples of emissive and host materials are disclosed in U.S. Pat. No. 6,303,238 to Thompson et al., which is incorporated by reference in its entirety. An example of an n-doped electron transport layer is BPhen doped with Li at a molar ratio of 1:1, as disclosed in U.S. Patent Application Publication No. 2003/0230980, which is incorporated by reference in its entirety. U.S. Pat. Nos. 5,703,436 and 5,707,745, which are incorporated by reference in their entireties, disclose examples of cathodes including compound cathodes having a thin layer of metal such as Mg:Ag with an overlying transparent, electrically-conductive, sputter-deposited ITO layer. The theory and use of blocking layers is described in more detail in U.S. Pat. No. 6,097,147 and U.S. Patent Application Publication No. 2003/0230980, which are incorporated by reference in their entireties. Examples of injection layers are provided in U.S. Patent Application Publication No. 2004/0174116, which is incorporated by reference in its entirety. A description of protective layers may be found in U.S. Patent Application Publication No. 2004/0174116, which is incorporated by reference in its entirety.

Figure 2:
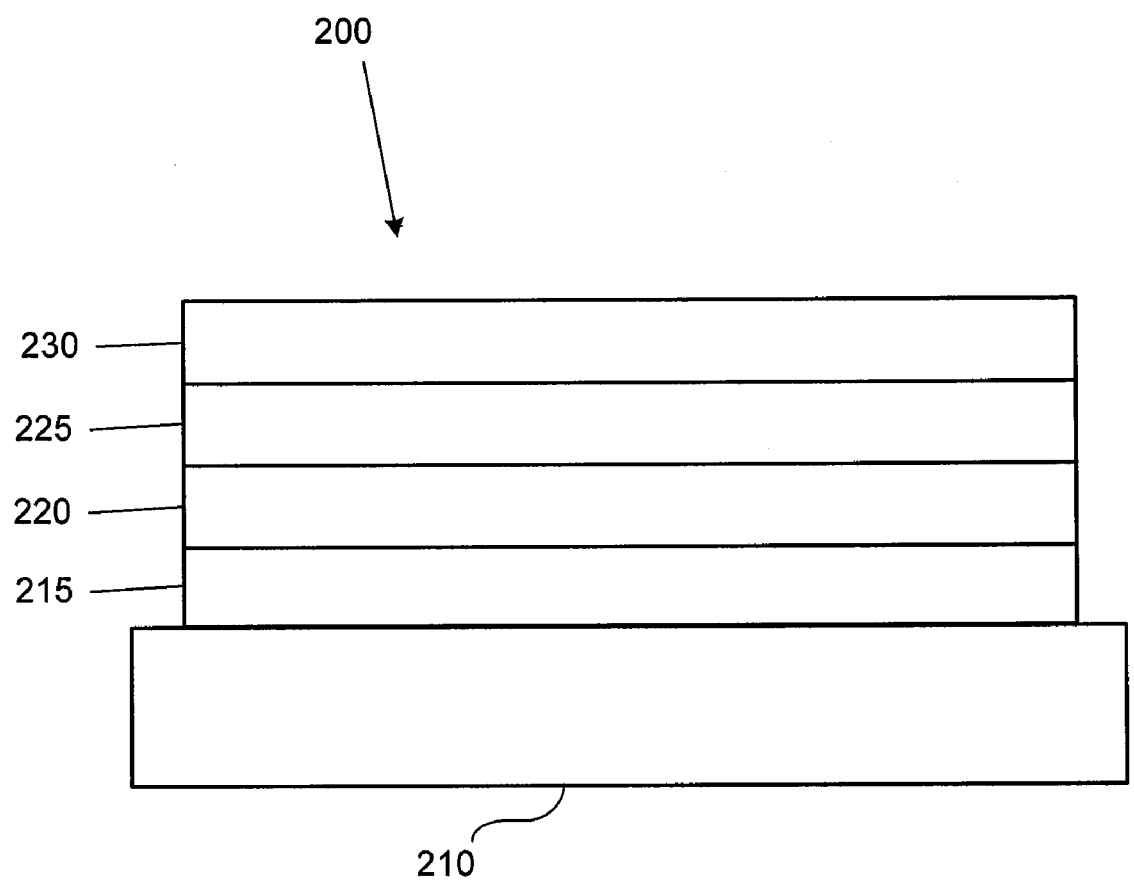
FIG. 2 shows an inverted organic light emitting device that does not have a separate electron transport layer.

FIG. 2 shows an inverted OLED 200. The device includes a substrate 210, a cathode 215, an emissive layer 220, a hole transport layer 225, and an anode 230. Device 200 may be fabricated by depositing the layers described, in order. Because the most common OLED configuration has a cathode disposed over the anode, and device 200 has cathode 215 disposed under anode 230, device 200 may be referred to as an "inverted" OLED. Materials similar to those described with respect to device 100 may be used in the corresponding layers of device 200. FIG. 2 provides one example of how some layers may be omitted from the structure of device 100.

The simple layered structure illustrated in FIGS. 1 and 2 is provided by way of non-limiting example, and it is understood that embodiments of the invention may be used in connection with a wide variety of other structures. The specific materials and structures described are exemplary in nature, and other materials and structures may be used. Functional OLEDs may be achieved by combining the various layers described in different ways, or layers may be omitted entirely, based on design, performance, and cost factors. Other layers not specifically described may also be included. Materials other than those specifically described may be used. Although many of the examples provided herein describe various layers as comprising a single material, it is understood that combinations of materials, such as a mixture of host and dopant, or more generally a mixture, may be used. Also, the layers may have various sublayers. The names given to the various layers herein are not intended to be strictly limiting. For example, in device 200, hole transport layer 225 transports holes and injects holes into emissive layer 220, and may be described as a hole transport layer or a hole injection layer. In one embodiment, an OLED may be described as having an "organic layer" disposed between a cathode and an anode. This organic layer may comprise a single layer, or may further comprise multiple layers of different organic materials as described, for example, with respect to FIGS. 1 and 2.

Structures and materials not specifically described may also be used, such as OLEDs comprised of polymeric materials (PLEDs) such as disclosed in U.S. Pat. No. 5,247,190 to Friend et al., which is incorporated by reference in its entirety. By way of further example, OLEDs having a single organic layer may be used. OLEDs may be stacked, for example as described in U.S. Pat. No. 5,707,745 to Forrest et al, which is incorporated by reference in its entirety. The OLED structure may deviate from the simple layered structure illustrated in FIGS. 1 and 2. For example, the substrate may include an angled reflective surface to improve out-coupling, such as a mesa structure as described in U.S. Pat. No. 6,091,195 to Forrest et al., and/or a pit structure as described in U.S. Pat. No. 5,834,893 to Bulovic et al., which are incorporated by reference in their entireties.

Unless otherwise specified, any of the layers of the various embodiments may be deposited by any suitable method. For the organic layers, preferred methods include thermal evaporation, ink-jet, such as described in U.S. Pat. Nos. 6,013,982 and 6,087,196, which are incorporated by reference in their entireties, organic vapor phase deposition (OVPD), such as described in U.S. Pat. No. 6,337,102 to Forrest et al., which is incorporated by reference in its entirety, and deposition by organic vapor jet printing (OVJP), such as described in U.S. patent application Ser. No. 10/233,470, which is incorporated by reference in its entirety. Other suitable deposition methods include spin coating and other solution based processes. Solution based processes are preferably carried out in nitrogen or an inert atmosphere. For the other layers, preferred methods include thermal evaporation. Preferred patterning methods include deposition through a mask, cold welding such as described in U.S. Pat. Nos. 6,294,398 and 6,468,819, which are incorporated by reference in their entireties, and patterning associated with some of the deposition methods such as ink-jet and OVJD. Other methods may also be used. The materials to be deposited may be modified to make them compatible with a particular deposition method. For example, substituents such as alkyl and aryl groups, branched or unbranched, and preferably containing at least 3 carbons, may be used in small molecules to enhance their ability to undergo solution processing. Substituents having 20 carbons or more may be used, and 3-20 carbons is a preferred range. Materials with asymmetric structures may have better solution processability than those having symmetric structures, because asymmetric materials may have a lower tendency to recrystallize. Dendrimer substituents may be used to enhance the ability of small molecules to undergo solution processing.

Devices fabricated in accordance with embodiments of the invention may be incorporated into a wide variety of consumer products, including flat panel displays, computer monitors, televisions, billboards, lights for interior or exterior illumination and/or signaling, heads up displays, fully transparent displays, flexible displays, laser printers, telephones, cell phones, personal digital assistants (PDAs), laptop computers, digital cameras, camcorders, viewfinders, micro-displays, vehicles, a large area wall, theater or stadium screen, or a sign. Various control mechanisms may be used to control devices fabricated in accordance with the present invention, including passive matrix and active matrix. Many of the devices are intended for use in a temperature range comfortable to humans, such as 18 degrees C. to 30 degrees C., and more preferably at room temperature (20-25 degrees C.).

The materials and structures described herein may have applications in devices other than OLEDs. For example, other optoelectronic devices such as organic solar cells and organic photodetectors may employ the materials and structures. More generally, organic devices, such as organic transistors, may employ the materials and structures.

The terms halo, halogen, alkyl, cycloalkyl, alkenyl, alkynyl, arylkyl, heterocyclic group, aryl, aromatic group, and heteroaryl are known to the art, and are defined in U.S. Pat. No. 7,279,704 at cols. 31-32, which are incorporated herein by reference.

Figure 3:
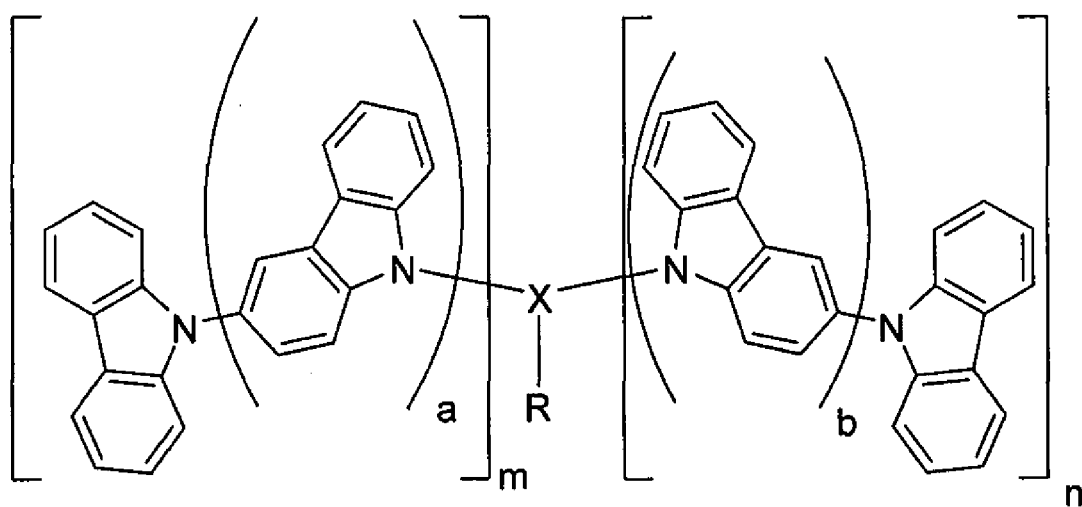
FIG. 3 shows an oligocarbazole-containing compound.

A new class of carbazole-containing compounds, which may be advantageously used in an OLED, are provided (also illustrated in FIG. 3). In particular, 3,9-linked oligocarbazolyl compounds ("oligocarbazole-containing compounds") are provided. Carbazole is a nitrogen containing heteroaromatic, having high triplet energy, and has hole transporting and electron transporting properties. One advantage to using carbazole-containing compounds as host materials is that they simultaneously possess sufficiently large triplet energies and carrier transport properties. The 3,9-linked oligocarbazole groups (i.e., carbazole groups that are linked para to the nitrogen) are monodisperse, well-defined π-conjugated oligomers that may be useful in OLEDs. There is a minimal reduction in the triplet energy in going from carbazole monomers to oligocarbazoles. In addition, oligomerization of the carbazole group allows for tuning of the HOMO level to improve hole stability.

The oligocarbazole-containing compounds described herein have a relatively low electrochemical oxidation potential. As such, these compounds are easier to oxidize and to reverse the oxidation, which improves overall host stability. In particular, the materials disclosed herein may have less than about 0.9 V, less than about 0.85 V, less than about 0.8 V, and less than 0.75 V oxidation relative to ferrocene/ferrocenium (vs. Fc$^+$/Fc). It is thought that the asymmetrical arrangement of the compound around the carbazole provides the lower oxidation potential and reversible nature of the oxidation potential. As used herein, the term "asymmetrical" refers to the arrangement of chemical groups in the compound in such a way that is not symmetrical with respect to the carbazole portion of the compound.

In addition to improved charge balance and charge stability, the materials provided herein may also provide better film formation. In particular, materials having an asymmetrical structure, such as the 3,9-linked oligocarbazole structure, may offer improved film formation. The improved film formation is believed to be a result of reduced crystallization due to the asymmetrical structure of the compound.

The carbazole-containing compounds described herein have the formula:

Where a is 1 to 20, b is 0 to 20, m is 0 to 2, n is 0 to 2 and m+n is least 1. X is selected from biphenyl, terphenyl, naphthalene, triphenylene, phenanthrene, fluorene, chrysene, dibenzothiophene, dibenzofuran, benzofuran, benzothiophene, pyrazole, imidazole, triazole, oxazole, thiazole, oxadiazole, oxatriazole, dioxazole, thiadiazole, pyridine, pyridazine, pyrimidine, pyrazine, triazine, indole, benzimidazole, indazole, benzoxazole, benzisoxazole, benzothiazole, quinoline, isoquinoline, cinnoline, quinazoline, quinoxaline, naphthyridine, phthalazine, pteridine, xanthene, phenothiazine, phenoxazine, benzofuropyridine, furodipyridine, benzothienopyridine, and thienodipyridine. X is substituted by R, where R is selected from hydrogen, alkyl, heteroalkyl, benzene, biphenyl, terphenyl, naphthalene, phenalene, phenanthrene, fluorene, chrysene, dibenzothiophene, dibenzofuran, benzofuran, benzothiophene, pyrazole, imidazole, triazole, oxazole, thiazole, oxadiazole, oxatriazole, dioxazole, thiadiazole, pyridine, pyridazine, pyrimidine, pyrazine, triazine, indole, benzimidazole, indazole, benzoxazole, benzisoxazole, benzothiazole, quinoline, isoquinoline, cinnoline, quinazoline, quinoxaline, naphthyridine, phthalazine, pteridine, xanthene, phenothiazine, phenoxazine, benzofuropyridine, furodipyridine, benzothienopyridine, and thienodipyridine.

In one aspect, carbazole-containing compounds are provided wherein a is 1 to 20 and n is 0. In one aspect, particular carbazole-containing compounds are provided, wherein a is 1 or 2 and n is 0.

In another aspect, particular carbazole-containing compounds are provided, wherein a is 1, b is 1 and n is 1.

The X group of the compound is an electron transporting material selected from a group of aromatics having relatively high triplet energy. Preferably, X has a low LUMO level (e.g., heteroaromatics) and provides delocalization via aromatic rings (e.g., up to four conjugated aromatic rings). By using groups having a relatively high triplet energy as X, the overall high triplet energy of the compound due to the carbazole moiety can be maintained. Therefore, materials as described herein having both an oligocarbazole moiety and an X moiety in the same compound maintain a beneficial high triplet energy and also may improve charge balance and device stability.

In one aspect, particular carbazole-containing compounds are provided wherein X is selected from biphenyl, terphenyl, triphenylene, phenanthrene, fluorene, dibenzothiophene, dibenzofuran, pyridine, pyridazine, pyrimidine, pyrazine, triazine, benzimidazole, benzothiazole, quinoline, isoquinoline, benzofuropyridine, furodipyridine, benzothienopyri-

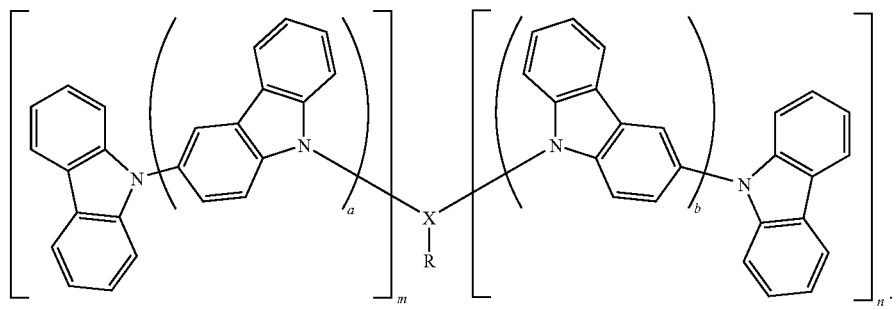

FORMULA I dine, and thienodipyridine. In another aspect, particular carbazole-containing compounds are provided wherein X is selected from dibenzothiophene, dibenzofuran, benzofuropyridine, furodipyridine, benzothienopyridine, and thienodipyridine.

The X of the compound is further substituted with a substituent R. Preferably, the substituent R has a sufficiently high triplet energy to maintain the benefit of having both oligocarbazole and X in the same compound. Examples of such groups that can be used as R may include hydrogen, alkyl, heteroalkyl, benzene, biphenyl, terphenyl, naphthalene, phenalene, phenanthrene, fluorene, chrysene, dibenzothiophene, dibenzofuran, benzofuran, benzothiophene, pyrazole, imidazole, triazole, oxazole, thiazole, oxadiazole, oxatriazole, dioxazole, thiadiazole, pyridine, pyridazine, pyrimidine, pyrazine, triazine, indole, benzimidazole, indazole, benzoxazole, benzisoxazole, benzothiazole, quinoline, isoquinoline, cinnoline, quinazoline, quinoxaline, naphthyridine, phthalazine, pteridine, xanthene, phenothiazine, phenoxazine, benzofuropyridine, furodipyridine, benzothienopyridine, and thienodipyridine.

In one aspect, certain compounds are provided wherein R is selected from hydrogen, alkyl, benzene, biphenyl, terphenyl, triphenylene, phenanthrene, fluorene, dibenzothiophene, dibenzofuran, pyridine, pyridazine, pyrimidine, pyrazine, triazine, benzimidazole, benzothiazole, quinoline, isoquinoline, benzofuropyridine, furodipyridine, benzothienopyridine, and thienodipyridine. Due to their high triplet energy, these R groups are well-suited for devices having green or red emitters. In particular, these R groups are especially well suited for devices having green emitters. In another aspect, certain compounds are provided wherein R is selected from hydrogen, alkyl, benzene, biphenyl, terphenyl, dibenzothiophene, dibenzofuran. Due to their even higher triplet energy, these R groups are well-suited for use in devices having red, green or emitters. In particular, these R groups are especially well-suited for devices having blue emitters.

Specific examples of carbazole-containing compounds include compounds selected from the group consisting of:

Compound 1G

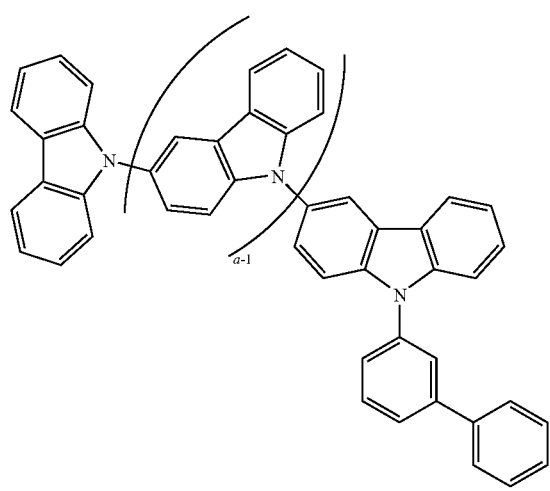

Compound 2G

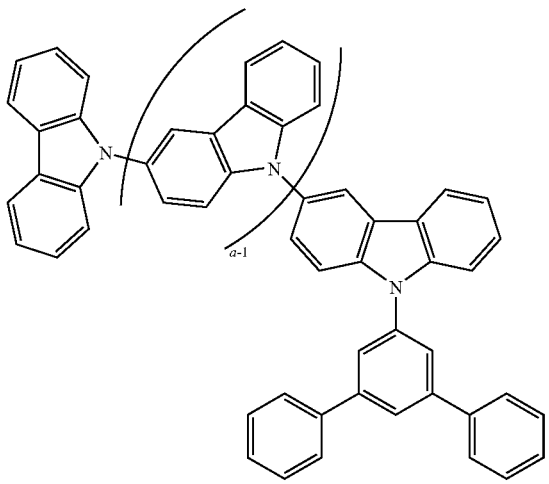

Compound 3G

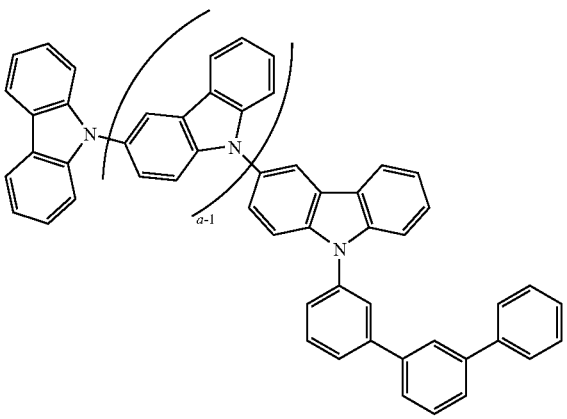

Compound 4G

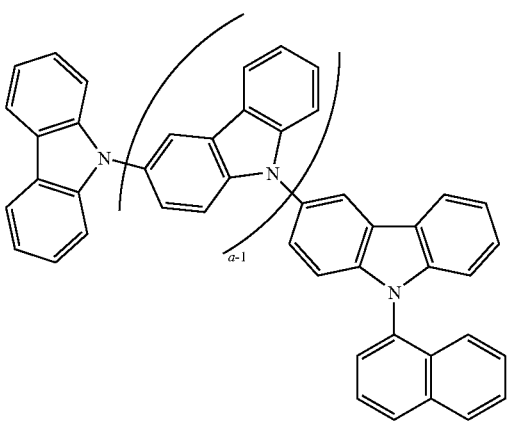

Compound 5G
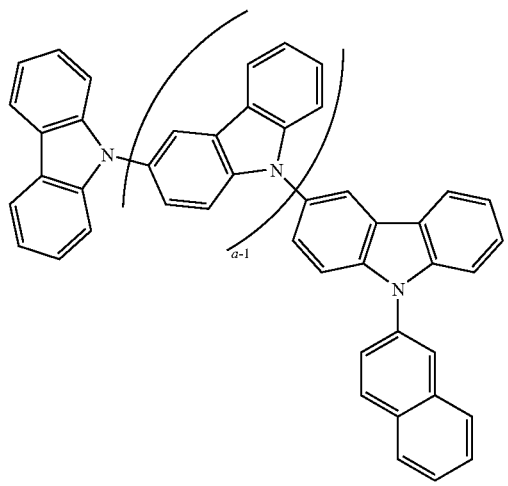
Compound 6G
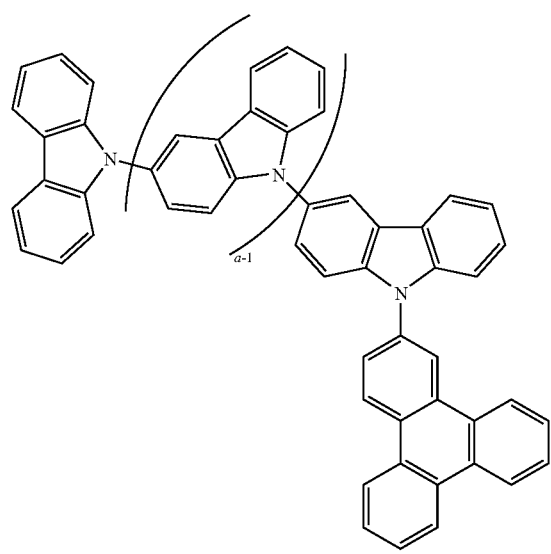
Compound 7G
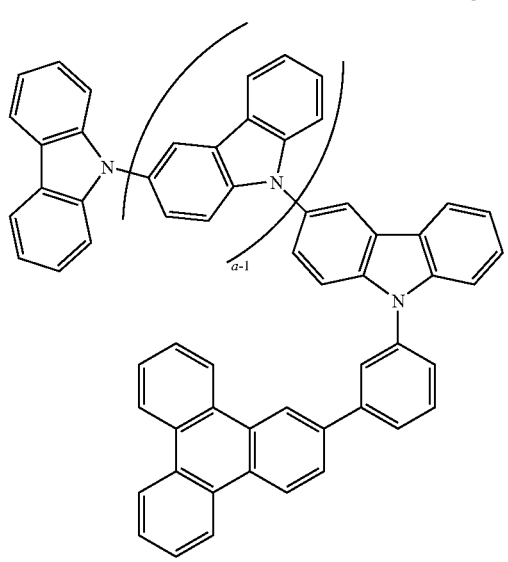
Compound 8G
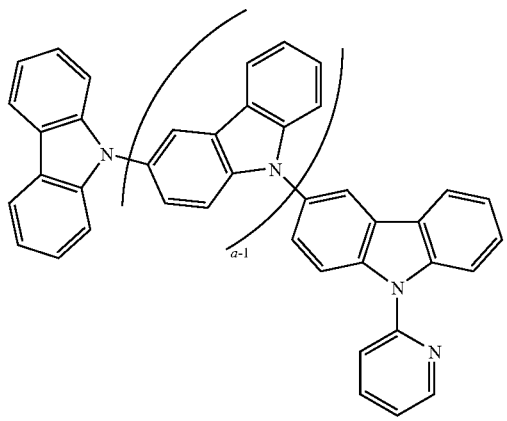
Compound 9G
Compound 10G
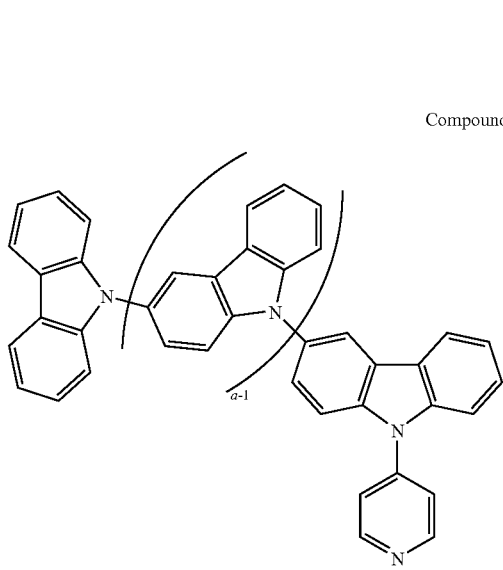

Compound 11G
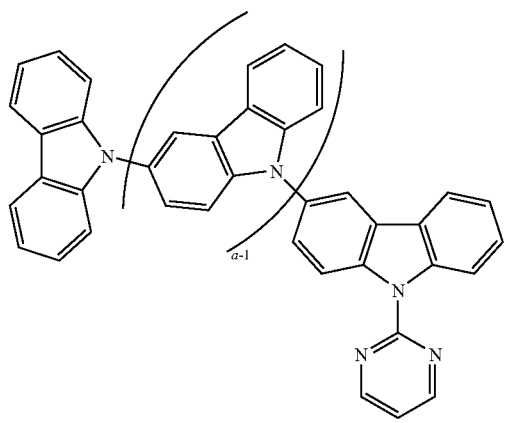
Compound 12G
Compound 13G
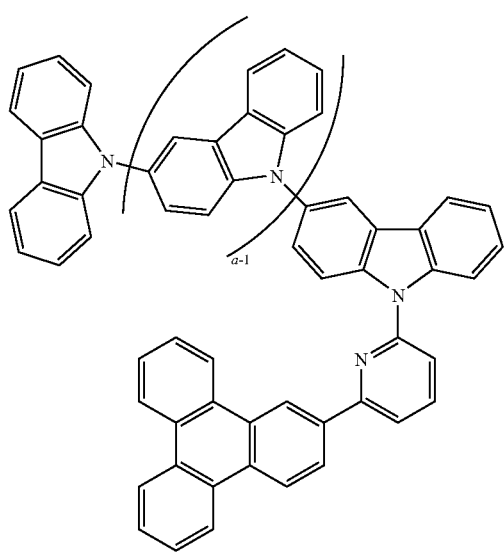
Compound 14G
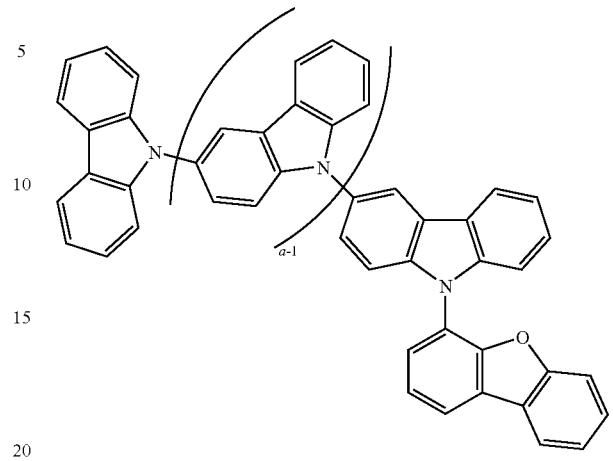
Compound 15G
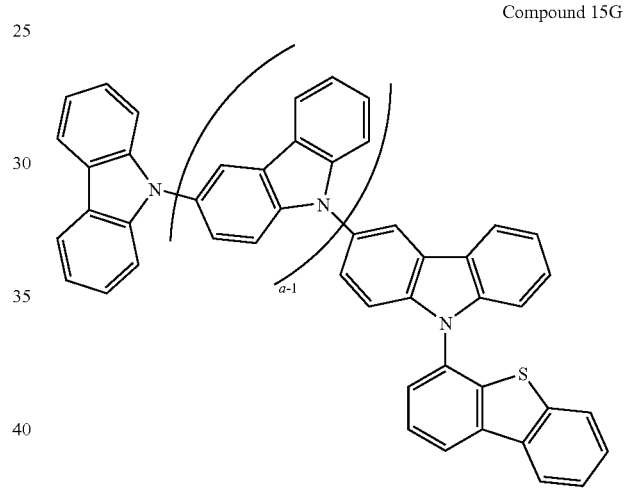
Compound 16G
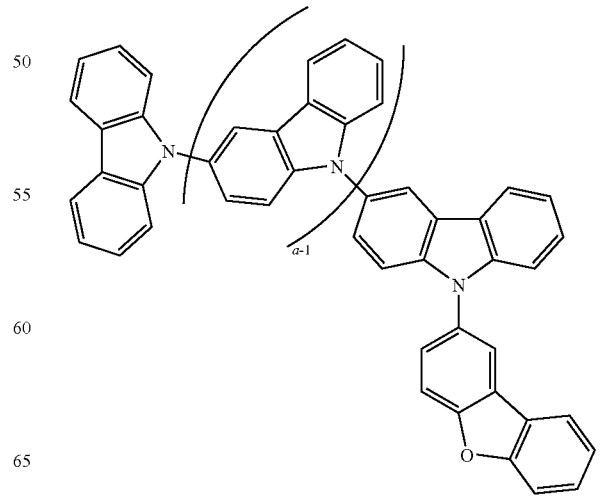

Compound 17G
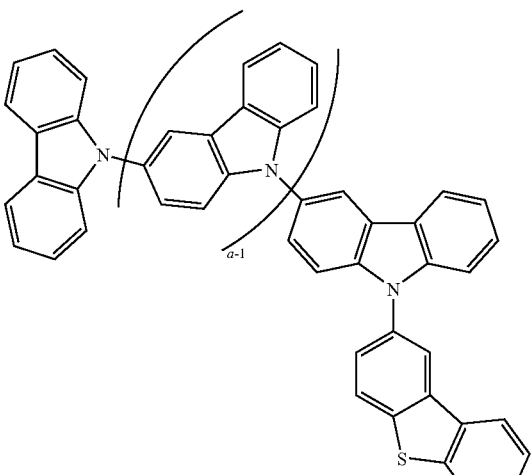
Compound 18G
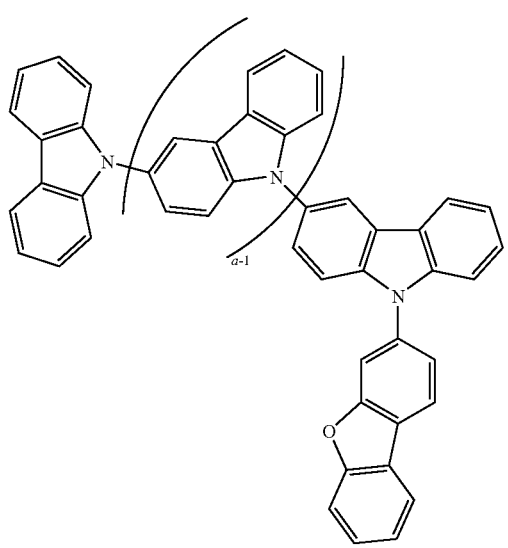
Compound 19G
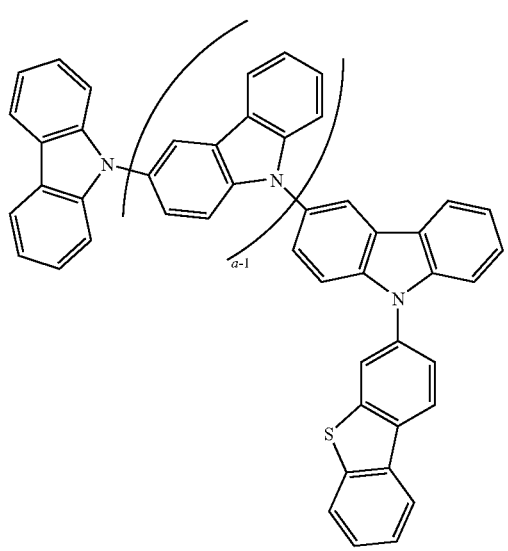
Compound 20G
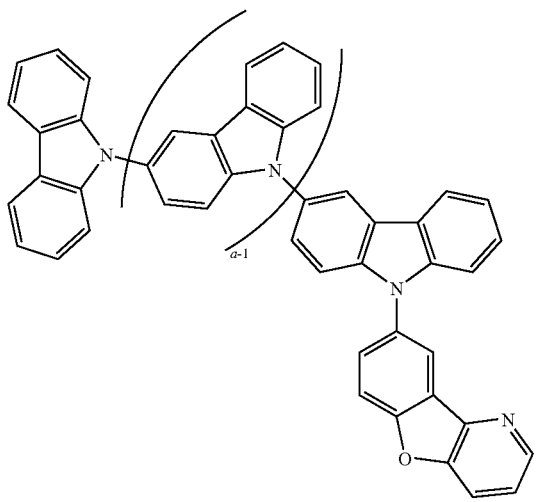
Compound 21G
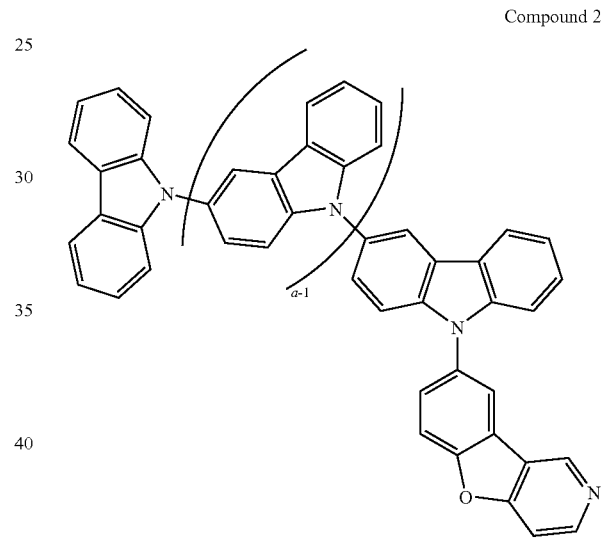
Compound 22G
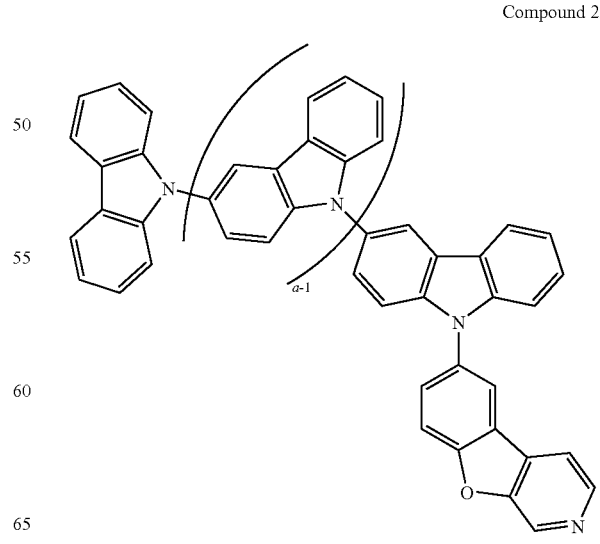

-continued
Compound 23G
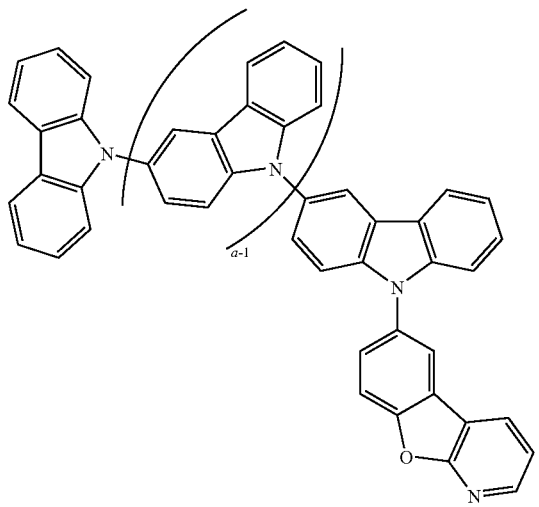
Compound 24G
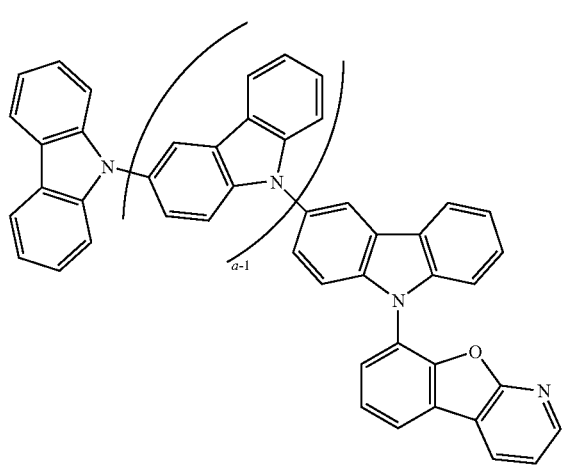
Compound 25G
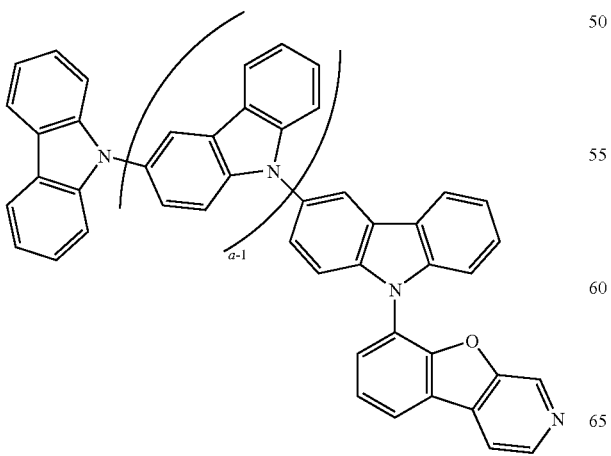
Compound 26G
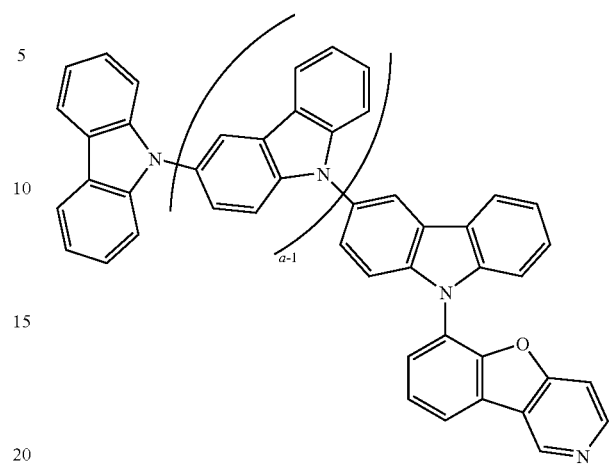
Compound 27G
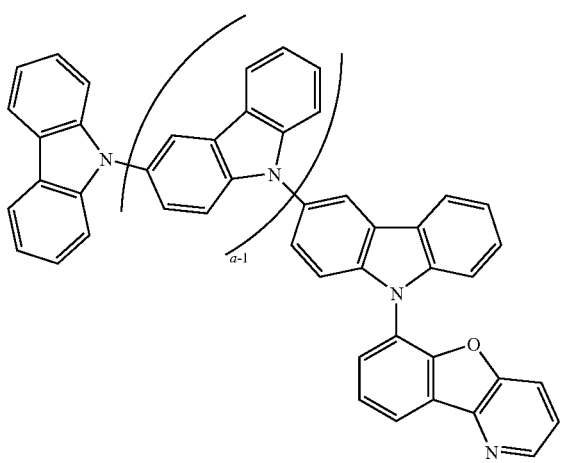
Compound 28G
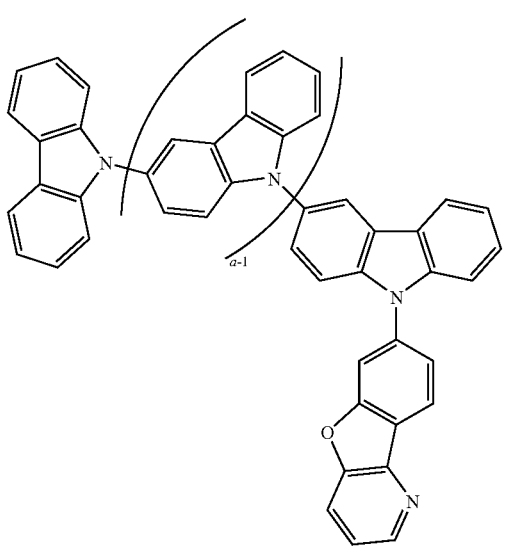

Compound 29G
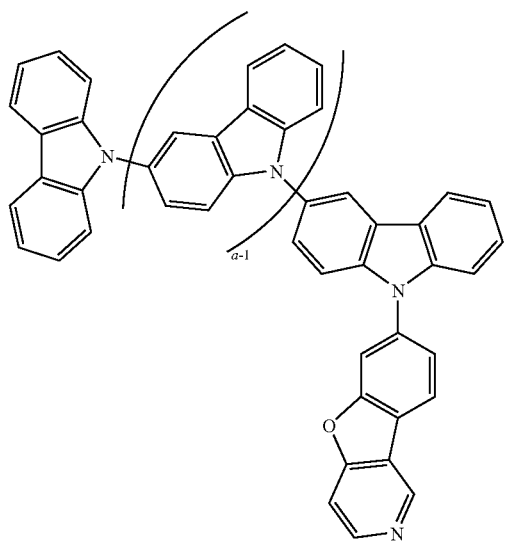
Compound 30G
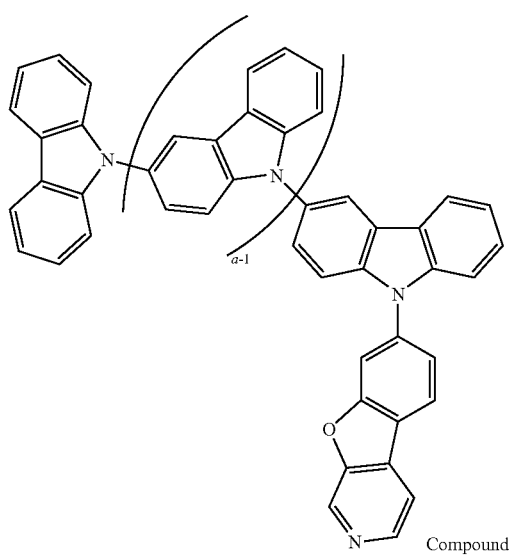
Compound 31G
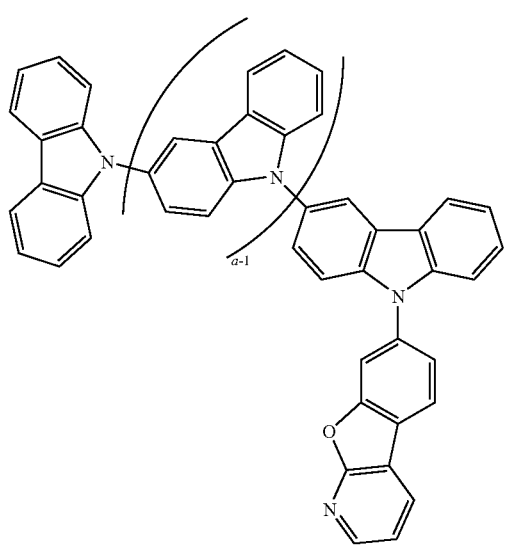
Compound 32G
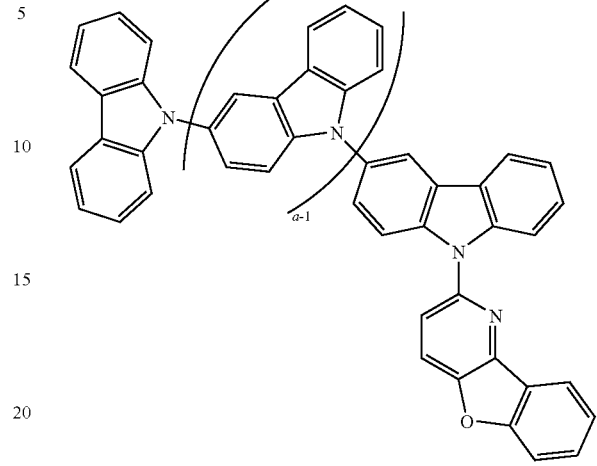
Compound 33G
Compound 34G
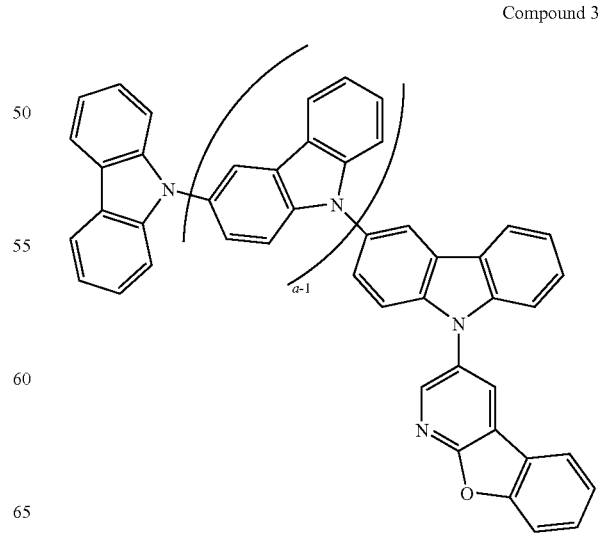

Compound 35G
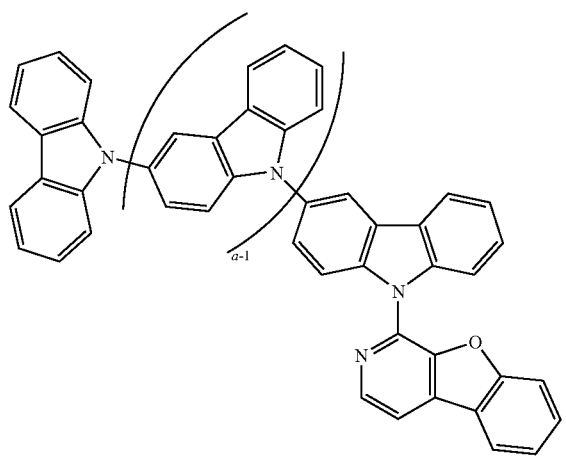
Compound 36G
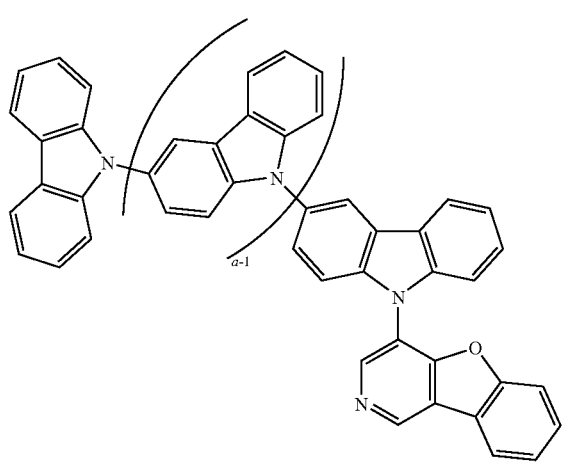
Compound 37G
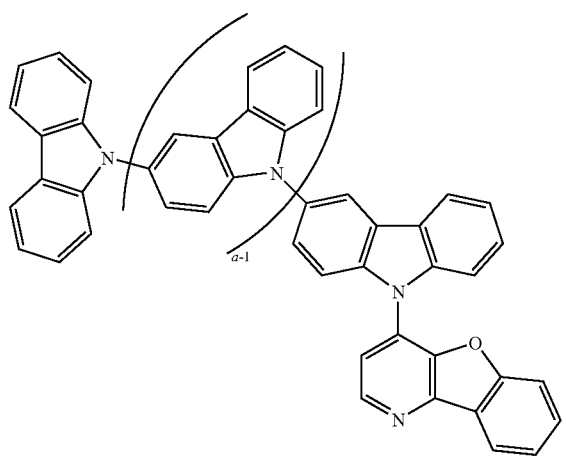
Compound 38G
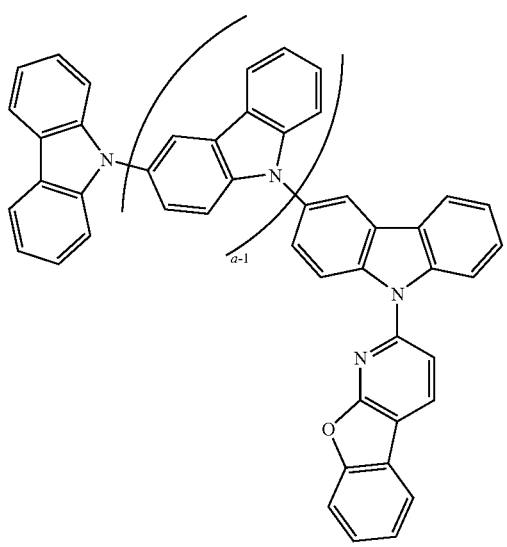
Compound 39G
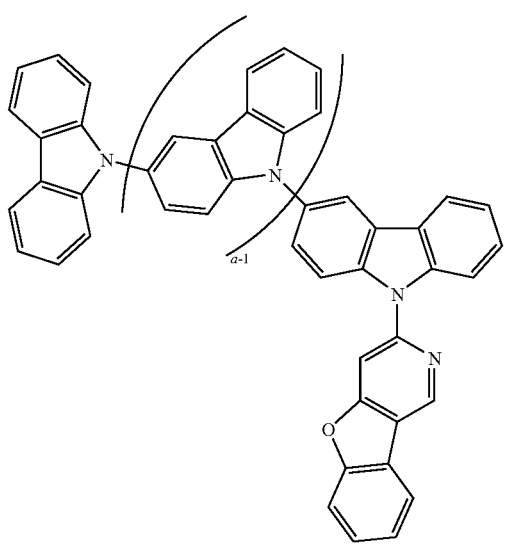
Compound 40G
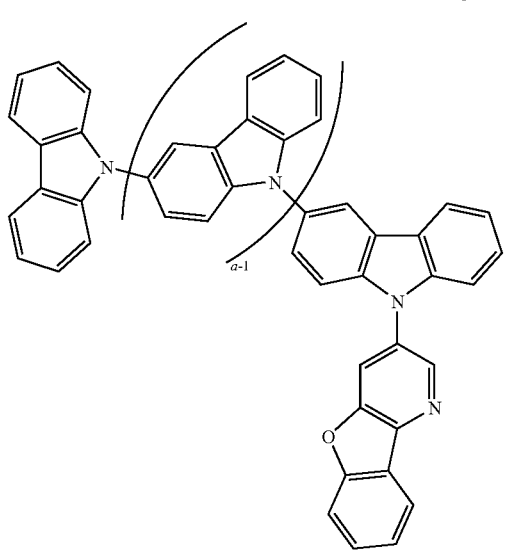

Compound 41G
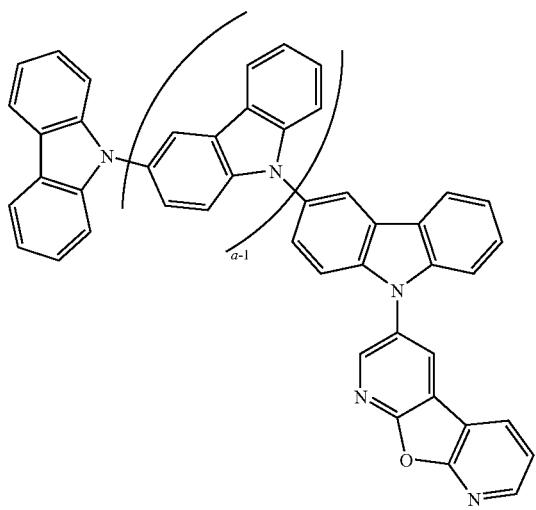
Compound 42G
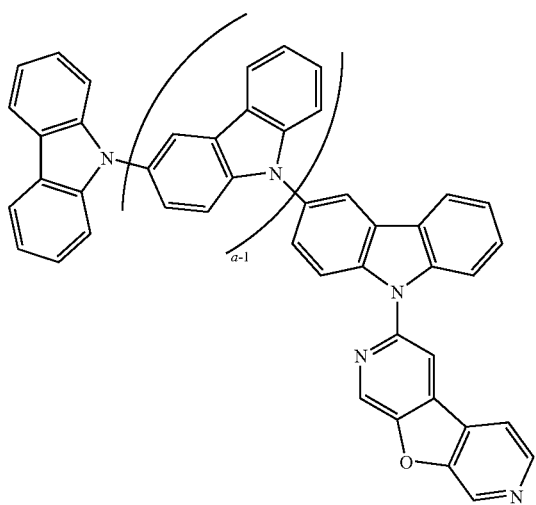
Compound 43G
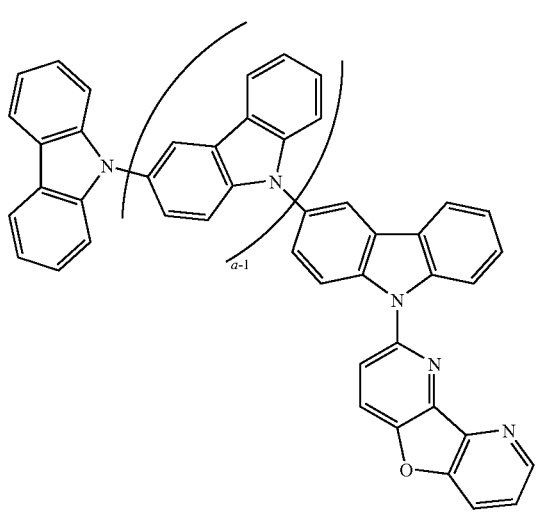
Compound 44G
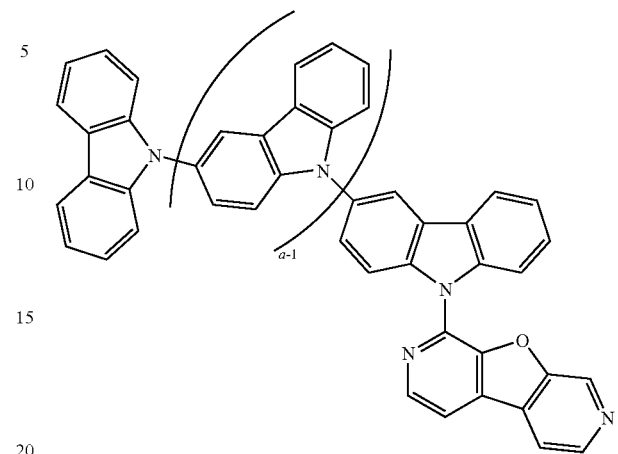
Compound 45G
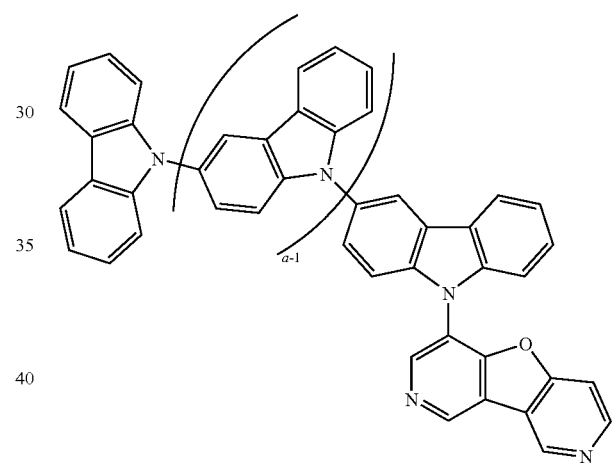
Compound 46G
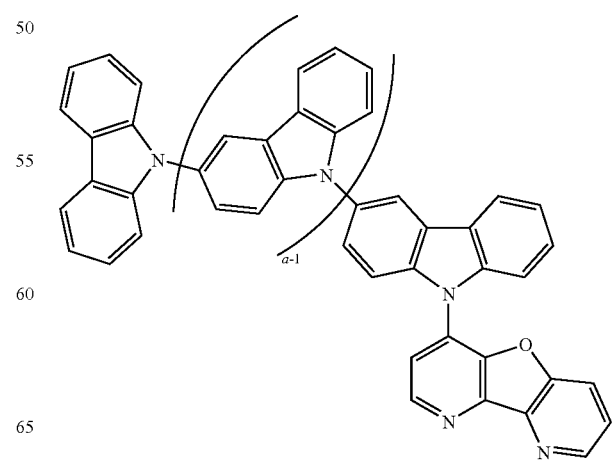

Compound 47G
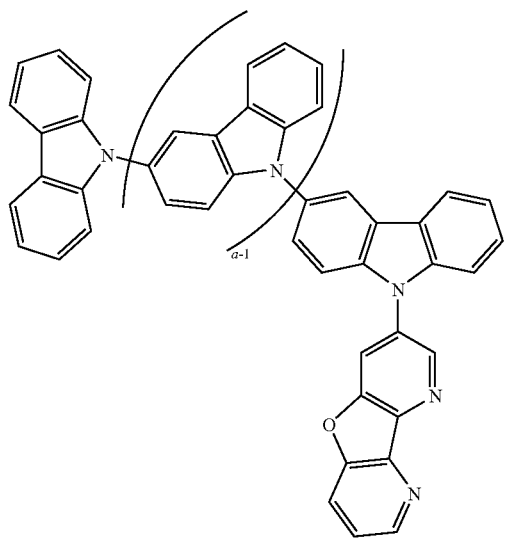
Compound 48G
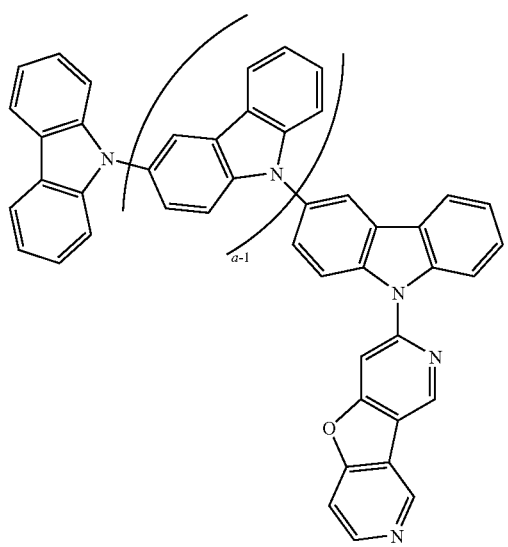
Compound 49G
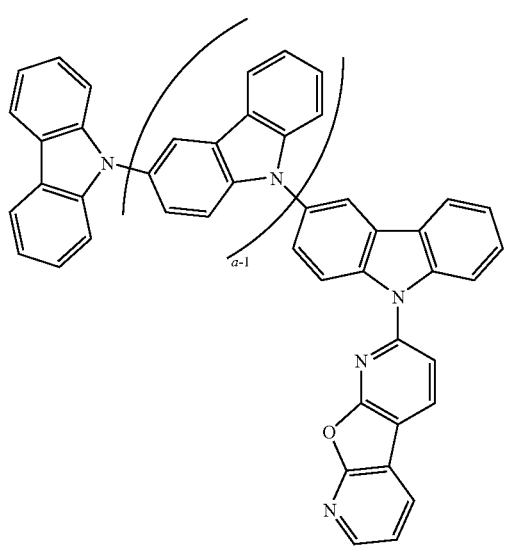
Compound 50G
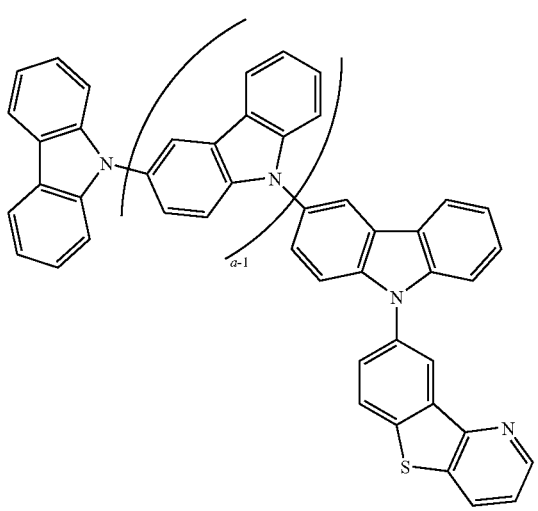
Compound 51G
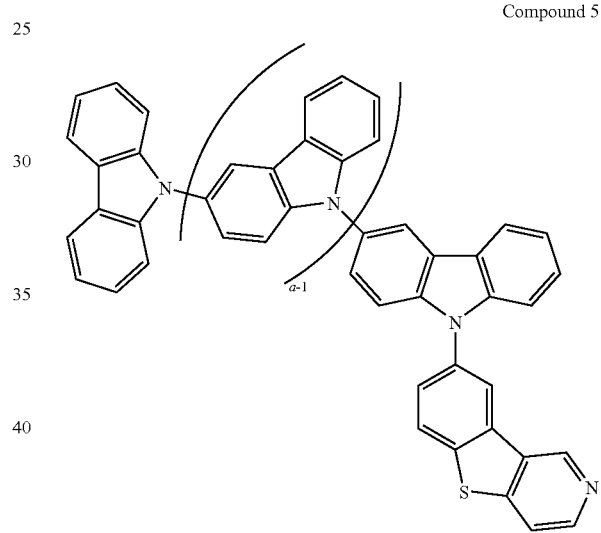
Compound 52G
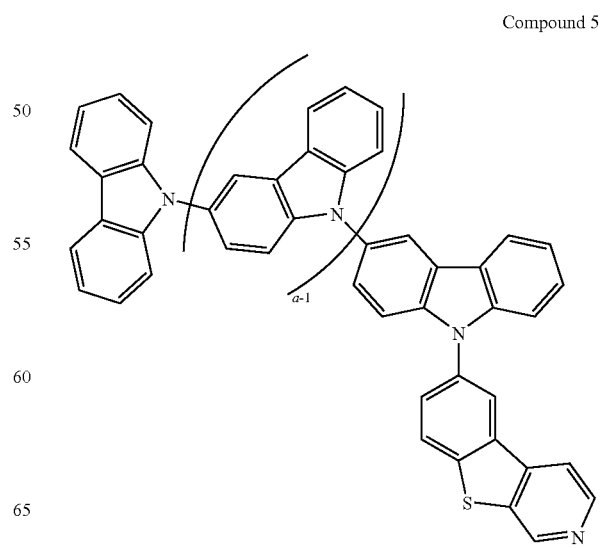

Compound 53G
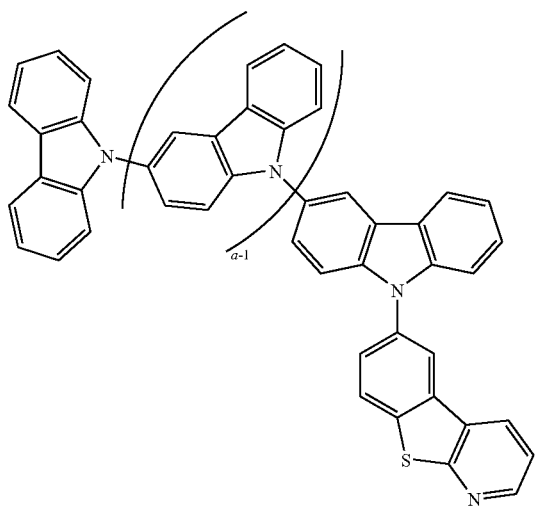
Compound 54G
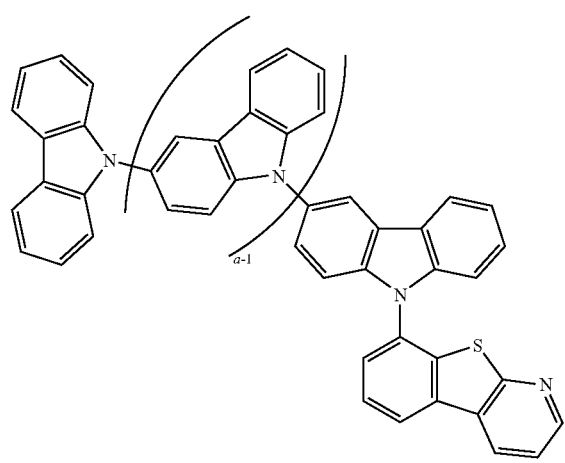
Compound 55G
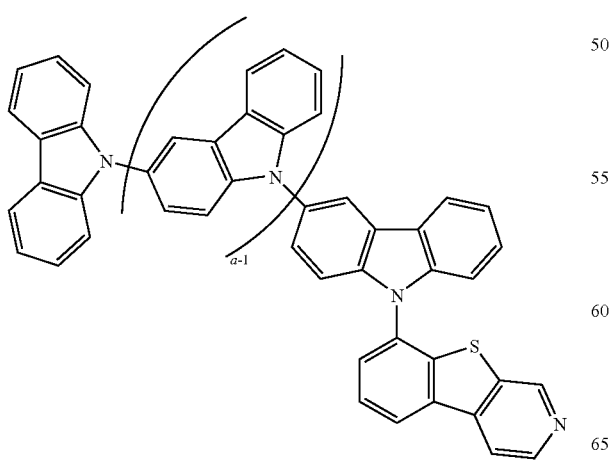
Compound 56G
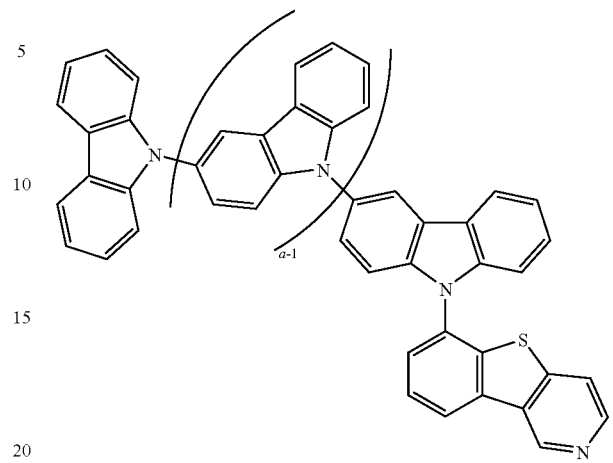
Compound 57G
Compound 58G
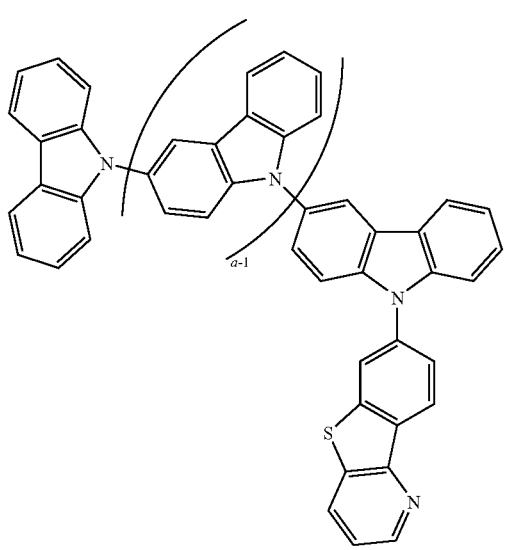

Compound 59G
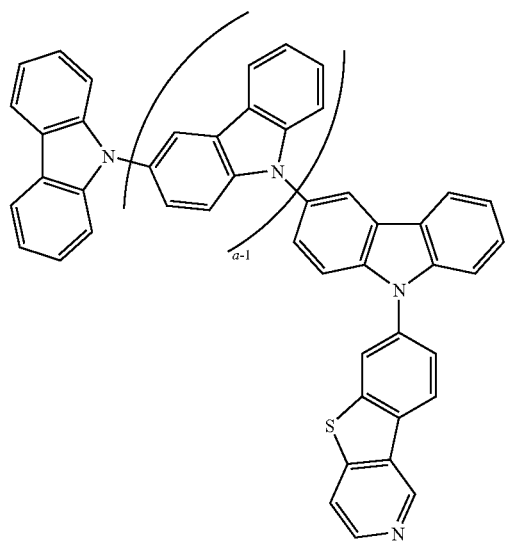
Compound 60G
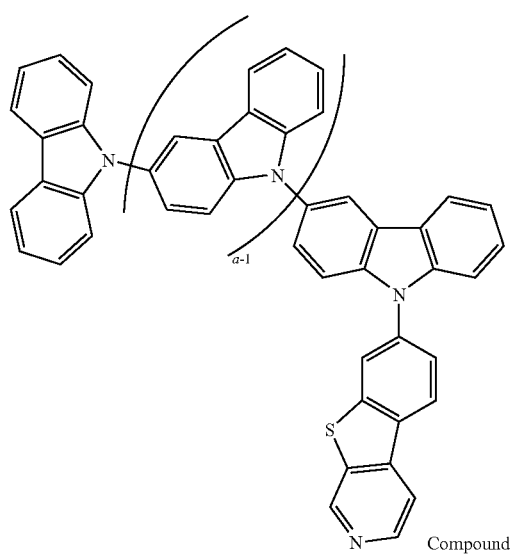
Compound 61G
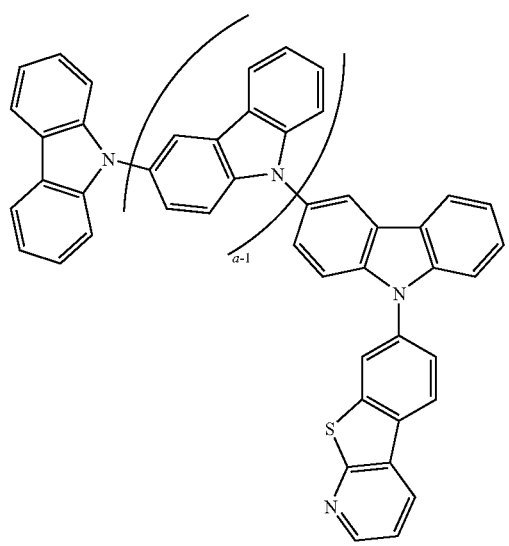
Compound 62G
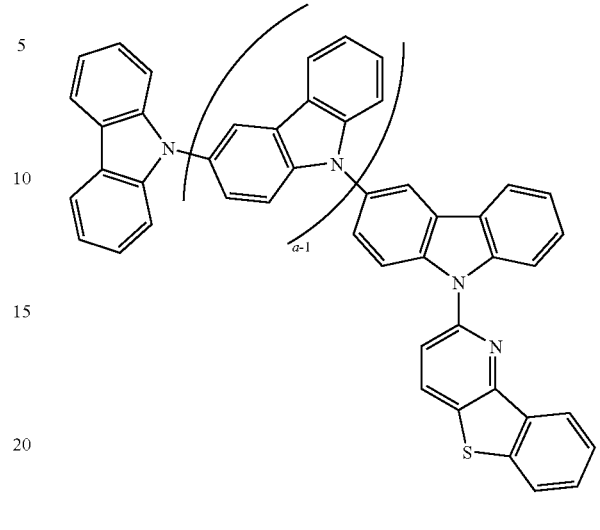
Compound 63G
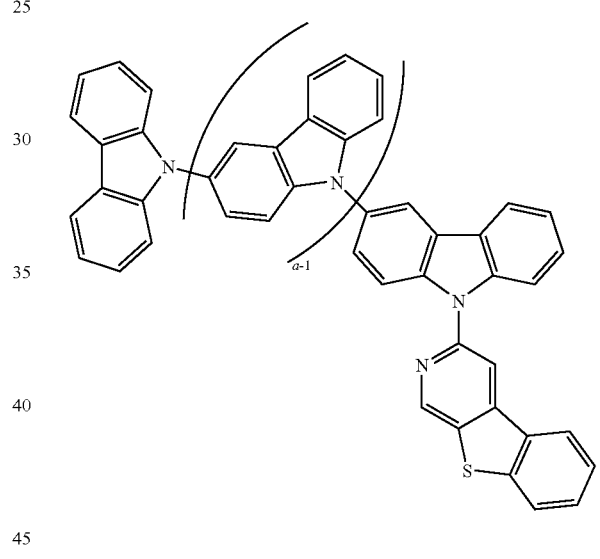
Compound 64G
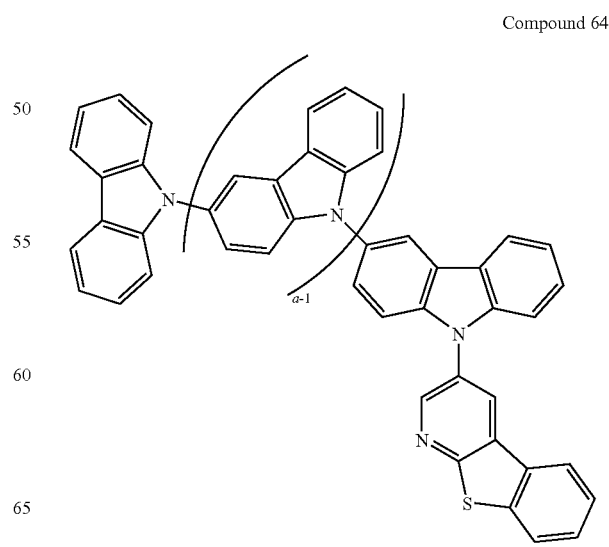

Compound 65G
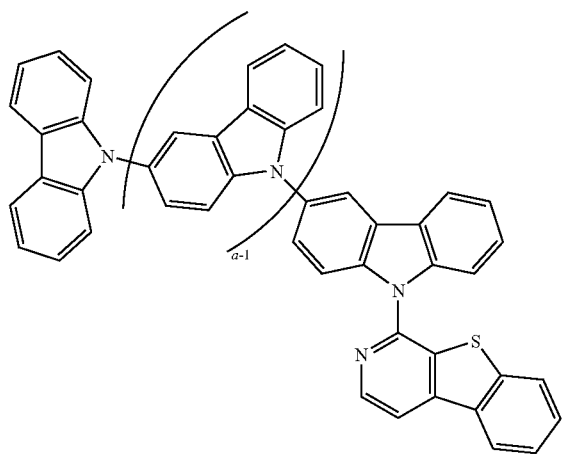
Compound 66G
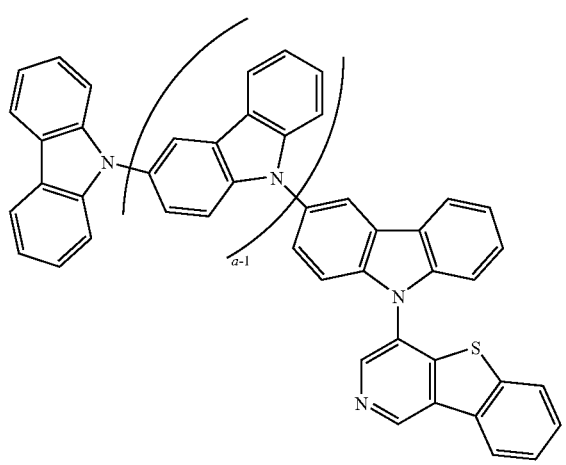
Compound 67G
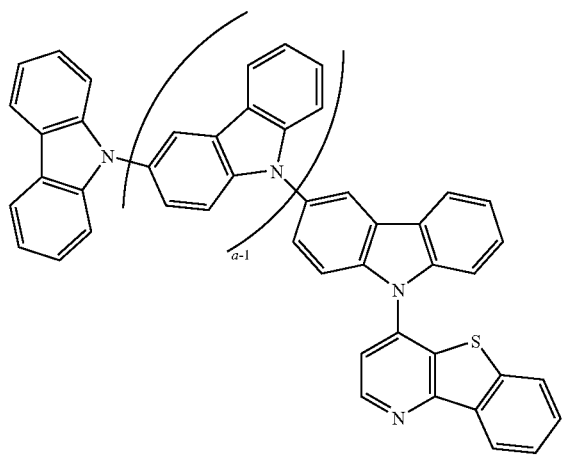
Compound 68G
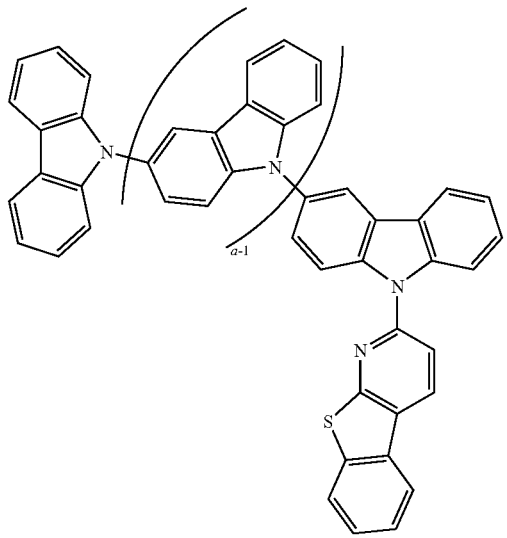
Compound 69G
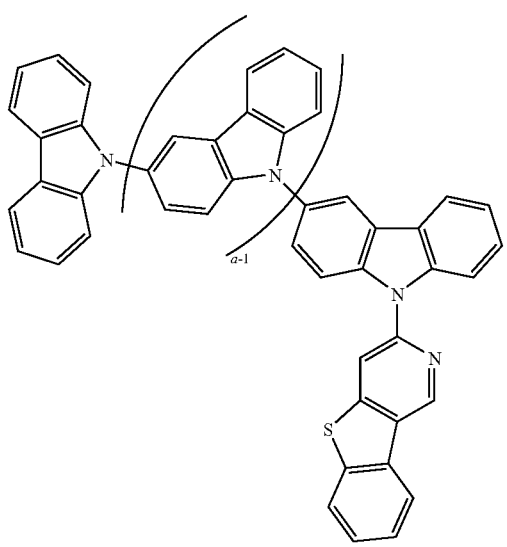
Compound 70G
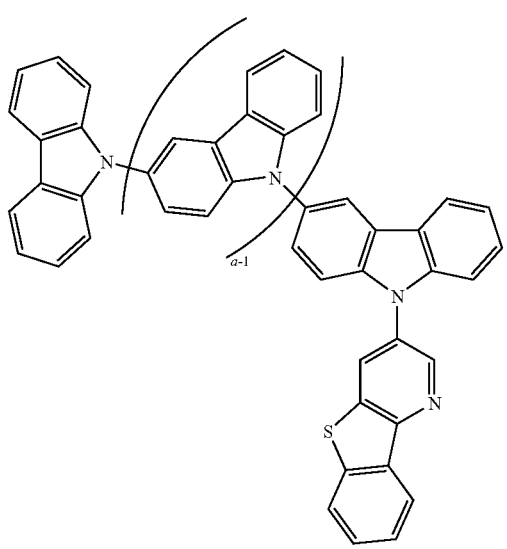

Compound 71G
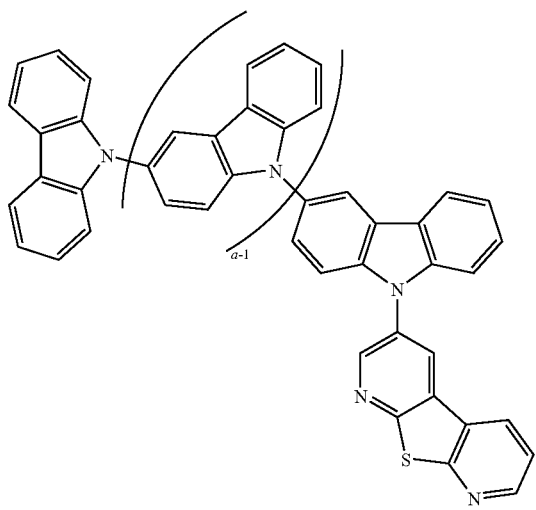
Compound 72G
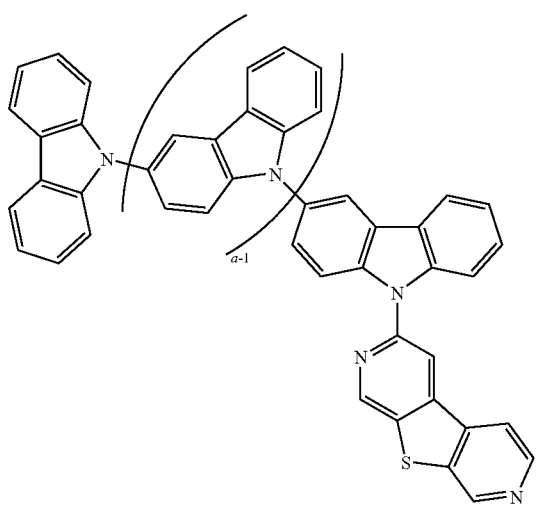
Compound 73G
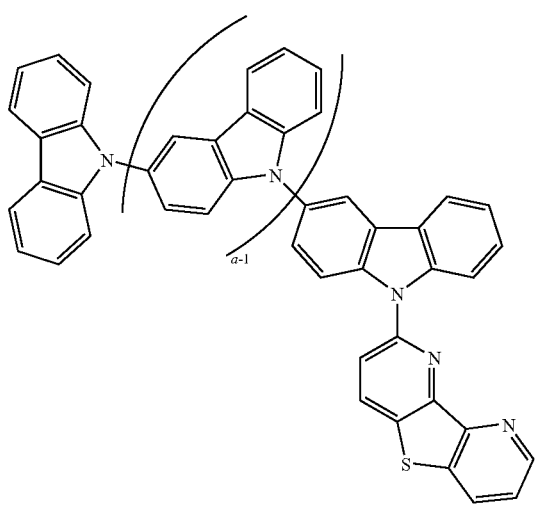
Compound 74G
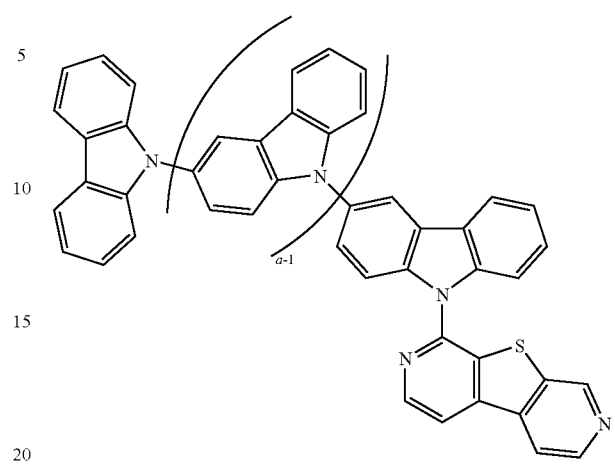
Compound 75G
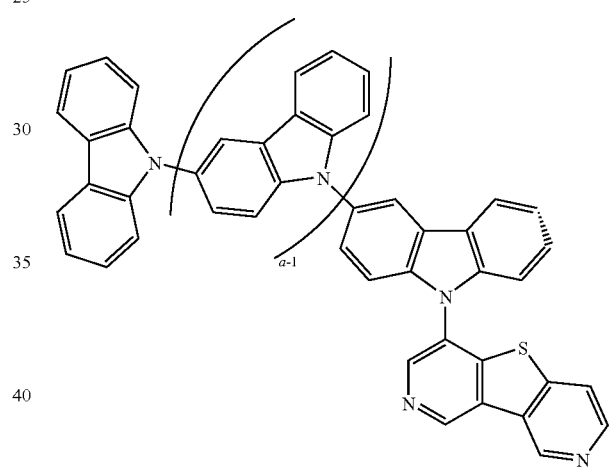
Compound 76G
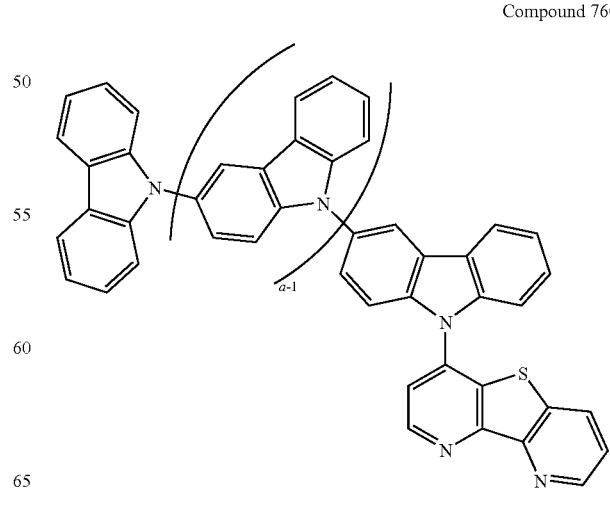

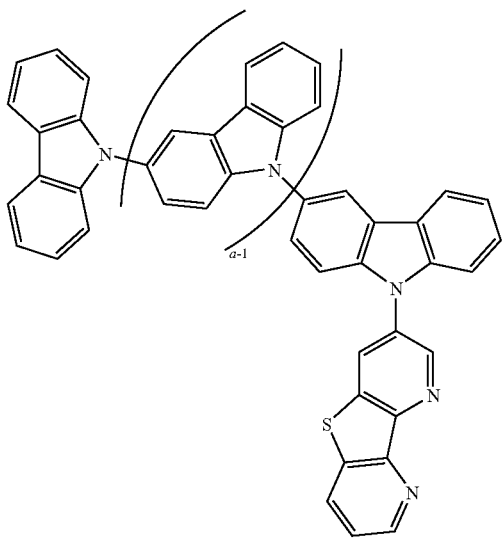

Compound 77G

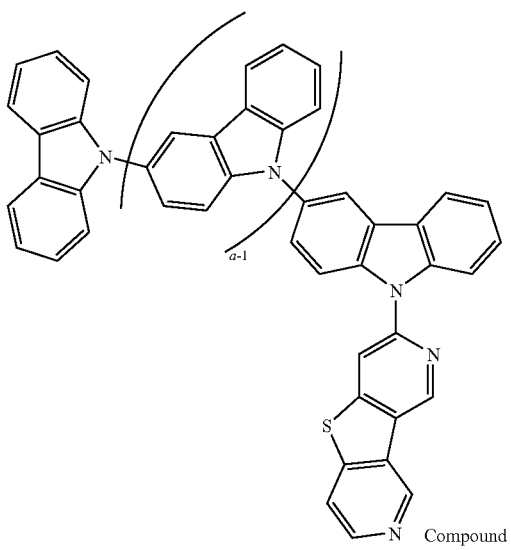

Compound 78G

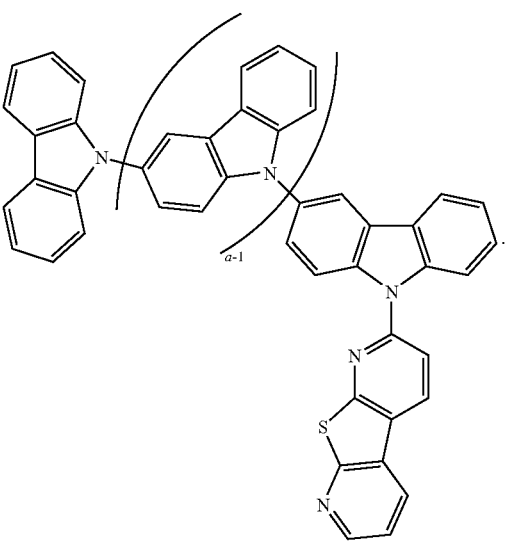

Compound 79G

Additionally, an organic light emitting device is provided. The device comprises an anode, a cathode, and a first organic layer disposed between the anode and the cathode, wherein the first organic layer comprises a carbazole-containing compound having FORMULA I. Specific examples of carbazole-containing compounds for use in such a device include a compound selected from the group consisting of Compound 1G-Compound 79G. In one aspect, the first organic layer is an emissive layer and the carbazole-containing compound is a host in the first organic layer.

The device may contain 10-100 wt % of the carbazole-containing compound in an organic layer. As discussed above, the carbazole-containing compound may be used in several organic layers of the device, including but not limited to an emissive layer, a blocking layer, and a transport layer. Preferably, the carbazole-containing compound is present in an emissive layer at a concentration of 40-99.9 wt %. The carbazole-containing compound may be used as a host or a co-host in the emissive layer of a device. In addition to the carbazole-containing compound, the emissive layer may further comprise a phosphorescent emitter having a concentration of 0.1-30 wt %.

In one aspect, the emissive layer further comprises a phosphorescent emitter. In another aspect, the phosphorescent emitter is an iridium complex having the formula:

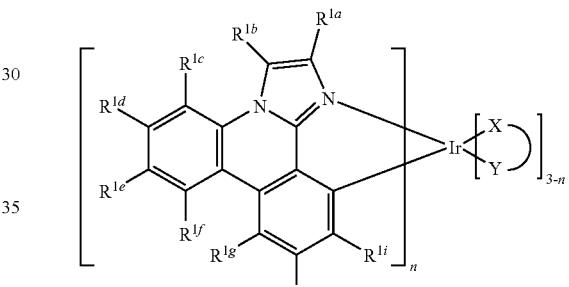

wherein n=1, 2 or 3; wherein $R^{1a}$, $R^{1b}$, $R^{1c}$, $R^{1d}$, $R^{1e}$, $R^{1f}$, $R^{1g}$, $R^{1h}$, and $R^{1i}$ are each, independently, H, hydrocarbyl, heteroatom substituted hydrocarbyl, cyano, fluoro, $OR^{2a}$, $SR^{2a}$, $NR^{2a}R^{2b}$, $BR^{2a}R^{2b}$, or $SiR^{2a}R^{2b}R^{2c}$, wherein $R^{2a-c}$ are each, independently, hydrocarbyl or heteroatom substituted hydrocarbyl, and wherein any two of $R^{1a-i}$ and $R^{2a-c}$ may be linked to form a saturated or unsaturated, aromatic or non-aromatic ring; and wherein X-Y is an ancillary ligand. Many of these phosphorescent emitters have narrow phosphorescent emission lineshapes, high triplet energy, or both. Devices including these phosphorescent emitters may have improved spectral lineshapes and lifetimes.

In yet another aspect, the phosphorescent emitter is a compound comprising a phosphorescent metal complex comprising a monoanionic, bidentate ligand having the formula:

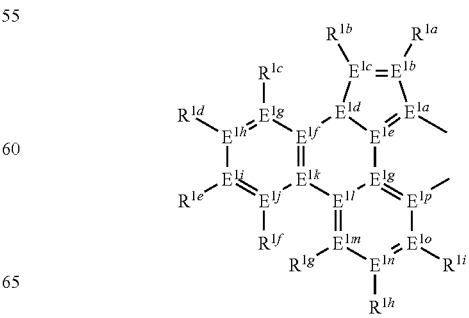

wherein $E^{1a-q}$ are selected from the group consisting of C and N and collectively comprise an 18 pi-electron system; provided that $E^{1a}$ and $E^{1p}$ are different; wherein $R^{1a-i}$ are each, independently, H, hydrocarbyl, heteroatom substituted hydrocarbyl, cyano, fluoro, $OR^{2a}$, $SR^{2a}$, $NR^{2a}R^{2b}$, $BR^{2a}R^{2b}$, or $SiR^{2a}R^{2b}R^{2c}$, where $R^{2a-c}$ are each, independently, hydrocarbyl or heteroatom substituted hydrocarbyl, and where any two of $R^{1a-i}$ and $R^{2a-c}$ may be linked to form a saturated or unsaturated, aromatic or non-aromatic ring; provided that $R^{1a-i}$ is other than H when attached to N; wherein the metal is selected from the group consisting of the non-radioactive metals with atomic numbers greater than 40; and wherein the bidentate ligand may be linked with other ligands to comprise a tridentate, tetradentate, pentadentate or hexadentate ligand. Many of these phosphorescent emitters also have good properties and when used in devices result in devices with beneficial properties.

Moreover, the device may further comprise a second layer that is a non-emissive layer. Any layer included in the device that does not emit light may herein be referred to as a "non-emissive layer." In one aspect, the first organic layer is adjacent to the second organic layer.

As discussed above, the carbazole-containing compounds described herein may be advantageously used as a host material in an emissive layer. However, the carbazole-containing compounds may also have blocking properties, impeding properties, and transport properties for both holes and electrons depending upon the relative energy and relative mobility. Therefore, these compounds may be useful as materials in different organic layers at different positions within the device.

The carbazole-containing compounds disclosed herein may be used in red, green and blue devices of which first emission energy is around 570 nm to 670 nm, 495 nm to 570 nm, and 425 nm to 495 nm, respectively. Preferably, first energy emission is around 610 nm to 630 nm, 510 nm to 530 nm, and 440 nm to 480 nm for red, green and blue devices, respectively. For a particular dopant, the triplet energy of the host is normally required to be 30 nm higher than that of the dopant in order not to cause any quench.

In one aspect, compounds well-suited for use with devices having a phosphorescent emitter having a triplet energy of 495 nm to 570 nm are provided. For these compounds, X is selected from the group consisting of biphenyl, terphenyl, triphenylene, phenanthrene, fluorene, dibenzothiophene, dibenzofuran, pyridine, pyridazine, pyrimidine, pyrazine, triazine, benzimidazole, benzothiazole, quinoline, isoquinoline, benzofuropyridine, furodipyridine, benzothienopyridine, and thienodipyridine and R is selected from the group consisting of hydrogen, alkyl, benzene, biphenyl, terphenyl, triphenylene, phenanthrene, fluorene, dibenzothiophene, dibenzofuran, pyridine, pyridazine, pyrimidine, pyrazine, triazine, benzimidazole, benzothiazole, quinoline, isoquinoline, benzofuropyridine, furodipyridine, benzothienopyridine, and thienodipyridine. Preferably, the emitter of such a device has a triplet energy of 510 nm to 530 nm. Carbazole-containing compounds having X and R are selected from the above groups may readily be used with red devices as well.

In another aspect, compounds well-suited for use with devices having a phosphorescent emitter having a triplet energy of 425 nm to 495 nm are provided. For these compounds, X is selected from the group consisting of dibenzothiophene, dibenzofuran, benzofuropyridine, furodipyridine, benzothienopyridine, and thienodipyridine and R is selected from the group consisting of hydrogen, alkyl, benzene, biphenyl, terphenyl, dibenzothiophene, and dibenzofuran. Preferably, the emitter of such a device has a triplet energy of 440 nm to 480 nm. Carbazole-containing compounds having X and R selected from the above groups may readily be used with green and red devices as well.

A consumer product comprising a device is also provided, wherein the device further comprises an anode, a cathode and an organic layer. The organic layer further comprises a carbazole-containing compound having FORMULA I.

A method of fabricating an organic light emitting device is also provided, wherein the method comprises providing a first electrode, co-depositing a host and a phosphorescent emitter to form an emissive layer wherein the emissive layer comprises a carbazole-containing compound having FORMULA I, and depositing a second electrode. In one aspect, the first electrode is an anode and the second electrode is a cathode. An organic layer may be deposited after the first electrode and before the emissive layer, and the organic layer may be an hole transport layer.

The materials described herein as useful for a particular layer in an organic light emitting device may be used in combination with a wide variety of other materials present in the device. For example, emissive dopants disclosed herein may be used in conjunction with a wide variety of hosts, transport layers, blocking layers, injection layers, electrodes and other layers that may be present. The materials described or referred to below are non-limiting examples of materials that may be useful in combination with the compounds disclosed herein, and one of skill in the art can readily consult the literature to identify other materials that may be useful in combination.

In addition to and/or in combination with the materials disclosed herein, many hole injection materials, hole transporting materials, host materials, dopant materials, exiton/hole blocking layer materials, electron transporting and electron injecting materials may be used in an OLED. Non-limiting examples of the materials that may be used in an OLED in combination with materials disclosed herein are listed in Table 1 below. Table 1 lists non-limiting classes of materials, non-limiting examples of compounds for each class, and references that disclose the materials.

TABLE 1

| MATERIAL | EXAMPLES OF MATERIAL | PUBLICATIONS |
| --- | --- | --- |
| Hole injection materials | | |
| Phthalocyanine and porphryin compounds | [Cu phthalocyanine structure] | Appl. Phys. Lett. 69, 2160 (1996) |
| Starburst triarylamines | [starburst triarylamine structure] | J. Lumin. 72-74, 985 (1997) |
| CF$_x$ Fluorohydrocarbon polymer | $-\!\!+\!\!CH_xF_y\!\!+\!\!_n$ | Appl. Phys. Lett. 78, 673 (2001) |
| Conducting polymers (e.g., PEDOT:PSS, polyaniline, polypthiophene) | [PEDOT + PSS structure] | Synth. Met. 87, 171 (1997) |
| Arylamines complexed with metal oxides such as molybdenum and tungsten oxides | [arylamine structure] + MoO$_x$ | SID Symposium Digest, 37, 923 (2006) |

TABLE 1-continued
| MATERIAL | EXAMPLES OF MATERIAL | PUBLICATIONS |
| --- | --- | --- |
| Hole transporting materials | | |
| Triarylamines (e.g., TPD, α-NPD) | 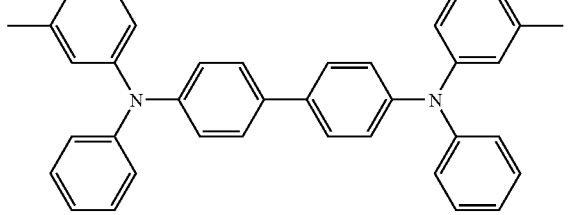 | Appl. Phys. Lett. 51, 913 (1987) |
| | 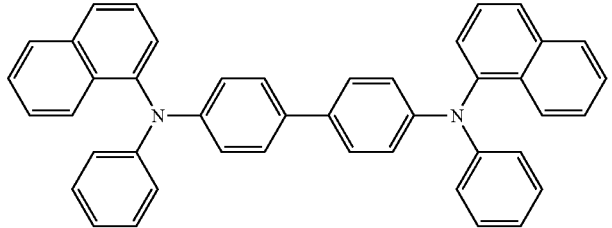 | U.S. Pat. No. 5,061,569 |
| | 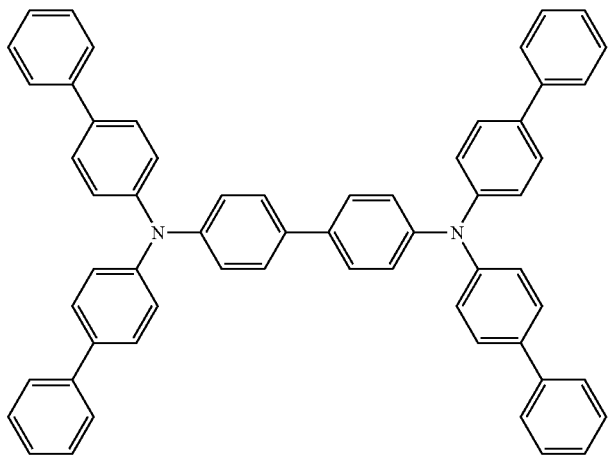 | EP650955 |
| | 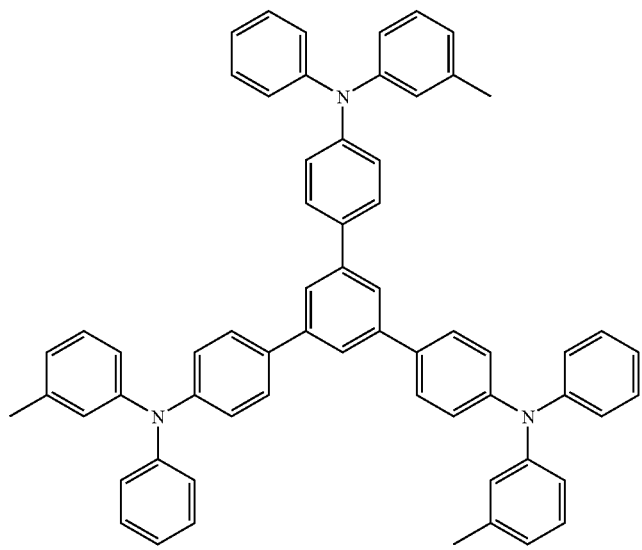 | J. Mater. Chem. 3, 319 (1993) |

TABLE 1-continued
| MATERIAL | EXAMPLES OF MATERIAL | PUBLICATIONS |
|---|---|---|
| | 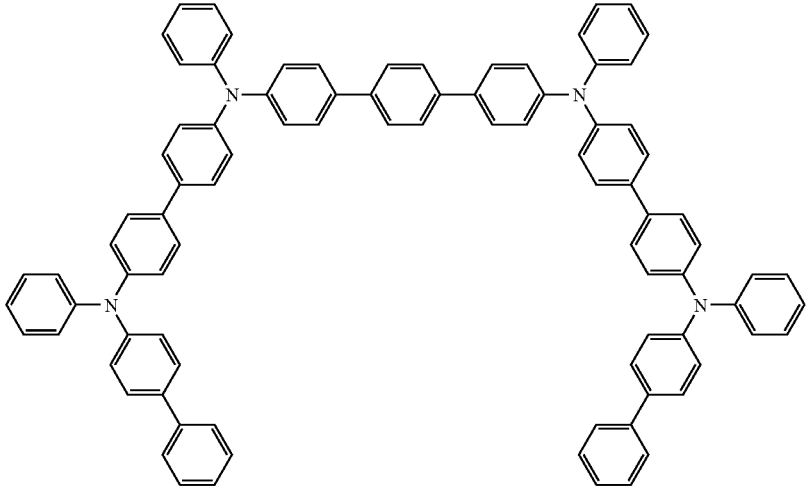 | Appl. Phys. Lett. 90, 183503 (2007) |
| | 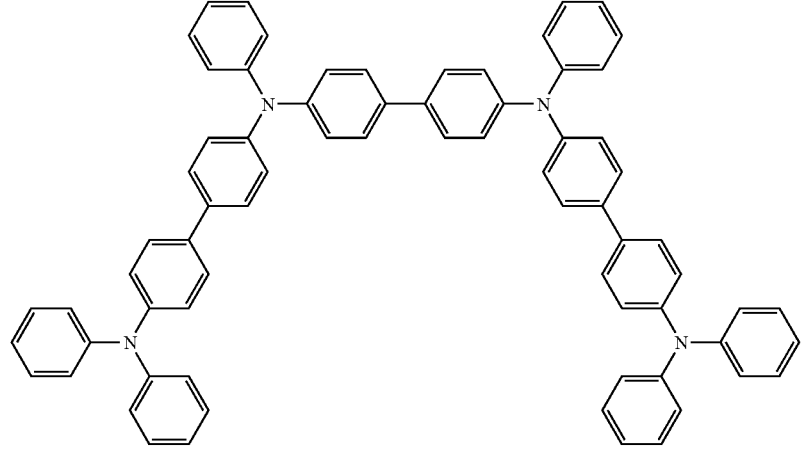 | Appl. Phys. Lett. 90, 183503 (2007) |
| Triaylamine on spirofluorene core | 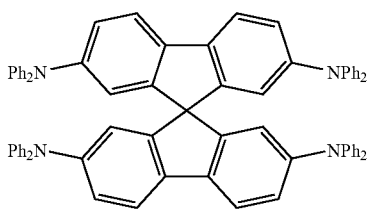 | Synth. Met. 91, 209 (1997) |

TABLE 1-continued

| MATERIAL | EXAMPLES OF MATERIAL | PUBLICATIONS |
|---|---|---|
| Arylamine carbazole compounds | | Adv. Mater. 6, 677 (1994) |
| Indolocarbazoles | | Synth. Met. 111, 421 (2000) |
| Isoindole compounds | | Chem. Mater. 15, 3148 (2003) |

TABLE 1-continued
| MATERIAL | EXAMPLES OF MATERIAL | PUBLICATIONS |
|---|---|---|
| Phosphorescent OLED host materials | | |
| Red hosts | | |
| Arylcarbazoles | 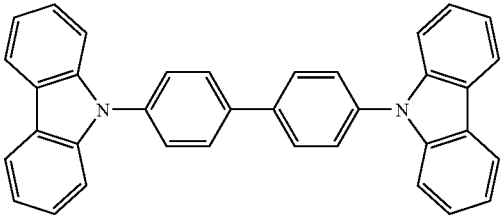 | Appl. Phys. Lett. 78, 1622 (2001) |
| Metal 8-hydroxy-quinolates (e.g., Alq$_3$, BAlq) | 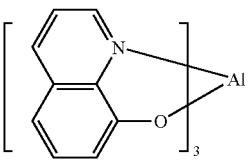 | Nature 395, 151 (1998) |
| | 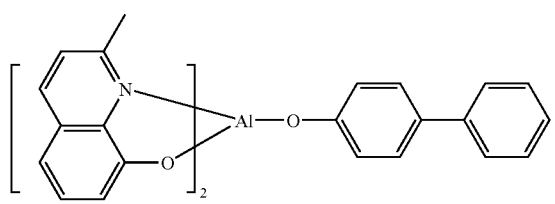 | US20060202194 |
| | 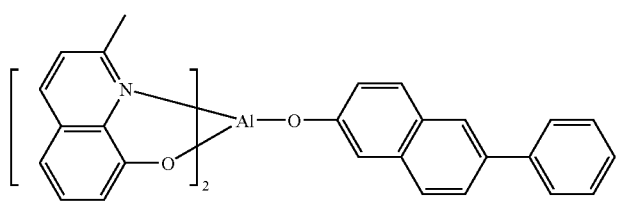 | WO2005014551 |
| Metal phenoxybenzothiazole compounds | 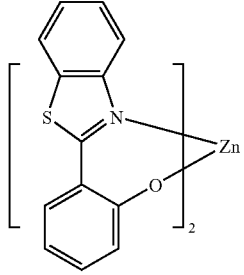 | Appl. Phys. Lett. 90, 123509 (2007) |
| Conjugated oligomers and polymers (e.g., polyfluorene) | 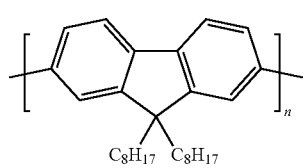 | Org. Electron. 1, 15 (2000) |

TABLE 1-continued
| MATERIAL | EXAMPLES OF MATERIAL | PUBLICATIONS |
| --- | --- | --- |
| Green hosts | | |
| Arylcarbazoles | 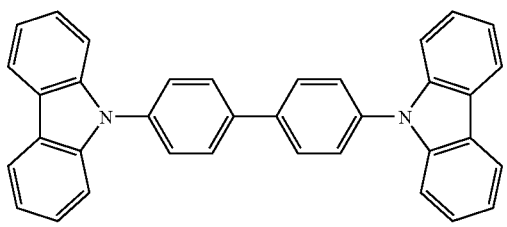 | Appl. Phys. Lett. 78, 1622 (2001) |
| | 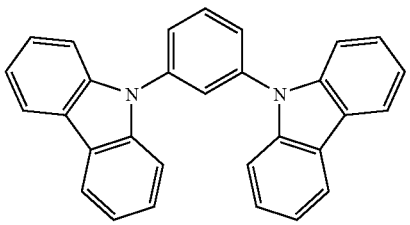 | US2003175553 |
| | 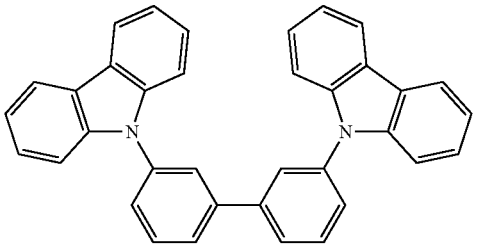 | WO2001039234 |
| Aryltriphenylene compounds | 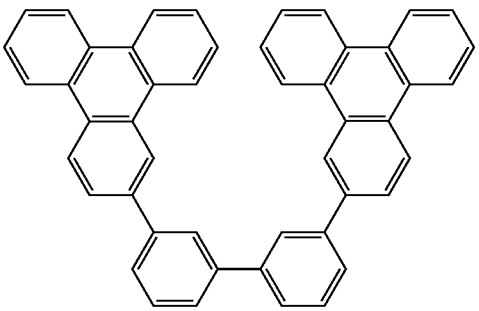 | US20060280965 |
| | 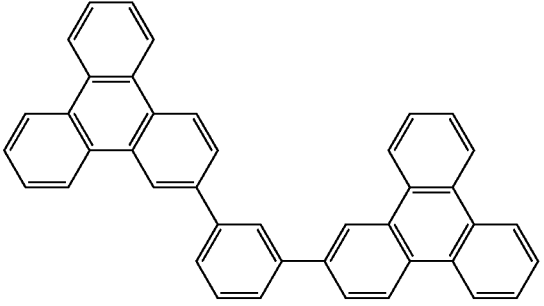 | US20060280965 |
| Polymers (e.g., PVK) | 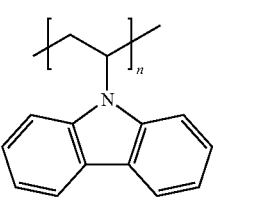 | Appl. Phys. Lett. 77, 2280 (2000) |

TABLE 1-continued
| MATERIAL | EXAMPLES OF MATERIAL | PUBLICATIONS |
|---|---|---|
| Spirofluorene compounds | 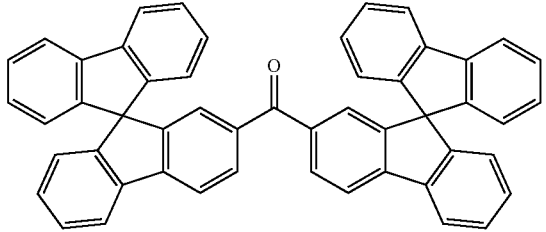 | WO2004093207 |
| Metal phenoxybenzooxazole compounds | 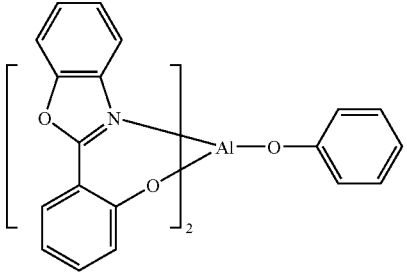 | WO05089025 |
| | 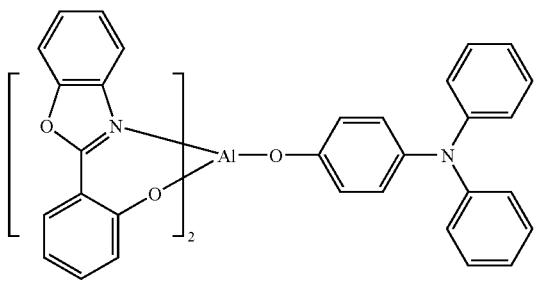 | WO06132173 |
| | 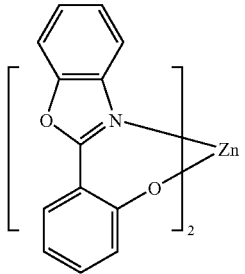 | JP200511610 |
| Spirofluorene-carbazole compounds | 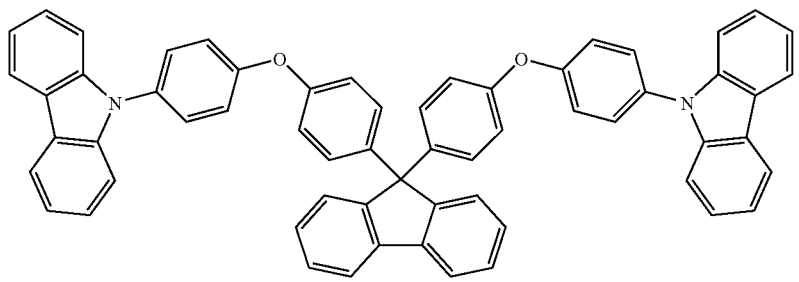 | JP2007254297 |

TABLE 1-continued
| MATERIAL | EXAMPLES OF MATERIAL | PUBLICATIONS |
|---|---|---|
| | 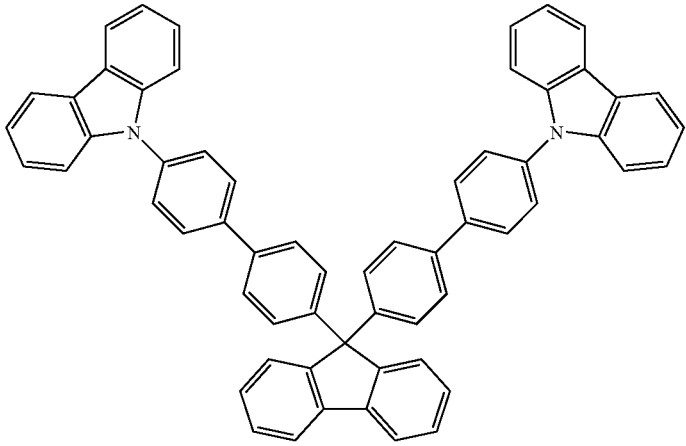 | JP2007254297 |
| Indolocabazoles | 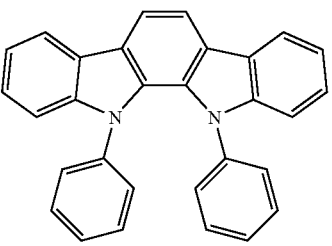 | WO07063796 |
| | 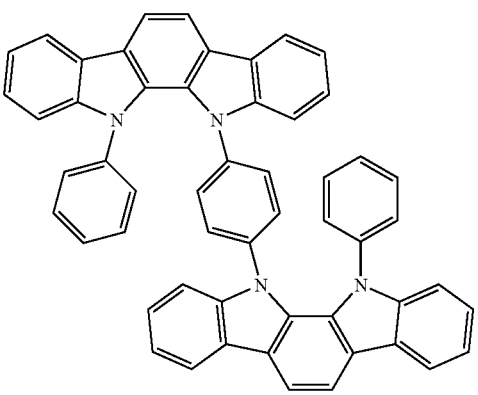 | WO07063754 |
| 5-member ring electron deficient heterocycles (e.g., triazole, oxadiazole) | 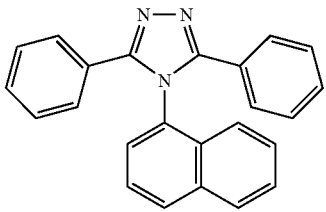 | J. Appl. Phys. 90, 5048 (2001) |
| | 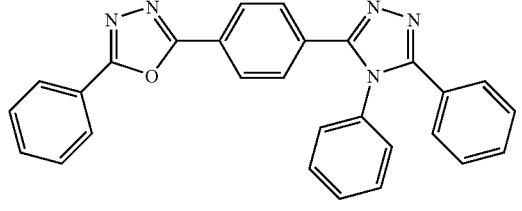 | WO04107822 |

TABLE 1-continued

| MATERIAL | EXAMPLES OF MATERIAL | PUBLICATIONS |
| --- | --- | --- |
| Metal phenoxypyridine compounds | | WO05030900 |
| Blue hosts | | |
| Arylcarbazoles | | Appl. Phys. Lett. 82, 2422 (2003) |
| | | US20070190359 |
| Dibenzothiophene-carbazole compounds | | WO2006114966 |
| Phosphorescent dopants | | |
| Red dopants | | |
| Heavy metal porphyrins (e.g., PtOEP) | | Nature 395, 151 (1998) |

TABLE 1-continued

| MATERIAL | EXAMPLES OF MATERIAL | PUBLICATIONS |
| --- | --- | --- |
| Iridium(III) organometallic complexes | | Appl. Phys. Lett. 78, 1622 (2001) |
| | | US06835469 |
| | | US06835469 |
| | | US20060202194 |
| | | US20060202194 |

| MATERIAL | EXAMPLES OF MATERIAL | PUBLICATIONS |
|---|---|---|
| | 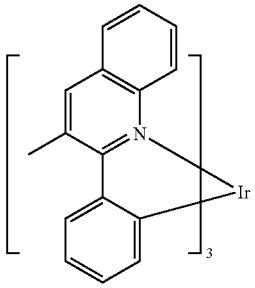 | US07087321 |
| | 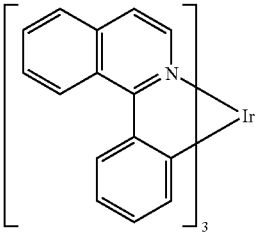 | US07087321 |
| | 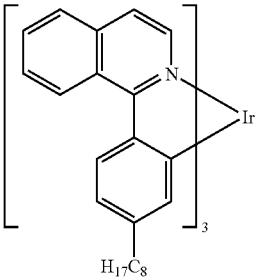 | Adv. Mater. 19, 739 (2007) |
| Platinum(II) organometallic complexes | 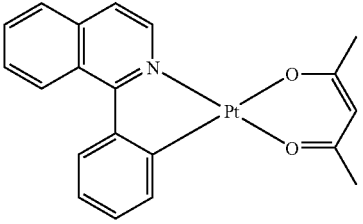 | WO2003040257 |
| Osminum(III) complexes | 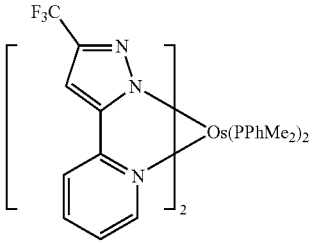 | Chem. Mater. 17, 3532 (2005) |
| Ruthenium(II) complexes | 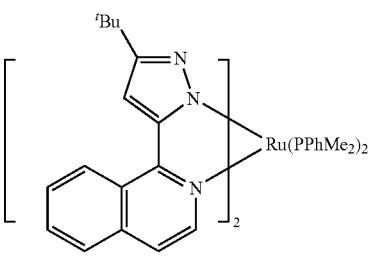 | Adv. Mater. 17, 1059 (2005) |

TABLE 1-continued
| MATERIAL | EXAMPLES OF MATERIAL | PUBLICATIONS |
|---|---|---|
| Green dopants | | |
| Iridium(III) organometallic complexes | 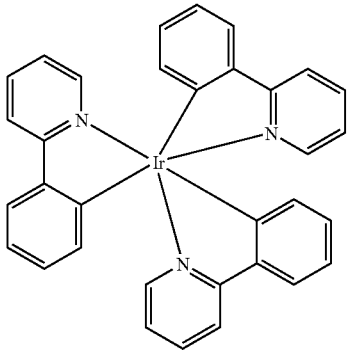<br>and its derivatives | Inorg. Chem. 40, 1704 (2001) |
| | 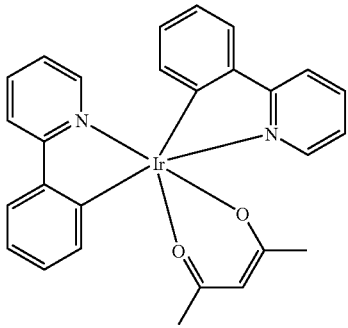 | US2002034656 |
| | 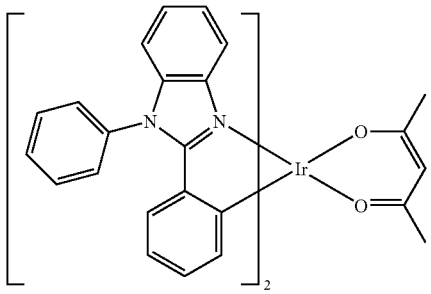 | US06687266 |
| | 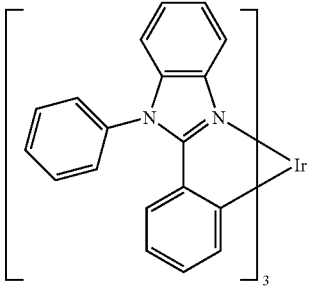 | Chem. Mater. 16, 2480 (2004) |

TABLE 1-continued

| MATERIAL | EXAMPLES OF MATERIAL | PUBLICATIONS |
|---|---|---|
| | | US2007190359 |
| | | US2006008670<br>JP2007123392 |
| | | Adv. Mater. 16, 2003 (2004) |
| | | Angew. Chem. Int. Ed. 2006, 45, 7800 |
| Pt(II) organometallic complexes | | Appl. Phys. Lett. 86, 153505 (2005) |

| MATERIAL | EXAMPLES OF MATERIAL | PUBLICATIONS |
|---|---|---|
| | 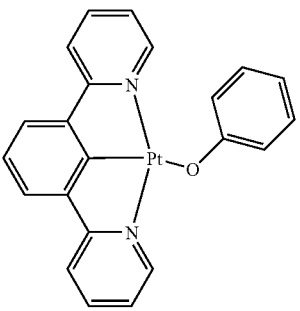 | Appl. Phys. Lett. 86, 153505 (2005) |
| | 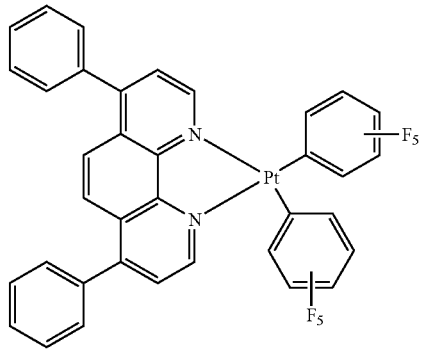 | Chem. Lett. 34, 592 (2005) |
| Gold complexes | 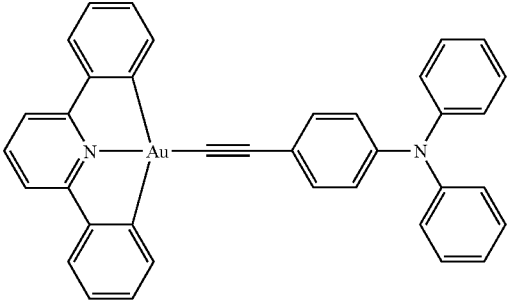 | Chem. Commun. 2906 (2005) |
| Rhenium(III) complexes | 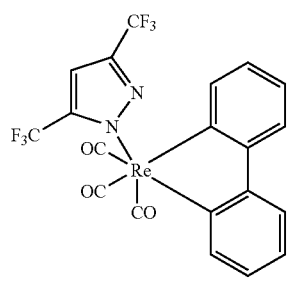 | Inorg. Chem. 42, 1248 (2003) |
| Blue dopants | | |
| Iridium(III) organometallic complexes | 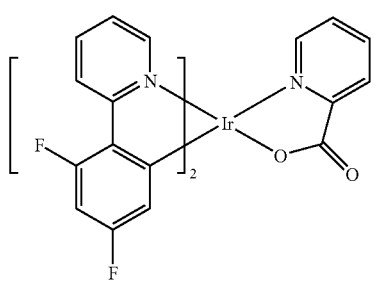 | WO2002002714 |

TABLE 1-continued
| MATERIAL | EXAMPLES OF MATERIAL | PUBLICATIONS |
|---|---|---|
| | 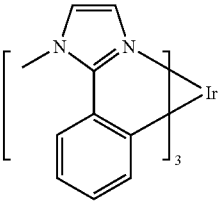 | WO2006009024 |
| | 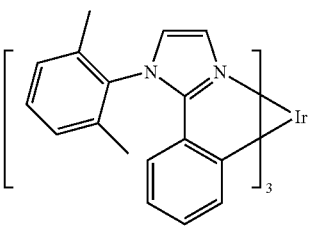 | US2006251923 |
| | 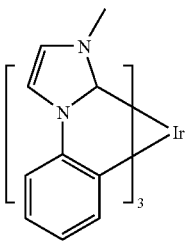 | WO2006056418, US2005260441 |
| | 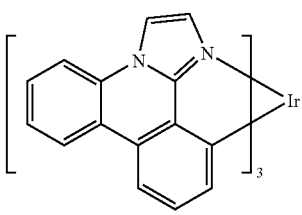 | US2007190359 |
| | 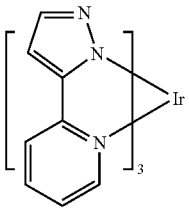 | US2002134984 |
| | 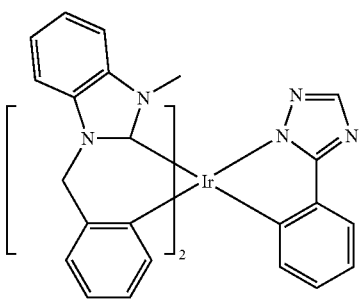 | Angew. Chem. Int. Ed. 47, 1 (2008) |

TABLE 1-continued

| MATERIAL | EXAMPLES OF MATERIAL | PUBLICATIONS |
|---|---|---|
| | | Chem. Mater. 18, 5119 (2006) |
| | | Inorg. Chem. 46, 4308 (2007) |
| | | WO05123873 |
| | | WO05123873 |
| | | WO07004380 |

TABLE 1-continued
| MATERIAL | EXAMPLES OF MATERIAL | PUBLICATIONS |
|---|---|---|
| | 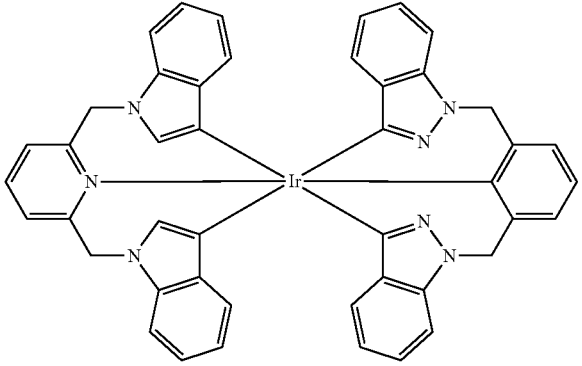 | WO06082742 |
| Osmium(II) complexes | 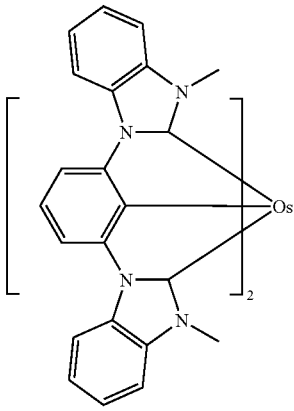 | US2005260449 |
| | 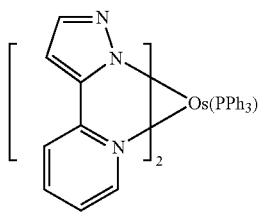 | Organometallics 23, 3745 (2004) |
| Gold complexes | 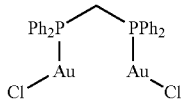 | Appl. Phys. Lett. 74, 1361 (1999) |
| Platinum(II) complexes | 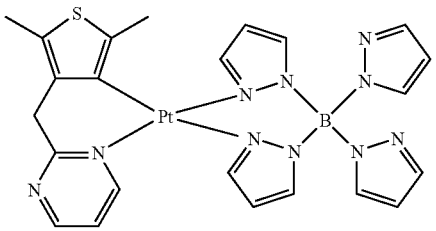 | WO06098120, WO06103874 |

TABLE 1-continued

| MATERIAL | EXAMPLES OF MATERIAL | PUBLICATIONS |
|---|---|---|
| Exciton/hole blocking layer materials | | |
| Bathocuprine compounds (e.g., BCP, BPhen) | 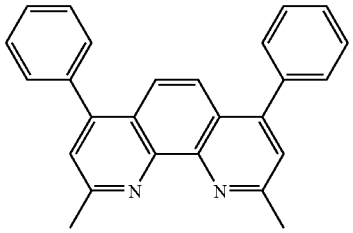 | Appl. Phys. Lett. 75, 4 (1999) |
| | 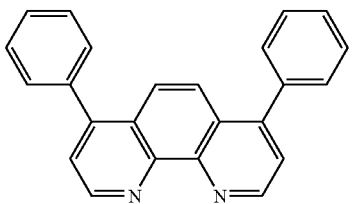 | Appl. Phys. Lett. 79, 449 (2001) |
| Metal 8-hydroxy-quinolates (e.g., BAlq) | 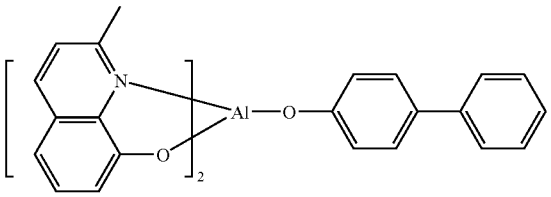 | Appl. Phys. Lett. 81, 162 (2002) |
| 5-member ring electron deficient heterocycles such as triazole, oxadiazole, imidazole, benzoimidazole | 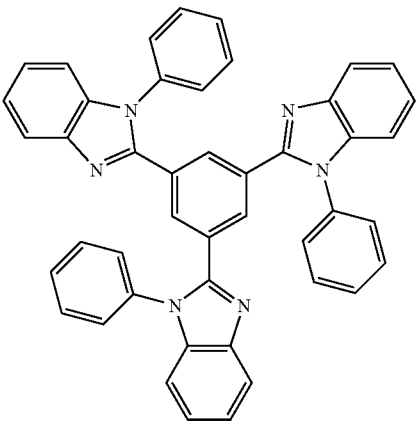 | Appl. Phys. Lett. 81, 162 (2002) |
| Triphenylene compounds | 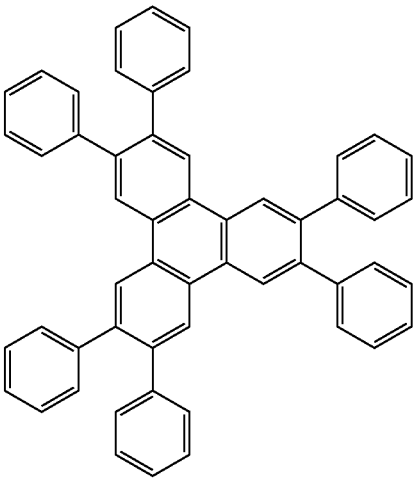 | US20050025993 |

TABLE 1-continued

| MATERIAL | EXAMPLES OF MATERIAL | PUBLICATIONS |
| --- | --- | --- |
| Fluorinated aromatic compounds | | Appl. Phys. Lett. 79, 156 (2001) |
| Electron transporting materials | | |
| Anthracene-benzoimidazole compounds | | WO03060956 |
| Anthracene-benzoimidazole compounds | | Appl. Phys. Lett. 89, 063504 (2006) |
| Metal 8-hydroxy-quinolates (e.g., $Alq_3$) | | Appl. Phys. Lett. 51, 913 (1987) |

TABLE 1-continued

| MATERIAL | EXAMPLES OF MATERIAL | PUBLICATIONS |
| --- | --- | --- |
| Metal hydroxy-benoquinolates | | Chem. Lett. 5, 905 (1993) |
| Bathocuprine compounds such as BCP, BPhen, etc | | Appl. Phys. Lett. 91, 263503 (2007) |
| | | Appl. Phys. Lett. 79, 449 (2001) |
| 5-member ring electron deficient heterocycles (e.g., triazole, oxadiazole. imidazole. benzoimidazole) | | Appl. Phys. Lett. 74, 865 (1999) |
| | | Appl. Phys. Lett. 55, 1489 (1989) |
| | | Jpn. J. Apply. Phys. 32, L917 (1993) |

TABLE 1-continued

| MATERIAL | EXAMPLES OF MATERIAL | PUBLICATIONS |
|---|---|---|
| Silole compounds | | Org. Electron. 4, 113 (2003) |
| Arylborane compounds | | J. Am. Chem. Soc. 120, 9714 (1998) |
| Fluorinated aromatic compounds | | J. Am. Chem. Soc. 122, 1832 (2000) |

EXPERIMENTAL

Compound Examples

Some of the carbazole-containing compounds were synthesized as follows:

Compound 8

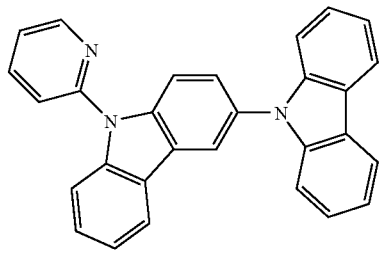

Compound 8

Step 1. Solid KI (22.1 g, 133 mmol) was add into carbazole (33.4 g, 200 mmol) in 550 mL of acetic acid. The mixture became clear after it was heated up to 120° C. for 30 min. After it was cooled back to 100° C., $KIO_3$ (21.4 g, 100 mmol) was added portion-wise. The mixture was stirred at this temperature for another 2 hours. After the mixture cooled down, 500 mL of water was added to precipitate out all the product. The solid was filtered, and washed with hot water. The crude product was recrystallized from $CH_2Cl_2$ once, and then from EtOAc/hexanes to give 24 g pure 3-iodocarbazole.

Step 2. Tosyl chloride (8.4 g, 44 mmol) was added to a solution of 3-iodocarbazole (11.7 g, 40 mmol) and grounded KOH (2.7 g, 48 mmol) in 200 mL of acetone. The mixture was refluxed for 3 hours, and then cooled down. It was poured into 1 L of cold water while stirring. After sitting for 30 minutes, the liquid was decanted. The crude product was thus obtained as sticky solid on the beaker wall. About 11 g of pure 3-iodo-9-tosylcarbazole was obtained after recrystallization from $CH_2Cl_2$/EtOH.

Step 3. 3-iodo-9-tosylcarbazole (10.6 g, 24 mmol), carbazole (4.8 g, 29 mmol), CuI (0.4 g, 2.0 mmol), trans-1,2-Diaminocyclohexane (0.3 g, 2.4 mmol), potassium phosphate tribasic (10.6 g, 50 mmol), and 150 mL of toluene were added to a 500 mL round flask. The reaction was heated to reflux, and stirred under a nitrogen atmosphere for 24 hours. After cooling, the mixture was purified by a silica gel column. The yield of 3-(9-carbazolyl)-9-tosylcarbazole was 10 g.

Step 4. 3-(9-carbazolyl)-9-tosylcarbazole (10.0 g, 21 mmol), NaOH (8.0 g, 200 mmol), 80 mL of THF, 40 mL of MeOH and 40 mL of water were added to a 500 mL round flask. The reaction was heated to reflux for 12 hours. After cooling, the mixture was purified by a silica gel column. The yield of 3-(9-carbazolyl)carbazole was 8 g.

Step 5. 3-(9-carbazolyl)carbazole (3.0 g, 9 mmol), 2-bromopyridine (1.9 g, 12 mmol), CuI (0.2 g, 1.0 mmol), trans-1,2-Diaminocyclohexane (0.2 g, 1.5 mmol), potassium phosphate tribasic (5.3 g, 25 mmol), and 150 mL of toluene were added to a 500 mL round flask. The reaction was heated to reflux and stirred under a nitrogen atmosphere for 24 hours. After cooling, the mixture was purified by a silica gel column. The yield was 2.2 g. The product was further purified by vacuum sublimation. $^1$H NMR results confirmed the desired compound. $E_{ox}$=0.86 V (quasi-reversible), $E_{red}$=−2.91 V (reversible) (vs. $Fc^+$/Fc, in 0.10M $Bu^n{}_4NPF_6$ solution (DMF)

Compound 15

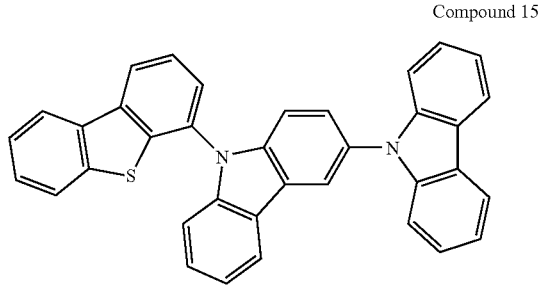

Compound 15

4-iododibenzothiophene (3.0 g, 10 mmol), 3-(9-carbazolyl)carbazole (2.3 g, 7 mmol), Pd$_2$(dba)$_3$ (0.5 g, 0.5 mmol), 2-dicyclohexylphosphino-2',6'-dimethoxybiphenyl (S-Phos, 0.8 g, 2.0 mmol), sodium t-butoxide (2.9 g, 30 mmol), and 200 mL of xylene were added to a 500 mL round flask. The reaction was heated to reflux and stirred under a nitrogen atmosphere for 24 hours. After cooling, the mixture was purified by a silica gel column. The yield was 3.0 g. The product was further purified by vacuum sublimation. $^1$H NMR results confirmed the desired compound. $E_{ox}$=0.77 V (quasi-reversible), $E_{red}$=−2.79 V (reversible) (vs. Fc$^+$/Fc, in 0.10M Bu''$_4$NPF$_6$ solution (DMF) with Pt working and auxiliary electrodes and a non-aqueous Ag/Ag$^+$ reference electrode, and scan rates varied from 50 to 5000 mVs$^{-1}$).

Compound 17 (Compound 17G where a=1)

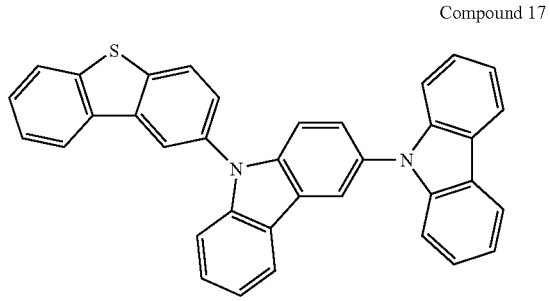

Compound 17

3-(9-carbazolyl)carbazole (2.3 g, 7 mmol), 2-bromobenzothiophene (2.8 g, 11 mmol), CuI (0.2 g, 1.0 mmol), trans-1,2-Diaminocyclohexane (0.2 g, 1.5 mmol), potassium phosphate tribasic (5.3 g, 25 mmol), and 150 mL of toluene were added to a 500 mL round flask. The reaction was heated to reflux, and stirred under a nitrogen atmosphere for 24 hours. After cooling, the mixture was purified by a silica gel column. The yield was 3.0 g. The product was further purified by vacuum sublimation. $^1$H NMR results confirmed the desired compound. $E_{ox}$=0.74 V (quasi-reversible), $E_{red}$=−2.78 V (reversible) (vs. Fc$^+$/Fc, in 0.10M Bu''$_4$NPF$_6$ solution (DMF) with Pt working and auxiliary electrodes and a non-aqueous Ag/Ag$^+$ reference electrode, and scan rates varied from 50 to 5000 mVs$^{-1}$).

Compound 17' (Compound 17G where a=2)

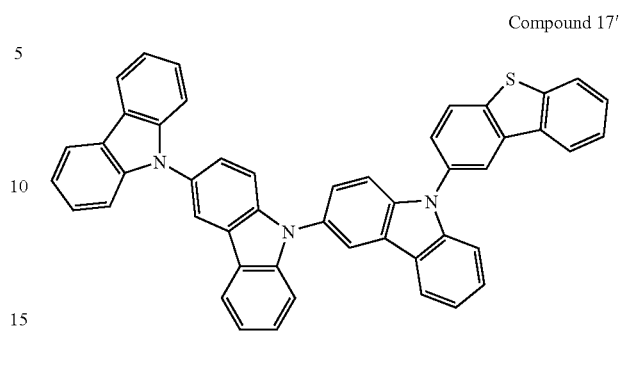

Compound 17'

Step 1. 3-(9-carbazolyl)carbazole (9.8 g, 30 mmol), 3-iodo-9-tosylcarbazole (16.1 g, 36 mmol), CuI (1.7 g, 9 mmol), trans-1,2-Diaminocyclohexane (2.1 g, 18 mmol), potassium phosphate tribasic (12.7 g, 60 mmol), and 250 mL of toluene were added to a 500 mL round flask. The reaction was heated to reflux, and stirred under a nitrogen atmosphere for 24 hours. After cooling, the mixture was purified by a silica gel column. The yield of 3-(9-(3-(9-carbazolyl)carbazolyl))-9-tosylcarbazole was 20 g. It was detosylated as described above to afford 12 g of 3-(9-(3-(9-carbazolyl)carbazolyl))carbazole.

Step 2. 3-(9-(3-(9-carbazolyl)carbazolyl))carbazole (3.0 g, 6 mmol), 2-bromobenzothiophene (2.1 g, 7.8 mmol), CuI (0.4 g, 1.8 mmol), trans-1,2-Diaminocyclohexane (0.4 g, 3.6 mmol), potassium phosphate tribasic (3.2 g, 15 mmol), and 150 mL of toluene were added to a 500 mL round flask. The reaction was heated to reflux, and stirred under a nitrogen atmosphere for 24 hours. After cooling, the mixture was purified by a silica gel column. The yield was 2.9 g. The product was further purified by vacuum sublimation. $^1$H NMR results confirmed the desired compound. $E_{ox}$=0.81 V (quasi-reversible), $E_{red}$=−2.78 V (reversible) (vs. Fc$^+$/Fc, in 0.10M Bu''$_4$NPF$_6$ solution (DMF) with Pt working and auxiliary electrodes and a non-aqueous Ag/Ag$^+$ reference electrode, and scan rates varied from 50 to 5000 mVs$^{-1}$).

Compound 16

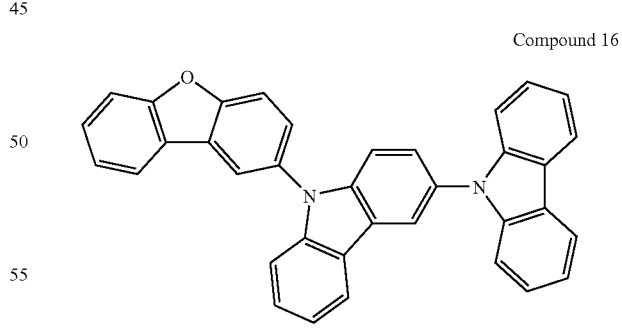

Compound 16

The 100 mL round bottom flask, equipped with magnetic stirrer and refluxed condenser, was charged with 8-iodo-3,4-dihydrodibenzo[b,d]furan (332 mg, 1 mmol), 3-(9-carbazolyl)carbazole (294 mg, 1 mmol), Pd(OAc)$_2$ (23 mg, 10 mol %), P(t-Bu)$_3$ (1 mL of 1M solution in toluene, 1 mmol), potassium tert-buthoxide (150 mg, 1.5 eq) and 100 ml of xylene. The flask was filled with nitrogen, and the reaction mixture was heated to reflux and stirred under nitrogen atmosphere for 24 hours. Then reaction was cooled down to room temperature, filtered through silica plug and evaporated. The residue was subjected to column chromatography on silica gel, eluent hexane/ethyl acetate mixture 9:1, providing 410 mg of 9-(dibenzo[b,d]furan-2-yl)-9H-3,9'-bicarbazole as white solid. The structure was confirmed by NMR and MS spectroscopy.

Compound 23

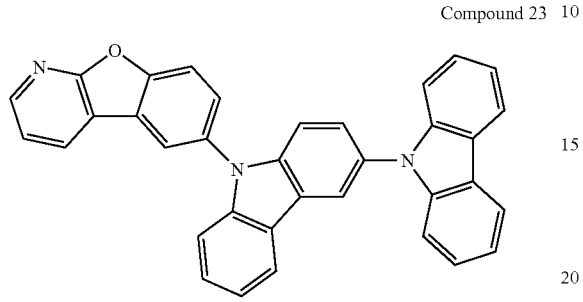

Compound 23

Step 1. The 300 mL round bottom flask, equipped with magnetic stirrer and refluxed condenser, was charged with 5-chloro-2-methoxyphenylboronic acid (5.00 g, 33 mmol), 2-amino-3-bromopyridine (5.70 g, 33 mmol), $Pd_2(dba)_3$ (604 mg, 2 mol %), 2-dicylohexylphosphino-2',6'-dimethoxybiphenyl (542 mg, 4 mol %), potassium phosphate tribasic monohydrate (22.8 mg, 3 eq) and 100 mL of toluene. The flask was filled with nitrogen, and the reaction mixture was heated to reflux and stirred under nitrogen atmosphere for 24 hours. Then reaction was cooled down to room temperature, filtered through silica plug and evaporated. The residue was subjected to column chromatography on silica gel, eluent hexane/ethyl acetate mixture 1:1, providing 5.0 g of 3-(5-chloro-2-methoxyphenyl)pyridin-2-amine as yellow solid. The structure was confirmed by NMR and MS spectroscopy.

Step 2. 3-(5-Chloro-2-methoxyphenyl)pyridin-2-amine (5.00 g, 21 mmol) was dissolved in the mixture of THF (409 mL), $HBF_4$ (50% aqueous solution, 36 mL) and 15 mL of water. The solution was cooled to −5° C., and sodium nitrite (1.70 g in 20 mL of water) was added dropwise. Reaction was kept 1 hour at −5° C., then was allowed to warm up to room temperature and stirred overnight at room temperature. Then pH of the reaction mixture was adjusted to 10, and it was extracted with ethyl acetate (4×25 mL). Organic fractions were combined, dried over sodium sulfate and evaporated. The residue was subjected to column chromatography on silica gel, eluent hexane/ethyl acetate 9/1 mixture. Chromatography product contained 3-(5-chloro-2-methoxyphenyl)-2-fluoropyridine, pure 6-chlorobenzofuro[2,3-b]pyridine (1.52 g, colorless long needles) was obtained by crystallization from hexane/ethyl acetate.

Step 3. The 300 mL round bottom flask, equipped with magnetic stirrer and refluxed condenser, was charged with 6-chlorobenzofuro[2,3-b]pyridine (2.04 g, 10 mmol), 3-(9-carbazolyl)carbazole (3.32 g, 10 mmol), $Pd(OAc)_2$ (450 mg, 20 mol %), $P(t-Bu)_3$ (10 mL of 1M solution in toluene, 10 mmol), potassium tert-buthoxide (1.92 g, 20 mmol) and 150 ml of xylene. The flask was filled with nitrogen, and the reaction mixture was heated to reflux and stirred under nitrogen atmosphere for 36 hours. Then the reaction was cooled down to room temperature, washed with water, filtered through silica plug and evaporated. The residue was subjected to column chromatography on silica gel, eluent hexane/ethyl acetate mixture 4:1, providing 3.01 g of 6-(9H-3,9'-bicarbazol-9-yl)benzofuro[2,3-b]pyridine as white solid, structure was confirmed by NMR and MS spectroscopy.

Compound 20

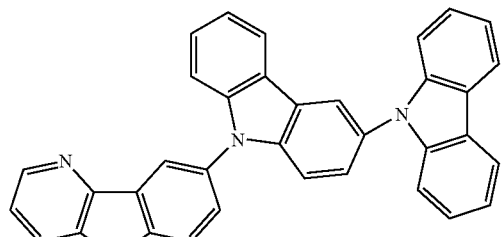

Compound 20

Step 1. The 500 mL round-bottom flask, equipped with magnetic stirrer and reflux condenser was charged with 5-chloro-2-methoxyphenylboronic acid (9.78 g, 52 mmol), 3-amino-2-chloropyridine (7.00 g, 55 mmol), 2-dicyclohexylphosphino-2',6'-dimethoxybiphenyl (S-Phos, 0.43 g, 2 mol %), palladium (II) acetate (112 mg, 1 mol %), potassium carbonate (21.7 g, 157 mmol), 180 mL of acetonitrile and 20 ml of water. The flask was filled with nitrogen and heated to reflux under nitrogen atmosphere for 24 hours. Then the reaction was cooled down to room temperature, diluted with 500 mL of water and extracted with ethyl acetate (5×40 mL). Organic fractions were combined, dried over sodium sulfate, filtered and evaporated. The residue was subjected to column chromatography on silica gel with eluent hexane/ethyl acetate gradient mixture, providing 2-(5-chloro-2-methoxyphenyl)pyridin-3-amine as white crystals (9.5 g, NMR confirmed the structure).

Step 2. The 500 mL round-bottom flask, equipped with magnetic stirrer and reflux condenser was charged with 2-(5-chloro-2-methoxyphenyl)pyridin-3-amine (9.00 g, 39 mmol), 70 mL THF, 70 mL $HBF_4$ (50% in water) and 40 mL $H_2O$. Reaction mixture was cooled to −10° C., and solution of sodium nitrite (5.6 g in 20 mL water) was added dropwise. Reaction mixture was warmed gradually to room temperature and stirred overnight. The reaction mixture was diluted with 500 mL of water and extracted with ethyl acetate (4×50 mL). Organic fractions were combined, dried over sodium sulfate and evaporated, the residue was subjected to column chromatography on silica gel with hexane/ethyl acetate 9/1 mixture, providing 8-chlorobenzofuro[3,2-b]pyridine (6.00 g, colorless needles from hexane/ethyl acetate).

Step 3. The 100 mL round bottom flask, equipped with magnetic stirrer and refluxed condenser, was charged with 8-chlorobenzofuro[3,2-b]pyridine (2.04 g, 10 mmol), 3-(9-carbazolyl)carbazole (3.32 g, 10 mmol), $Pd(OAc)_2$ (450 mg, 20 mol %), $P(t-Bu)_3$ (10 mL of 1M solution in toluene, 10 mmol), potassium tert-buthoxide (1.92 g, 1.5 eq) and 150 ml of xylene. The flask was filled with nitrogen, and the reaction mixture was heated to reflux and stirred under nitrogen atmosphere for 24 hours. Then reaction was cooled down to room temperature, filtered through silica plug and evaporated. The residue was subjected to column chromatography on silica gel, eluent hexane/ethyl acetate mixture 9:1, providing 2.5 g of 8-(9H-3,9'-bicarbazol-9-yl)benzofuro[3,2-b]pyridine as white solid. The structure was confirmed by NMR and MS spectroscopy.

Compound 50

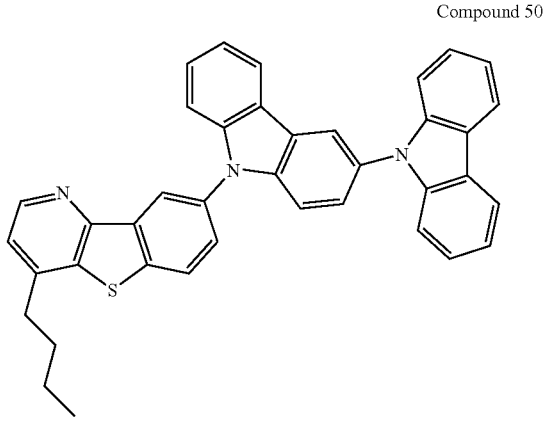

Compound 50

Step 1. The 500 mL round-bottom flask, equipped with magnetic stirrer and reflux condenser was charged with 2-(methylthio)phenylboronic acid (9.48 g, 56 mmol), 3-amino-2-bromopyridine (7.15 g, 57 mmol), 2-dicyclohexylphosphino-2',6'-dimethoxybiphenyl (S-Phos, 0.92 g, 4 mol %), $Pd_2(dba)_3$ (1.02 g, 2 mol %), potassium phosphate hydrate (39 g, 3 equivalents), 100 mL of toluene. The flask was filled with nitrogen and heated to reflux under nitrogen atmosphere for 24 hours. Then the reaction was cooled down to room temperature, diluted with 500 ml of water and extracted with ethyl acetate (5×40 mL). Organic fractions were combined, dried over sodium sulfate, filtered and evaporated. The residue was subjected to column chromatography on silica gel with eluent hexane/ethyl acetate gradient mixture, providing 2-(2-(methylthio)phenyl)pyridin-3-amine as yellow crystals (9.5 g). NMR confirmed the structure.

Step 2. The 500 mL round-bottom flask, equipped with magnetic stirrer and reflux condenser was charged with 2-(2-(methylthio)phenyl)pyridin-3-amine (8.42 g, 39 mmol), 70 mL THF, 70 mL $HBF_4$ (50% in water) and 40 mL $H_2O$. Reaction mixture was cooled to −10° C., and solution of sodium nitrite (5.6 g in 20 mL water) was added dropwise. Reaction mixture was warmed gradually to room temperature and stirred overnight. The reaction mixture was diluted with 500 mL of water and extracted with ethyl acetate (4×50 mL). Organic fractions were combined, dried over sodium sulfate and evaporated, the residue was subjected to column chromatography on silica gel with hexane/ethyl acetate 9/1 mixture, providing aza-dibenzothiophene (3.5 g, colorless needles from hexane/ethyl acetate).

Step 3. Aza-dibenzothiophene (1.78 g, 6.7 mmol) was dissolved in 75 mL of dry THF and solution was cooled in $CO_2$/acetone bath. n-Butyl lithium (7 mL of 1.6 M solution in hexane) was added dropwise, color of the reaction mixture turned orange, the solution of 2.6 g of iodine in 50 mL of dry THF was added immediately. Reaction mixture was warmed up to room temperature, treated with aqueous solution of $NaHSO_3$ and extracted with ethyl acetate (4×40 mL). Organic fractions were combined, dried over sodium sulfate, filtered and evaporated. The residue was subjected to column chromatography on silica gel (hexane/ethyl acetate 9/1 mixture as eluent). The purified material was then crystallized from same solvents, providing 1.55 g of the target iodo-derivative, structure was confirmed by NMR and GC/MS data.

Step 4. The 100 mL round bottom flask, equipped with magnetic stirrer and refluxed condenser, was charged with iodo-derivative (1.55 g, 5 mmol), 3-(9-carbazolyl)carbazole (1.66 g, 5 mmol), $Pd(OAc)_2$ (225 mg, 20 mol %), $P(t-Bu)_3$ (5 mL of 1M solution in toluene, 5 mmol), potassium tert-buthoxide (0.96 g, 1.5 eq) and 75 mL of xylene. The flask was filled with nitrogen, and the reaction mixture was heated to reflux and stirred under nitrogen atmosphere for 24 hours. Then reaction was cooled down to room temperature, filtered through silica plug and evaporated. The residue was subjected to column chromatography on silica gel, eluent hexane/ethyl acetate mixture 9:1, providing 2.0 g of coupling product as white solid. The structure was confirmed by NMR and MS spectroscopy.

Step 5. The white product was dissolved in 100 mL of THF, cooled in the dry ice/acetone bath and n-BuLi solution in hexane (1 equivalent) was added as one portion. After 1 hour, 5 mL of water were added as one portion and the reaction mixture was warmed up to room temperature, diluted with water and extracted with ethyl acetate. Evaporation followed by column chromatography on silica gel (hexane/ethyl acetate 9/1 mixture as eluent) provided 1.5 g of target compound as white solid. Structure was confirmed by NMR and MS data.

Device Examples

All example devices were fabricated by high vacuum ($<10^{-7}$ Torr) thermal evaporation. The anode electrode is 800 Å of indium tin oxide (ITO). The cathode consisted of 10 Å of LiF followed by 1000 Å of Al. All devices are encapsulated with a glass lid sealed with an epoxy resin in a nitrogen glove box (<1 ppm of $H_2O$ and $O_2$) immediately after fabrication, and a moisture getter was incorporated inside the package.

Particular devices are provided wherein P1 is the emissive dopant and invention compound, Compound 8, Compound 15, Compound 17 or Compound 17', is the host. The organic stack of Device Examples 1-4 consisted of, sequentially from the ITO surface, 100 Å of P2 as the hole injecting layer (HIL), 300 Å of 4,4'-bis[N-(1-naphthyl)-N-phenylamino]biphenyl (α-NPD) as the hole transport layer (HTL), 300 Å of the invention compound doped with 9% of P1, an Ir phosphorescent compound, as the emissive layer (EML), 50 Å of the invention compound as ETL2 and 400 Å of $Alq_3$ (tris-8-hydroxyquinoline aluminum) as the ETL1.

Comparative Example 1 was fabricated similarly to the Device Examples, except that mCBP was used as the host.

As used herein, the following compounds have the following structures:

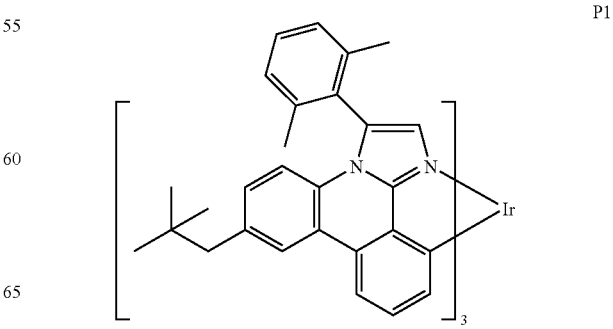

P1

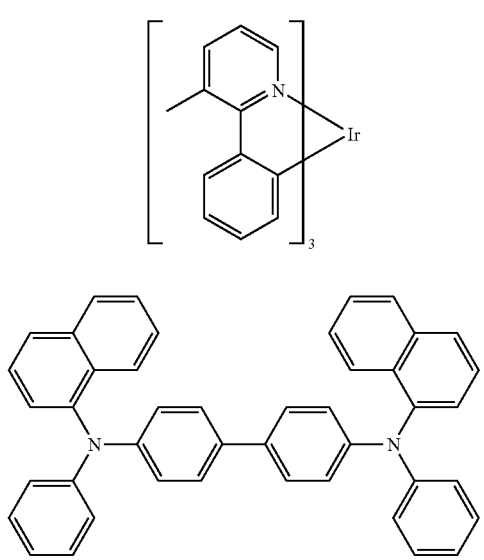

P2

NPD

The device structures and data are summarized in Tables 2 and 3. Table 2 shows device structure, in particular the host materials for the emissive layer and the material for the ETL2. Table 3 shows the corresponding measured results for those devices. Cmpd is an abbreviation of Compound. The oxidation potentials ($E_{ox}$) are designated as irreversible (i) or quasi-irreversible (q).

TABLE 2

| Device Example | Host | Dopant (9 wt %) | ETL2 (50 Å) | ETL1 (400 Å) | ITO thickness (Å) |
|---|---|---|---|---|---|
| Comparative Example 1 | mCBP | P1 | mCBP | Alq$_3$ | 800 |
| 1 | 8 | P1 | 8 | Alq$_3$ | 800 |
| 2 | 15 | P1 | 15 | Alq$_3$ | 800 |
| 3 | 17 | P1 | 17 | Alq$_3$ | 800 |
| 4 | 17' | P1 | 17' | Alq$_3$ | 800 |

TABLE 3

| Device Example | CIE X | CIE Y | Em$_{max}$ (nm) | At L = 1000 cd/m$^2$ V (V) | LE (cd/A) | EQE (%) | PE (lm/W) | LT$_{80\%}$ (hr) | E$_{ox}$ (V vs Fc$^+$/Fc) |
|---|---|---|---|---|---|---|---|---|---|
| Comparative Example 1 | 0.15 | 0.24 | 462 | 9.4 | 15.6 | 9.2 | 5.2 | 120 | 0.9 (i) |
| 1 | 0.17 | 0.31 | 466 | 10.8 | 9.0 | 4.4 | 2.6 | 40 | 0.86 (q) |
| 2 | 0.16 | 0.30 | 466 | 9.6 | 11.2 | 5.8 | 3.7 | 125 | 0.77 (q) |
| 3 | 0.16 | 0.29 | 464 | 8.3 | 13.6 | 7.2 | 5.2 | 160 | 0.74 (q) |
| 4 | 0.16 | 0.31 | 466 | 9.7 | 11.4 | 5.7 | 3.7 | 90 | 0.81 (q) |

From Device Examples 1-4, it can be seen that devices using the invention compounds as hosts give improved device stability while maintaining high triplet energy. In particular, Compounds 8, 15, 17 or 17' as hosts in blue or green OLEDs give devices with reduced oxidation potentials ($E_{ox}$ vs Fc$^+$/Fc) and improved electrochemical reversibility indicating that the carbazole containing compounds, in particular the unsymmetrical monodisperse linear 3,9-linked oligocarbazole compounds, may provide better charge balance and charge stability in the device.

The data suggest that carbazole containing compounds, particularly 3,9-linked oligocarbazoles, are excellent hosts and enhancement layer materials for phosphorescent OLEDs, providing improved charge balance and charge stability compared to the commonly used mCBP host. In addition, the oligocarbazole containing compounds may also provide better film formation during device production due to the unsymmetrical nature of the molecules.

It is understood that the various embodiments described herein are by way of example only, and are not intended to limit the scope of the invention. For example, many of the materials and structures described herein may be substituted with other materials and structures without deviating from the spirit of the invention. The present invention as claimed may therefore includes variations from the particular examples and preferred embodiments described herein, as will be apparent to one of skill in the art. It is understood that various theories as to why the invention works are not intended to be limiting.

The invention claimed is:

1. A carbazole-containing compound comprising:

FORMULA I

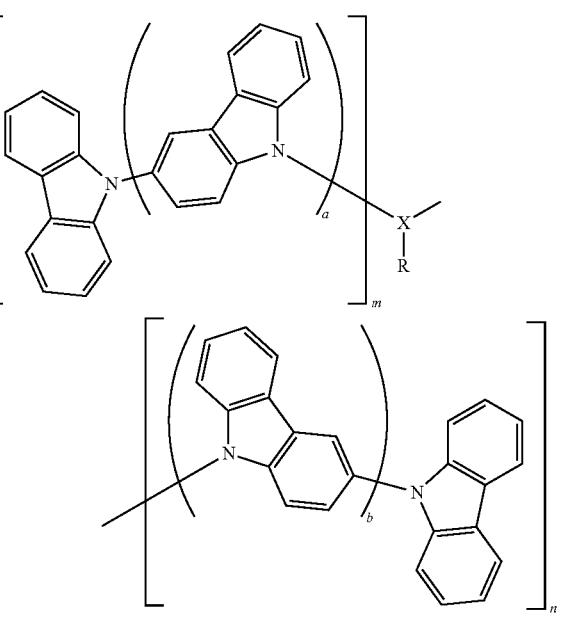

wherein a is 1 to 20;
wherein b is 0 to 20;
wherein m is 0 to 2;
wherein n is 0 to 2;
wherein m+n is at least 1;
wherein X is selected from the group consisting of biphenyl, terphenyl, naphthalene, triphenylene, phenanthrene, fluorene, chrysene, dibenzothiophene, dibenzofuran, benzofuran, benzothiophene, pyrazole, imidazole, triazole, oxazole, thiazole, oxadiazole, oxatriazole, dioxazole, thiadiazole, pyridine, pyridazine, pyrimidine, pyrazine, triazine, indole, benzimidazole, indazole, benzoxazole, benzisoxazole, benzothiazole, quinoline, isoquinoline, cinnoline, quinazoline, quinoxaline, naphthyridine, phthalazine, pteridine, xanthene, phenothiazine, phenoxazine, benzofuropyridine, furodipyridine, benzothienopyridine, and thienodipyridine; and
wherein X is substituted by R, where R is selected from the group consisting of hydrogen, alkyl, heteroalkyl, benzene, biphenyl, terphenyl, naphthalene, phenalene, phenanthrene, fluorene, chrysene, dibenzothiophene, dibenzofuran, benzofuran, benzothiophene, pyrazole, imidazole, triazole, oxazole, thiazole, oxadiazole, oxatriazole, dioxazole, thiadiazole, pyridine, pyridazine, pyrimidine, pyrazine, triazine, indole, benzimidazole, indazole, benzoxazole, benzisoxazole, benzothiazole, quinoline, isoquinoline, cinnoline, quinazoline, quinoxaline, naphthyridine, phthalazine, pteridine, xanthene, phenothiazine, phenoxazine, benzofuropyridine, furodipyridine, benzothienopyridine, and thienodipyridine.

2. The compound of claim 1, wherein a is 1 to 20 and n is 0.

3. The compound of claim 1, wherein a is 1 or 2 and n is 0.

4. The compound of claim 1, wherein a is 1, b is 1, and n is 1.

5. The compound of claim 1, wherein X is selected from biphenyl, terphenyl, triphenylene, phenanthrene, fluorene, dibenzothiophene, dibenzofuran, pyridine, pyridazine, pyrimidine, pyrazine, triazine, benzimidazole, benzothiazole, quinoline, isoquinoline, benzofuropyridine, furodipyridine, benzothienopyridine, and thienodipyridine.

6. The compound of claim 1, wherein X is selected from the group consisting of dibenzothiophene, dibenzofuran, benzofuropyridine, furodipyridine, benzothienopyridine, thienodipyridine, and triphenylene.

7. The compound of claim 1, wherein R is selected from the group consisting of hydrogen, alkyl, benzene, biphenyl, terphenyl, triphenylene, phenanthrene, fluorene, dibenzothiophene, dibenzofuran, pyridine, pyridazine, pyrimidine, pyrazine, triazine, benzimidazole, benzothiazole, quinoline, isoquinoline, benzofuropyridine, furodipyridine, benzothienopyridine, and thienodipyridine.

8. The compound of claim 1 wherein R is selected from the group consisting of hydrogen, alkyl, benzene, biphenyl, terphenyl, dibenzothiophene, dibenzofuran.

9. The compound of claim 5, wherein R is selected from the group consisting of hydrogen, alkyl, benzene, biphenyl, terphenyl, triphenylene, phenanthrene, fluorene, dibenzothiophene, dibenzofuran, pyridine, pyridazine, pyrimidine, pyrazine, triazine, benzimidazole, benzothiazole, quinoline, isoquinoline, benzofuropyridine, furodipyridine, benzothienopyridine, and thienodipyridine.

10. The compound of claim 6, wherein R is selected from the group consisting of hydrogen, alkyl, benzene, biphenyl, terphenyl, dibenzothiophene, dibenzofuran.

11. The compound of claim 1, wherein the compound is selected from the group consisting of:

Compound 1G

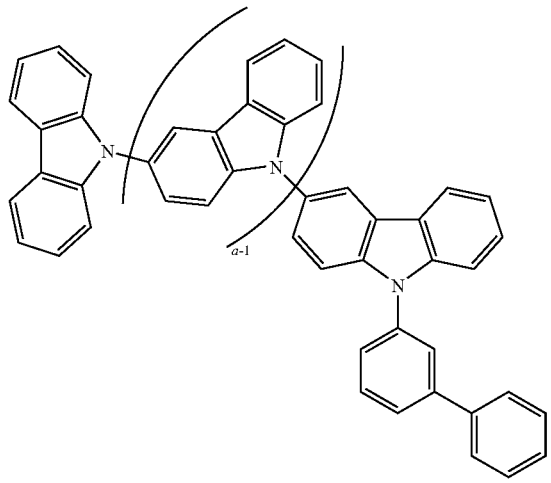

Compound 2G

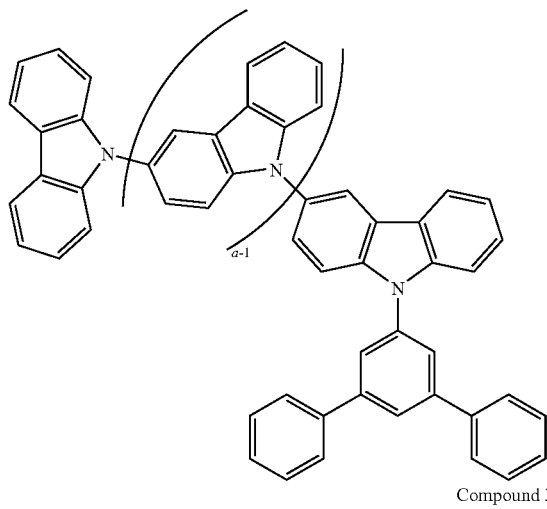

Compound 3G

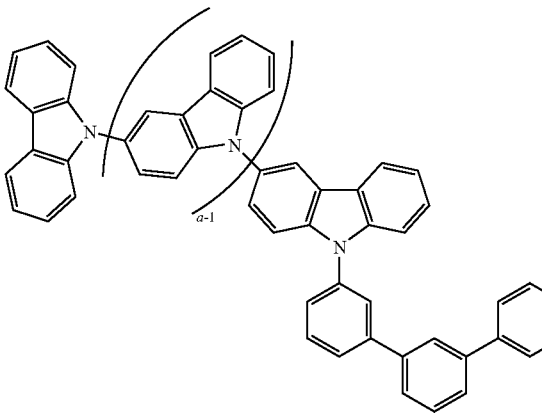

Compound 4G
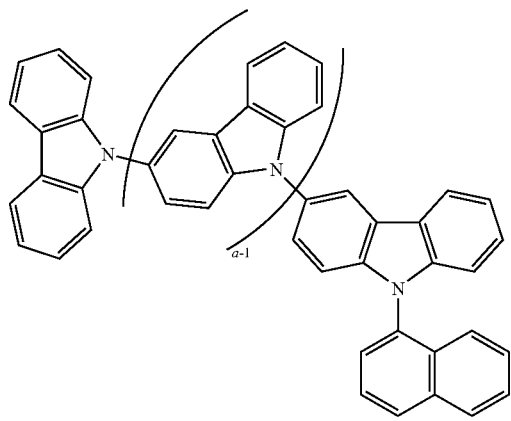
Compound 5G
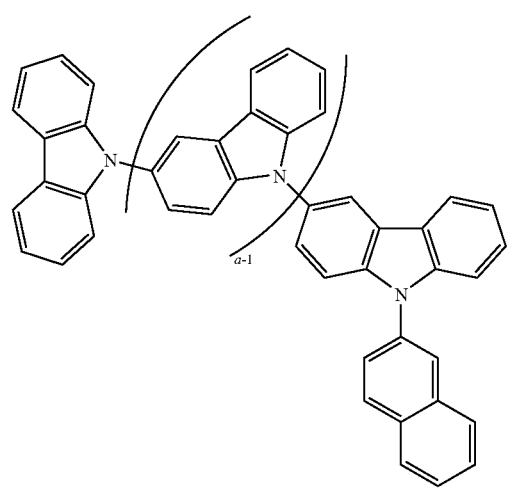
Compound 6G
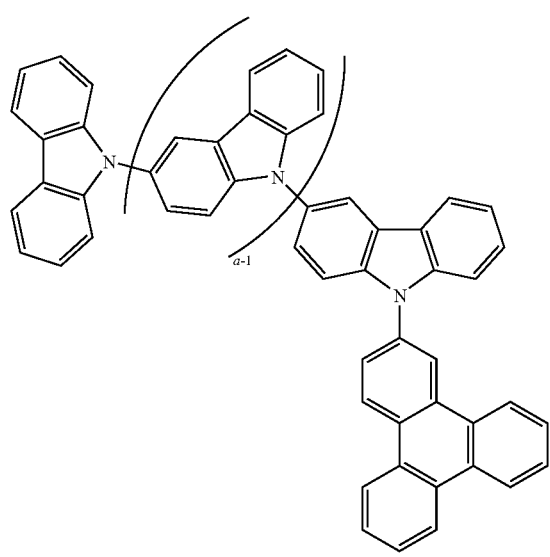
Compound 7G
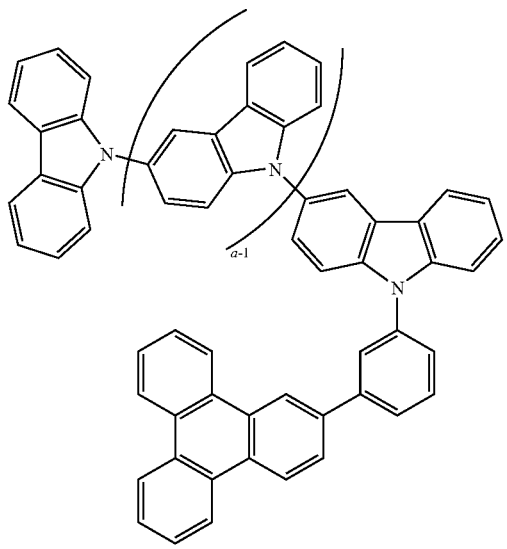
Compound 8G
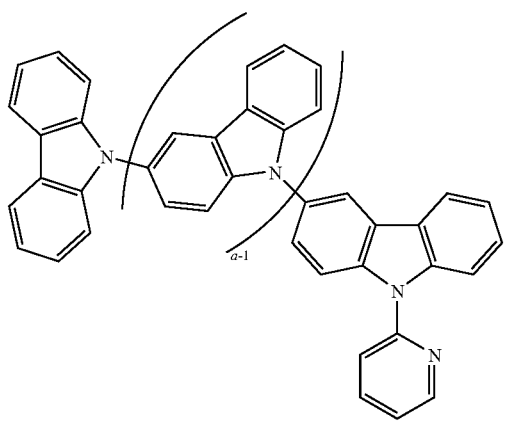
Compound 9G
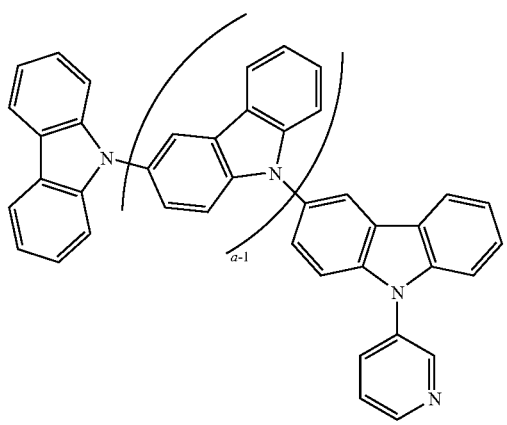

-continued
Compound 10G
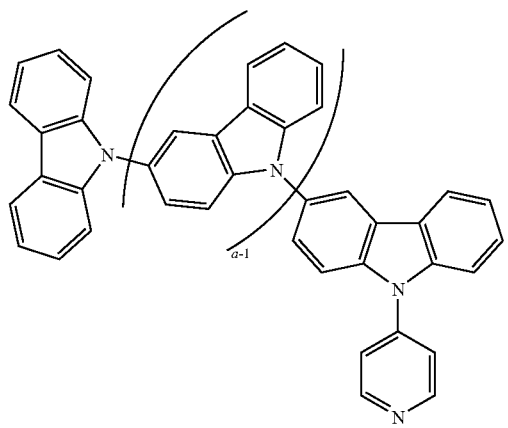
Compound 11G
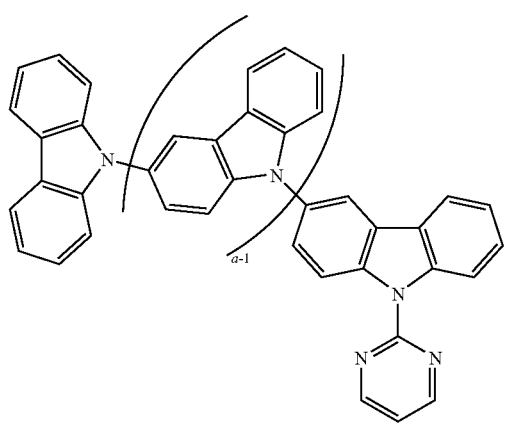
Compound 12G
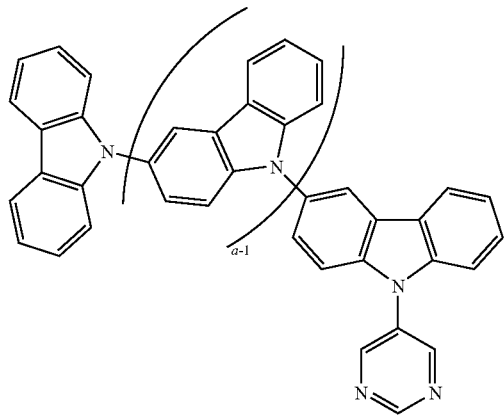
-continued
Compound 13G
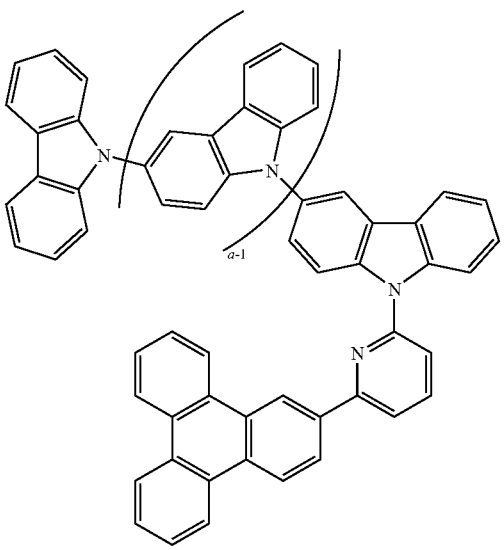
Compound 14G
Compound 15G
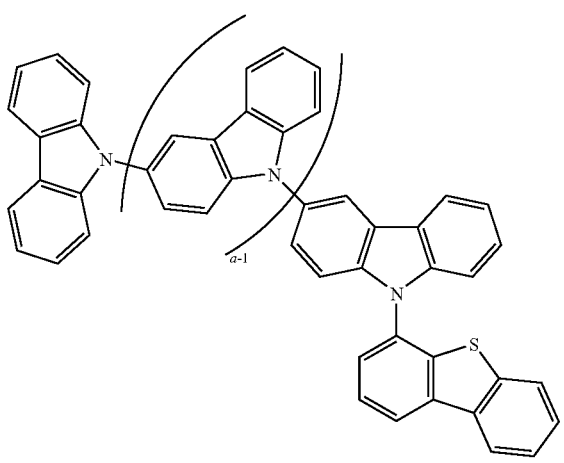

Compound 16G
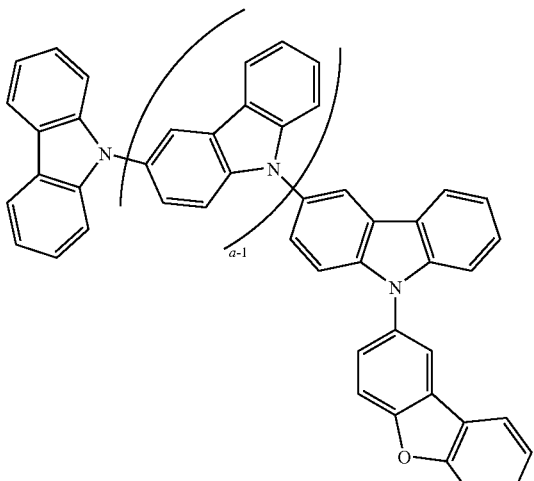
Compound 19G
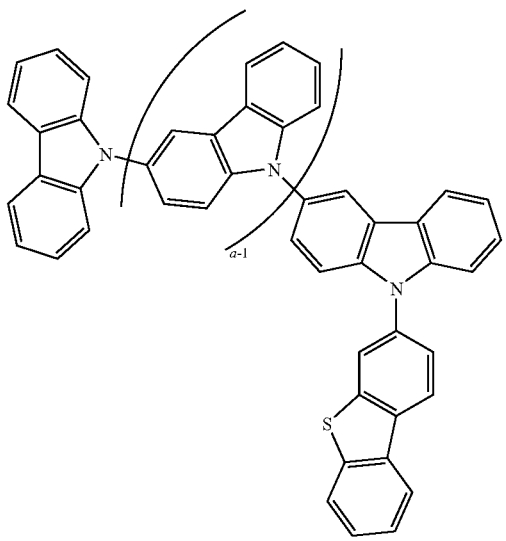
Compound 17G
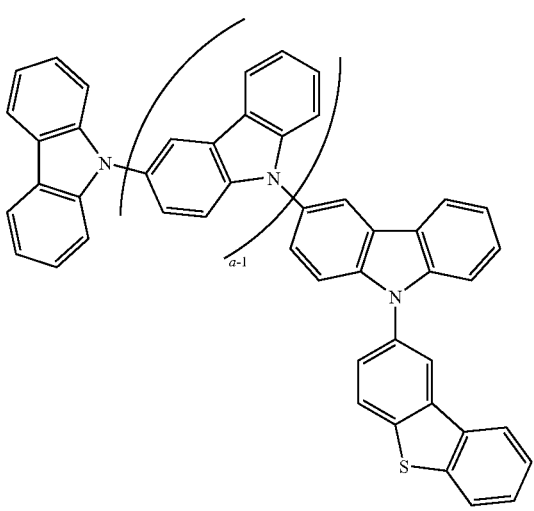
Compound 20G
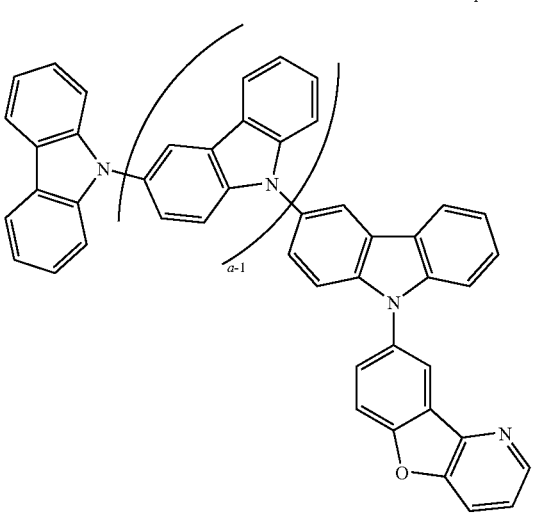
Compound 18G
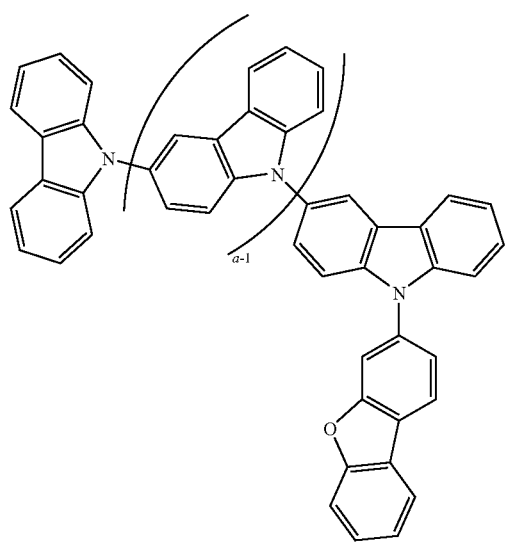
Compound 21G Compound 22G
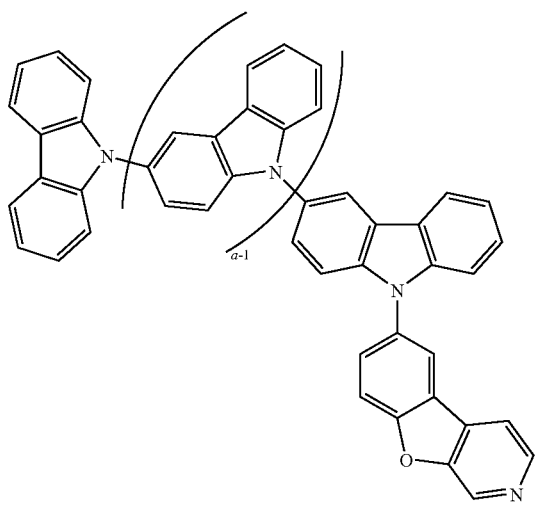
Compound 23G
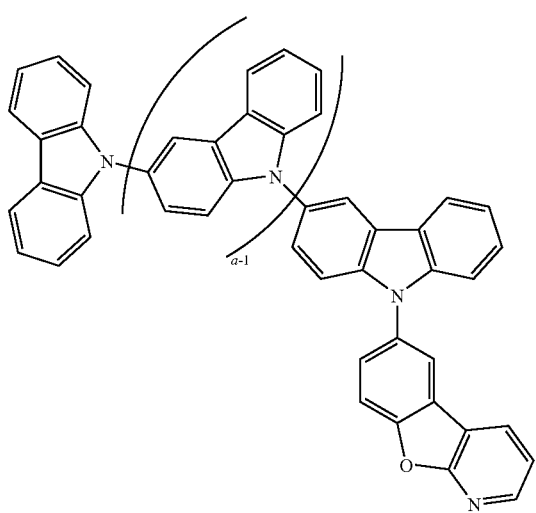
Compound 24G
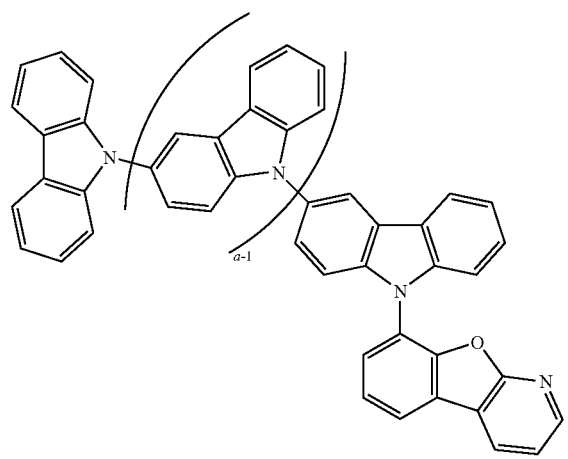
Compound 25G
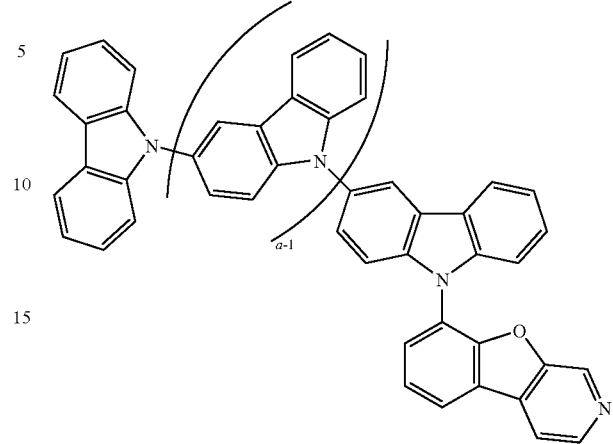
Compound 26G
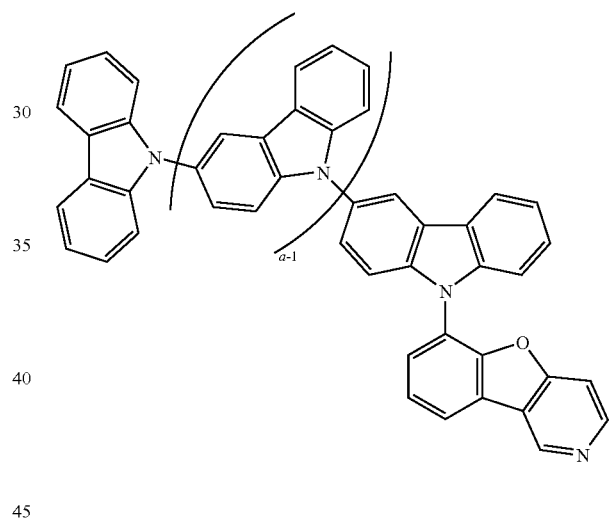
Compound 27G
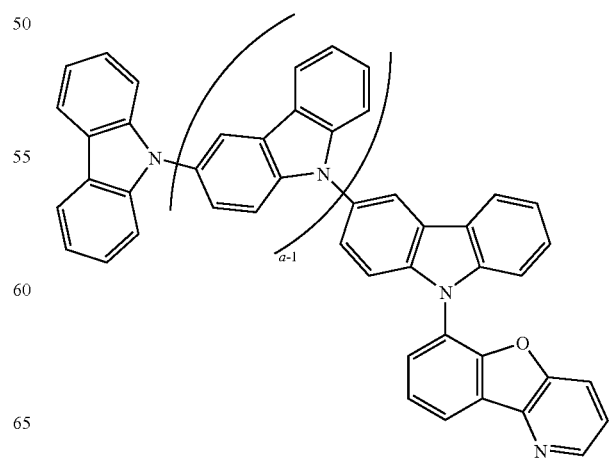

Compound 28G
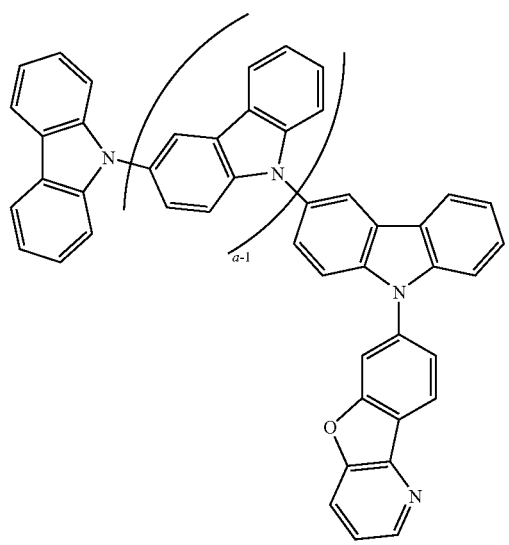
Compound 31G
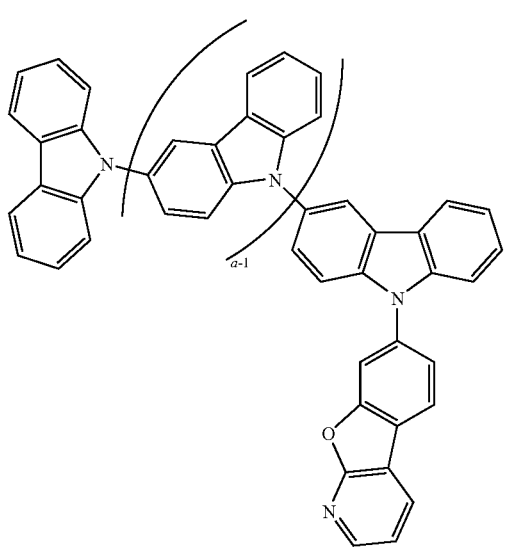
Compound 29G
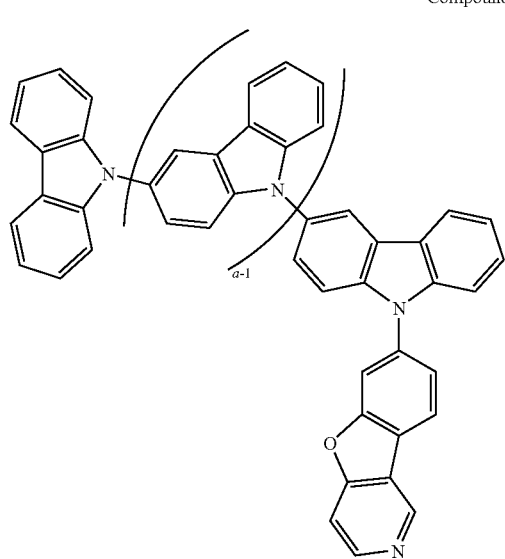
Compound 32G
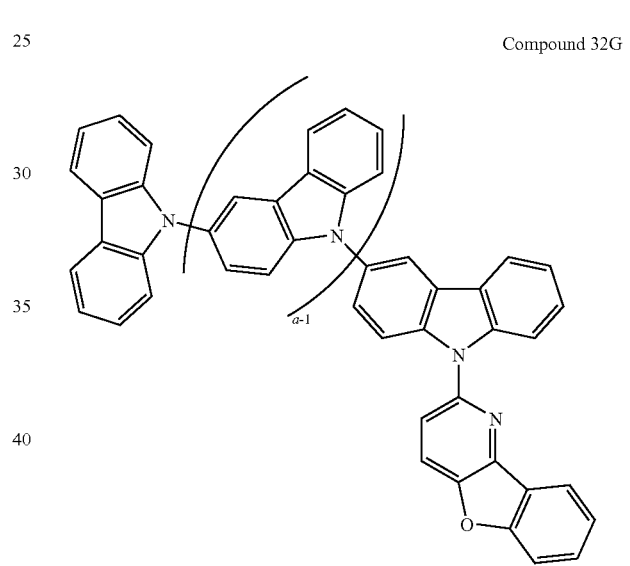
Compound 30G
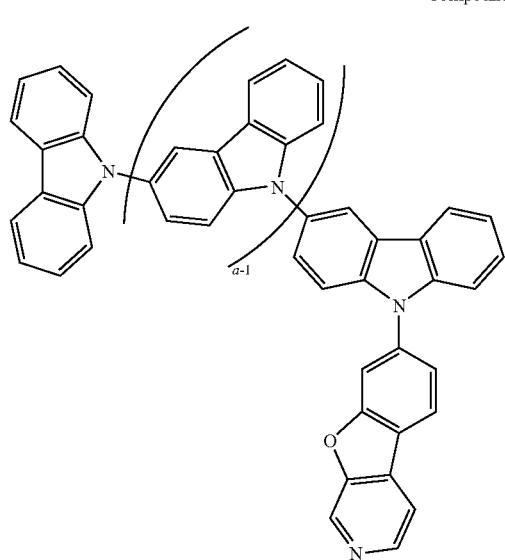
Compound 33G
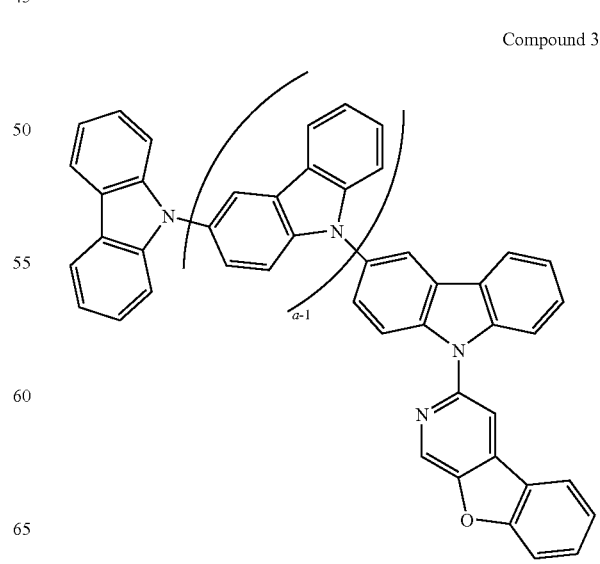

Compound 34G
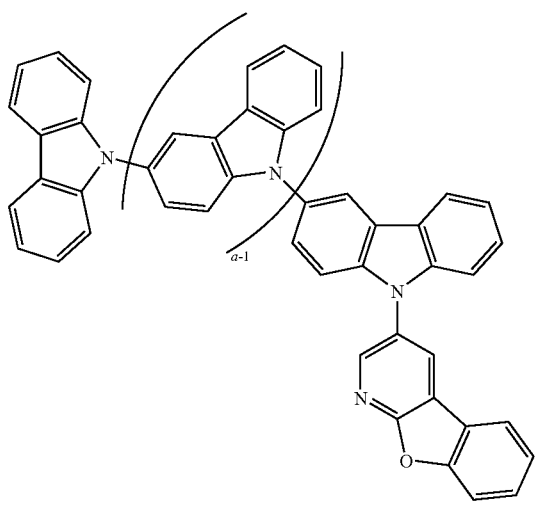
Compound 35G
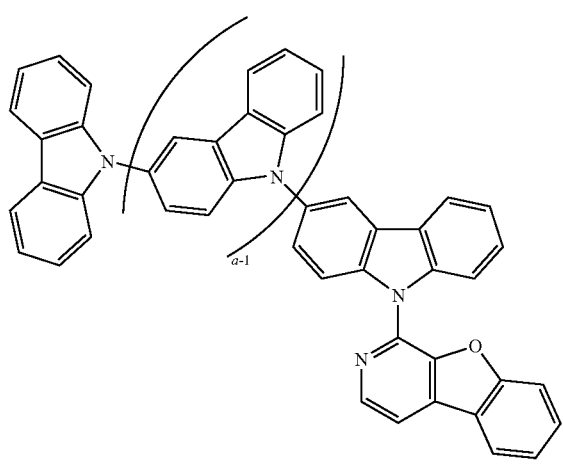
Compound 36G
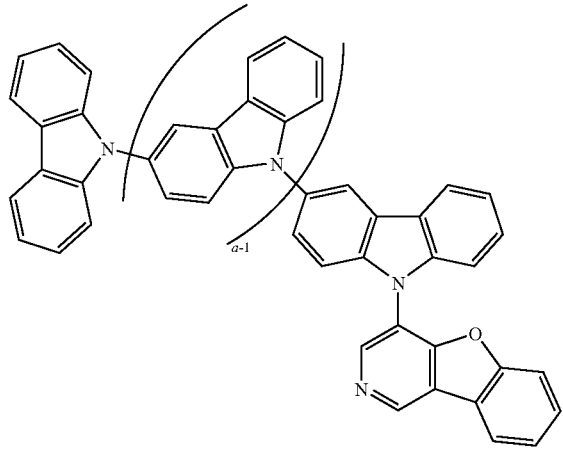
Compound 37G
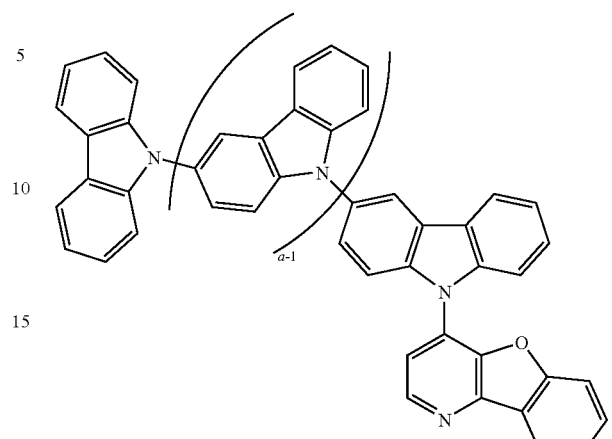
Compound 38G
Compound 39G Compound 40G
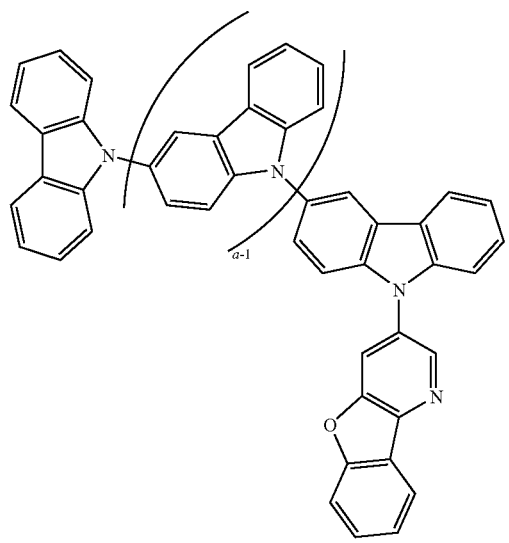
Compound 43G
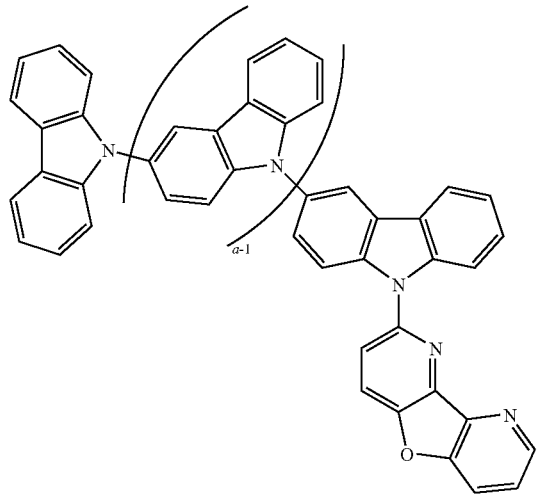
Compound 41G
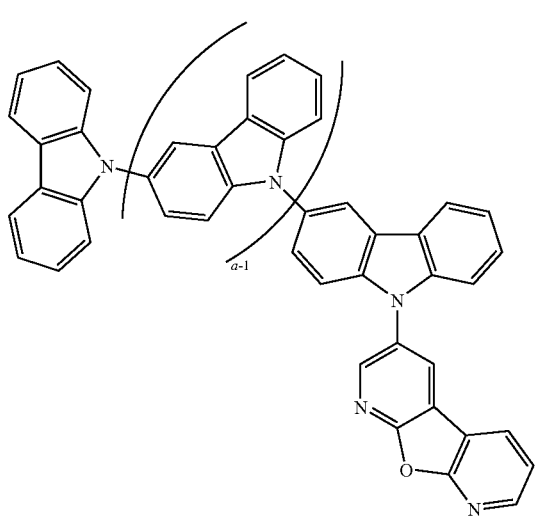
Compound 44G
Compound 42G
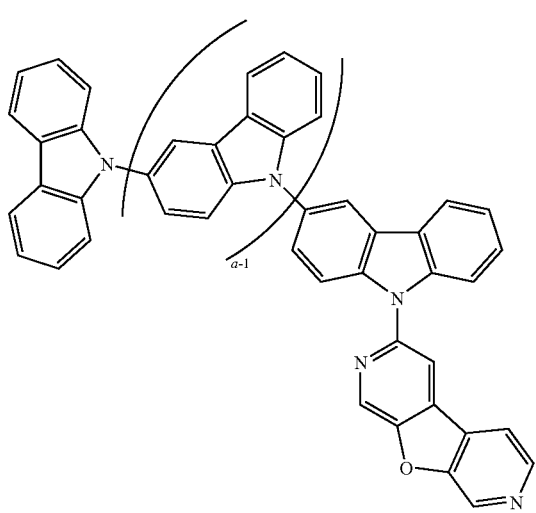
Compound 45G
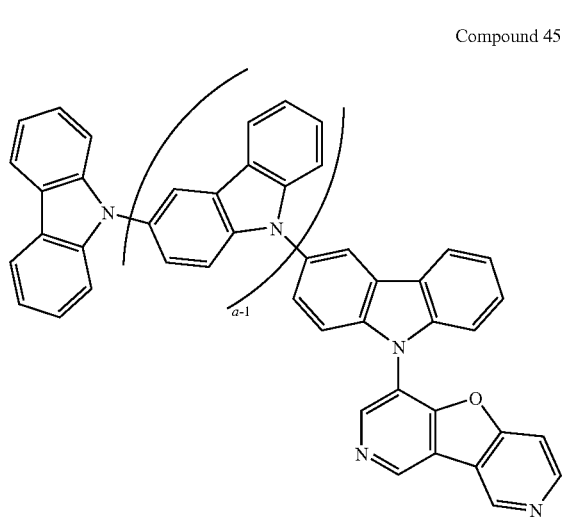

Compound 46G
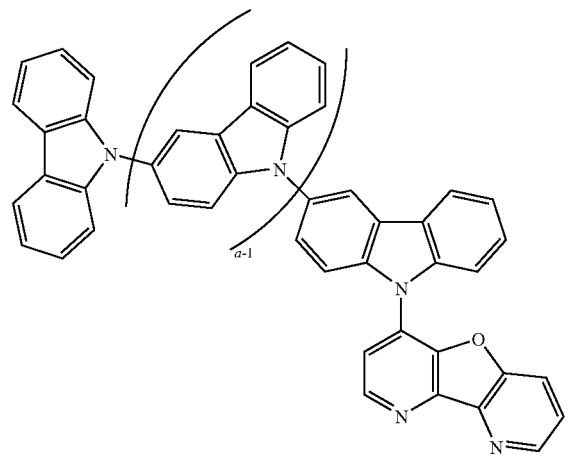
Compound 47G
Compound 48G
Compound 49G
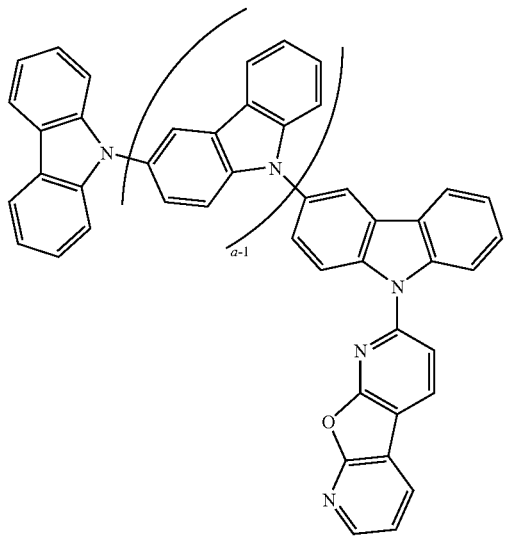
Compound 50G
Compound 51G
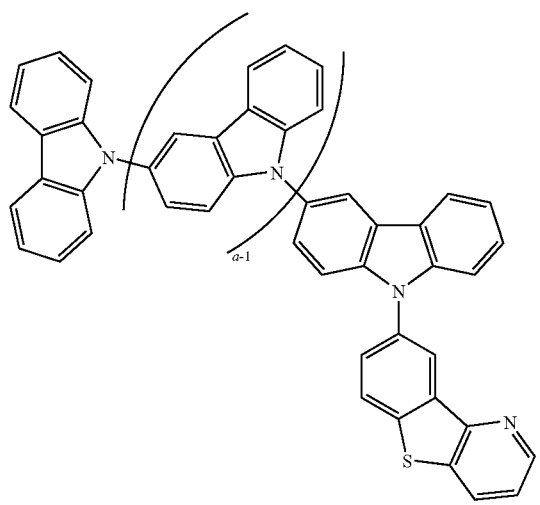

Compound 52G
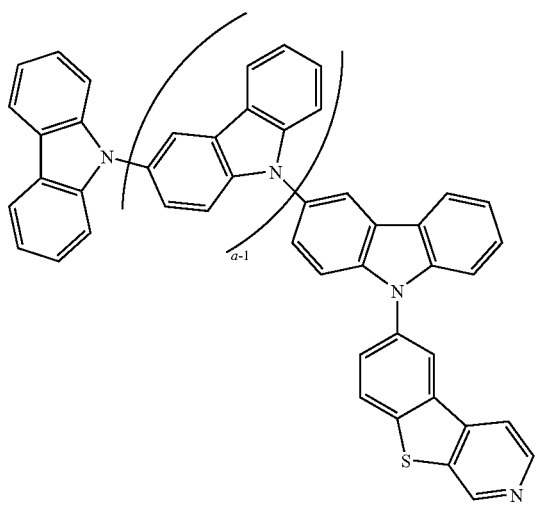
Compound 55G
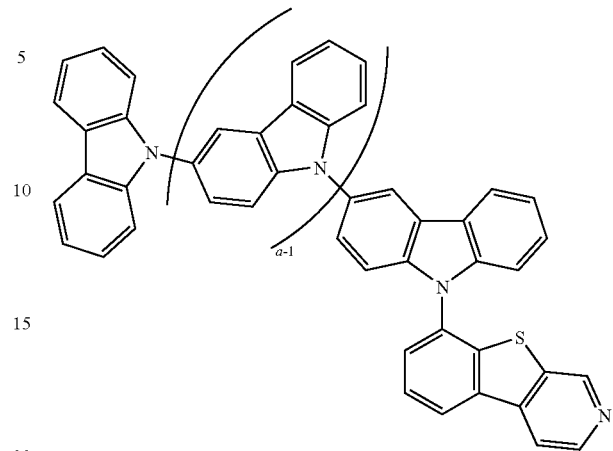
Compound 53G
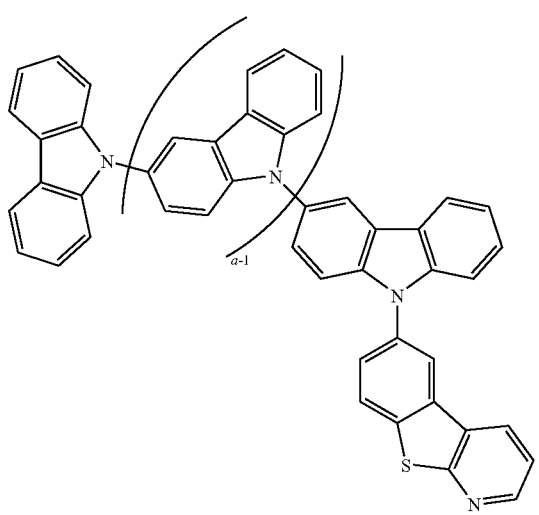
Compound 56G
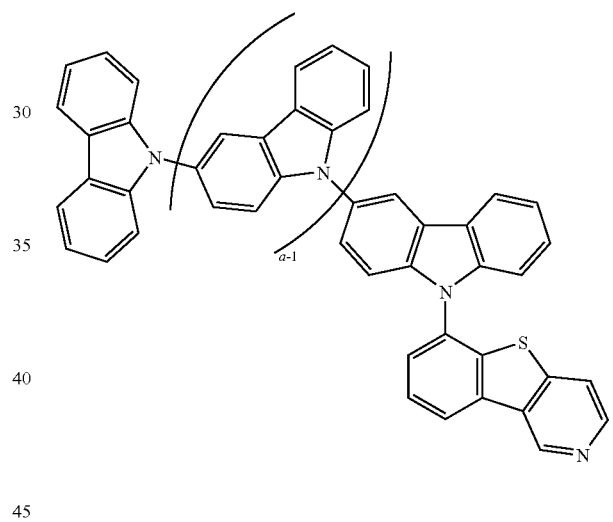
Compound 54G
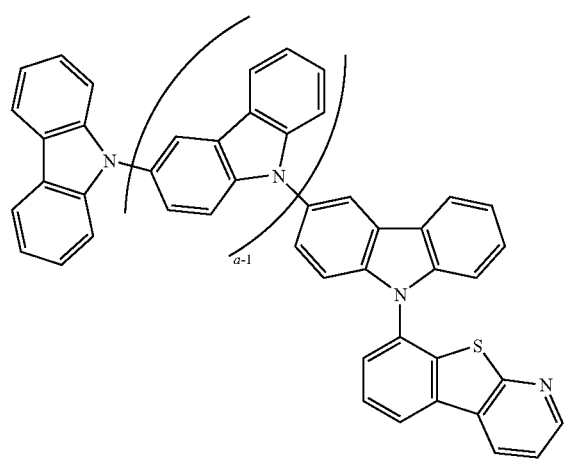
Compound 57G
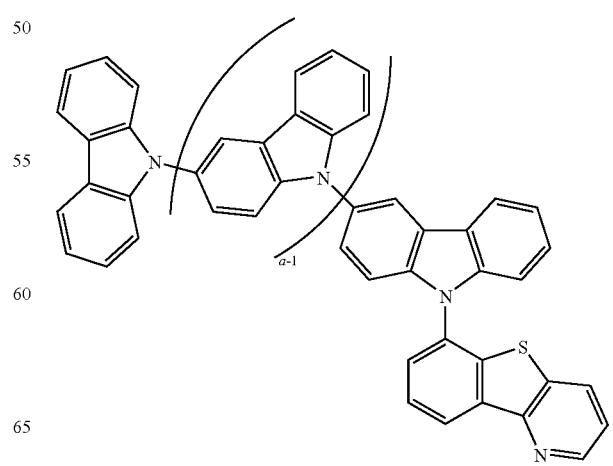

Compound 58G
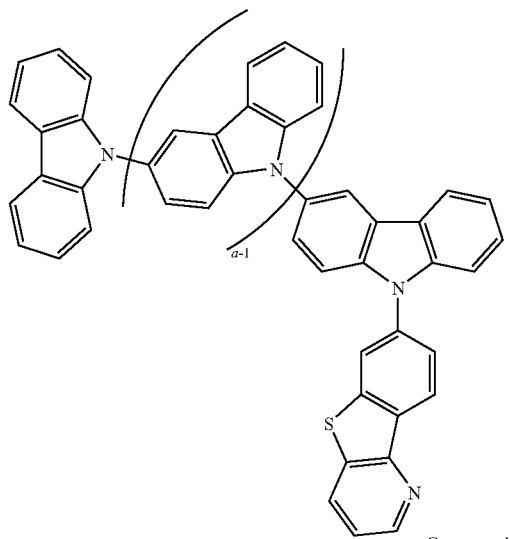
Compound 59G
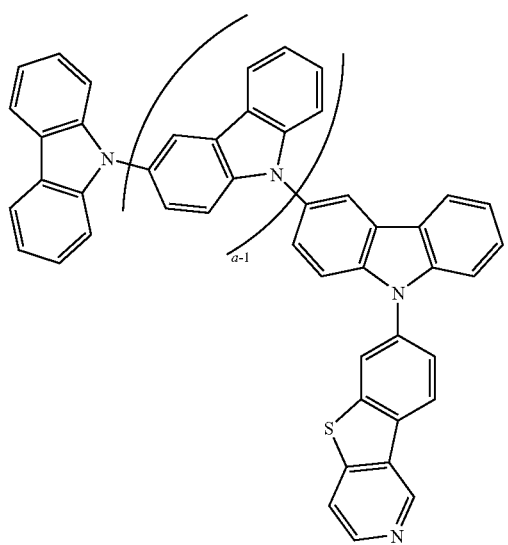
Compound 60G
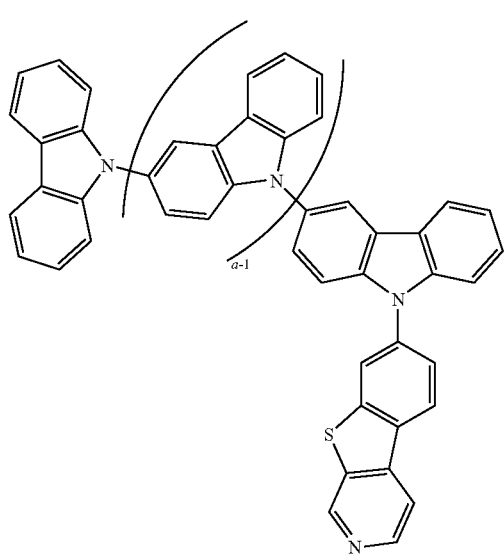
Compound 61G
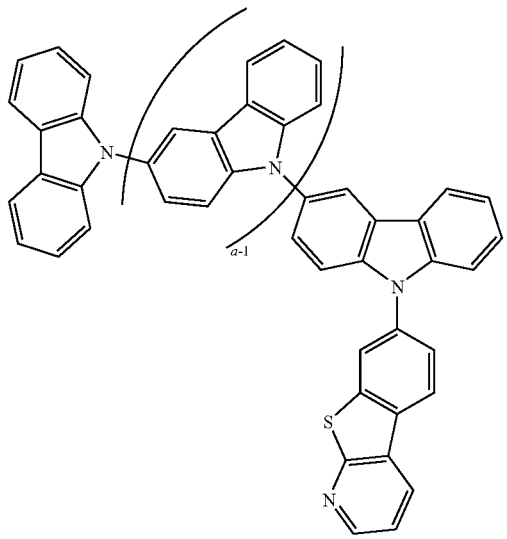
Compound 62G
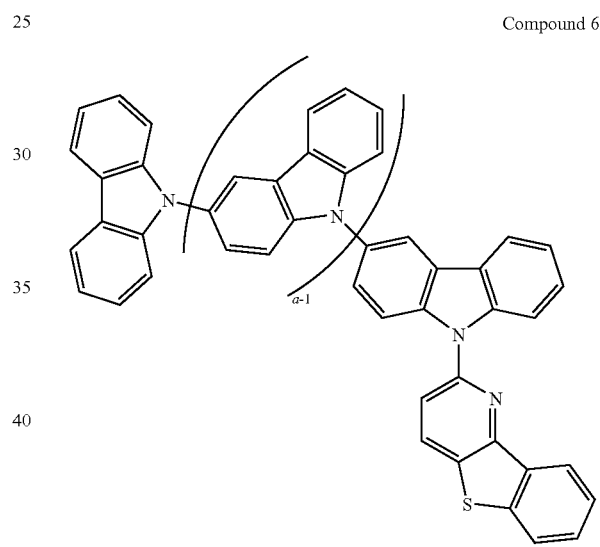
Compound 63G
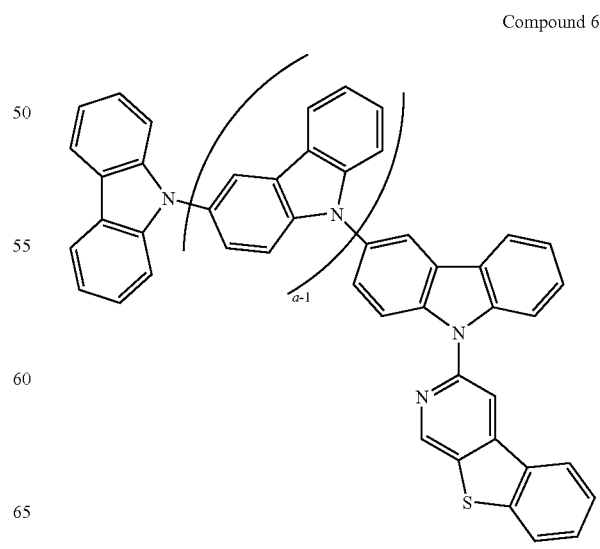

Compound 64G
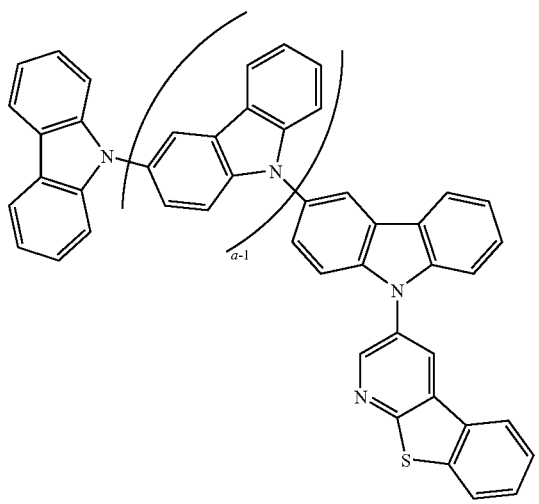
Compound 65G
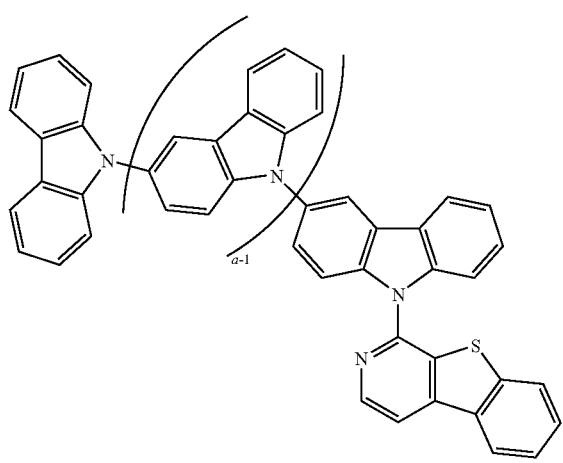
Compound 66G
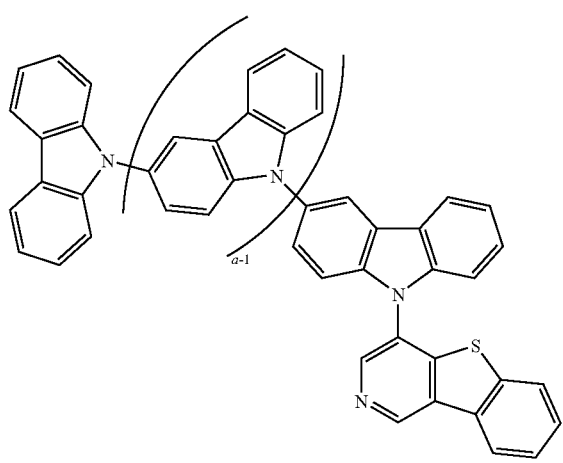
Compound 67G
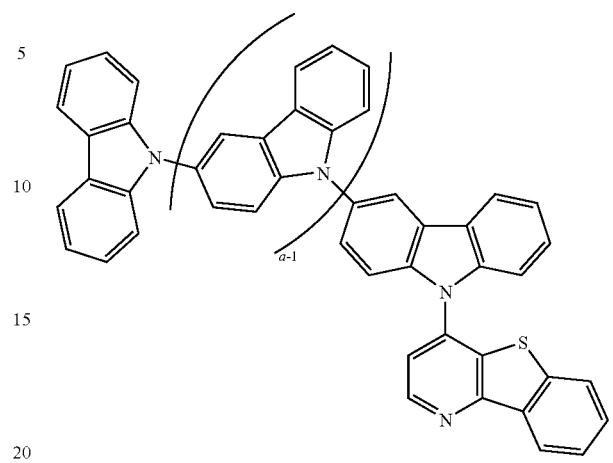
Compound 68G
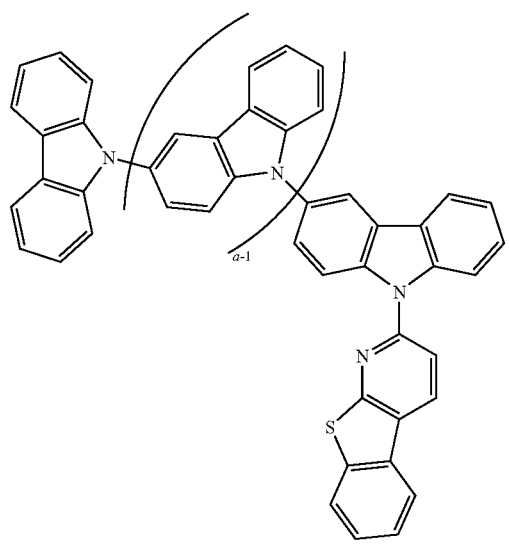
Compound 69G
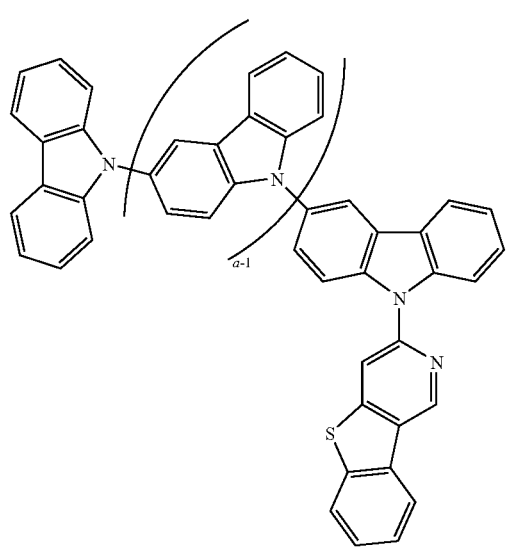

Compound 70G
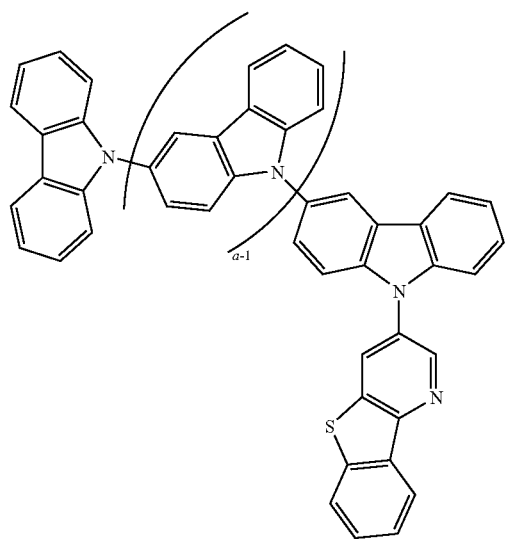
Compound 71G
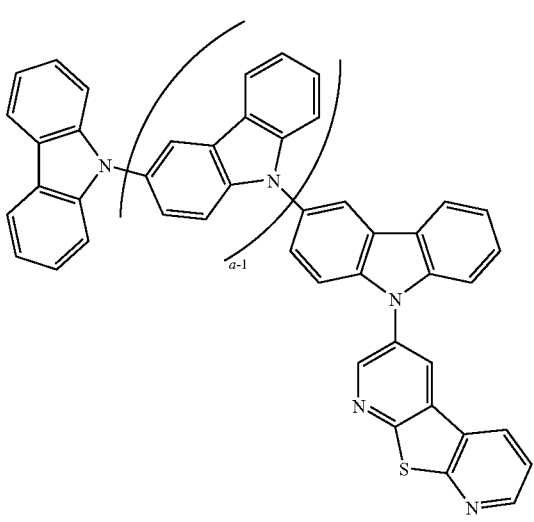
Compound 72G
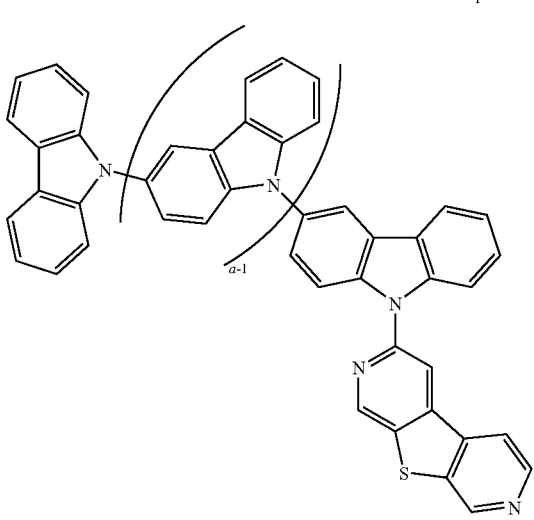
Compound 73G
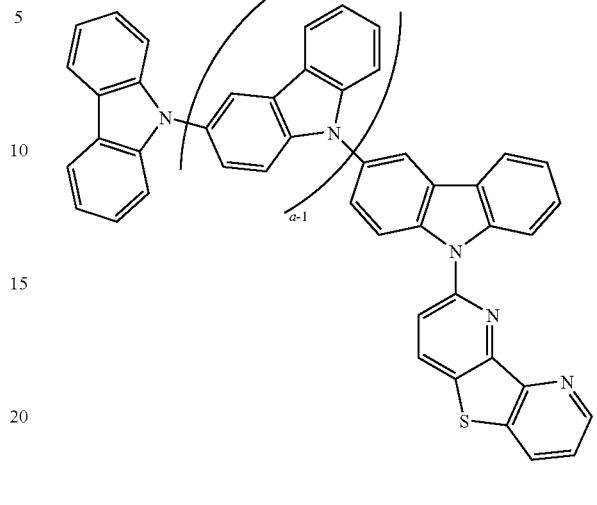
Compound 74G
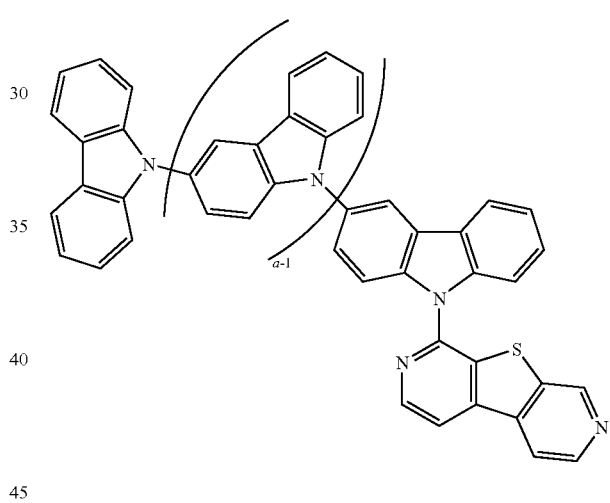
Compound 75G
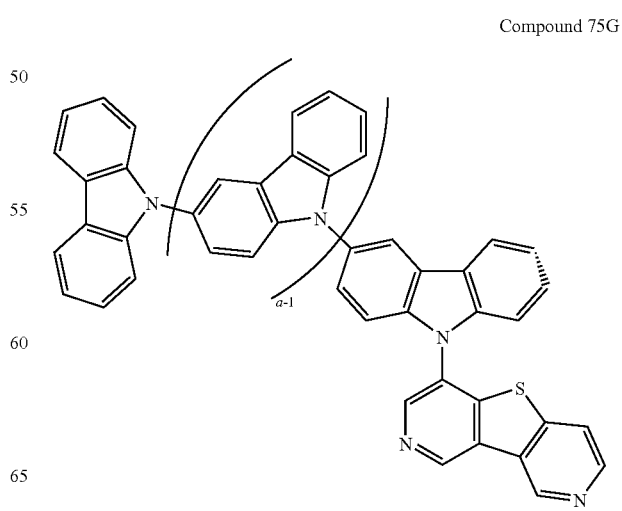

Compound 76G
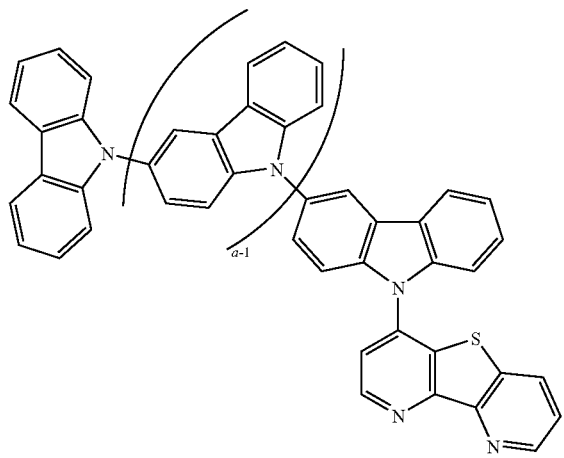
Compound 77G
Compound 79G
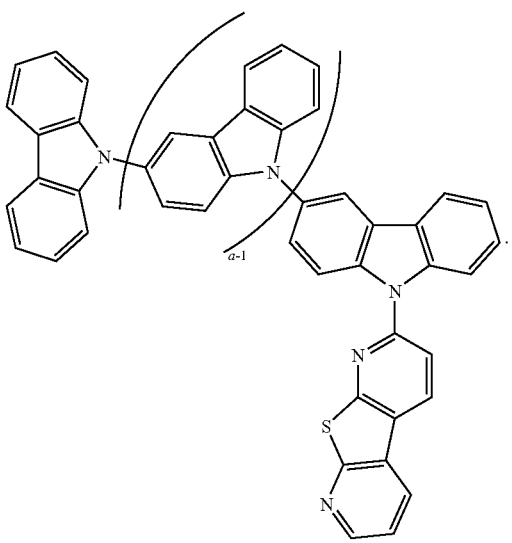
12. The compound of claim 11, wherein the compound is selected from the group consisting of:
Compound 15G
Compound 78G
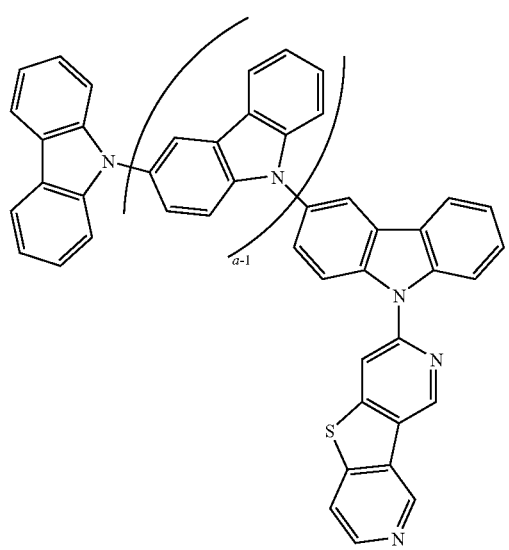
Compound 17G
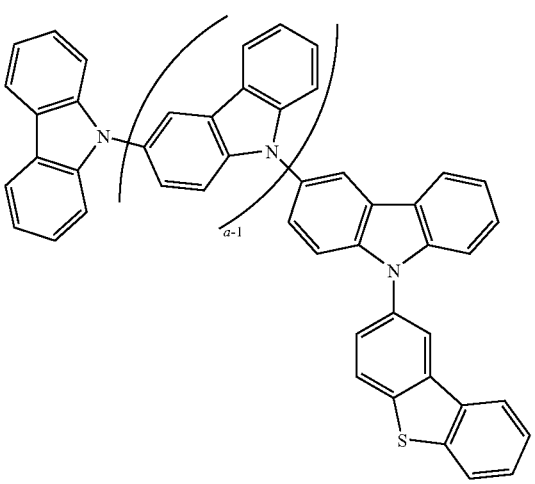

Compound 19G
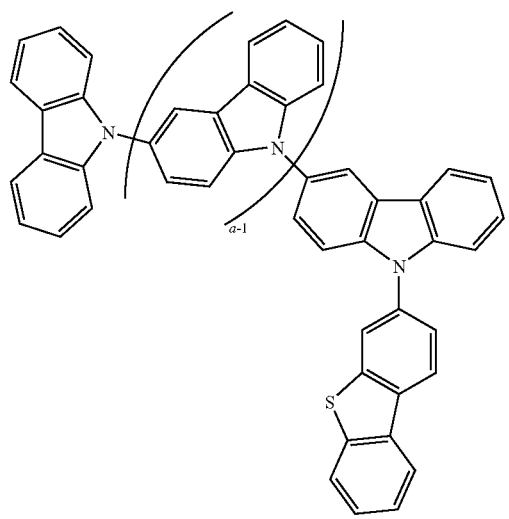
Compound 50G
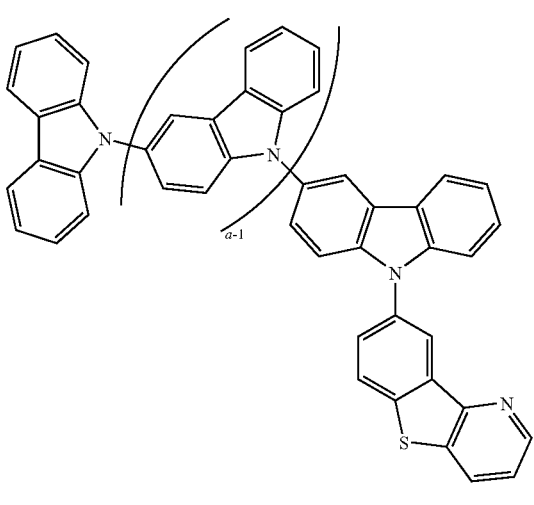
Compound 51G
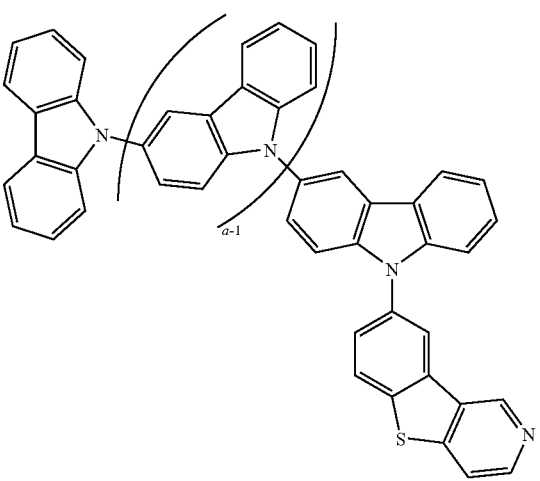
Compound 52G
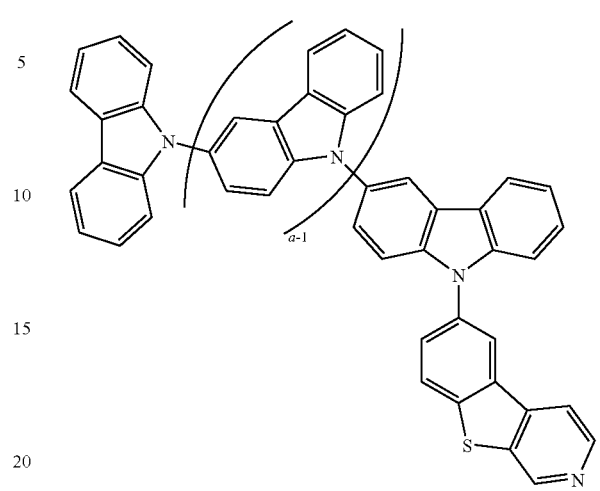
Compound 53G
Compound 54G
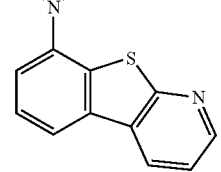

Compound 55G
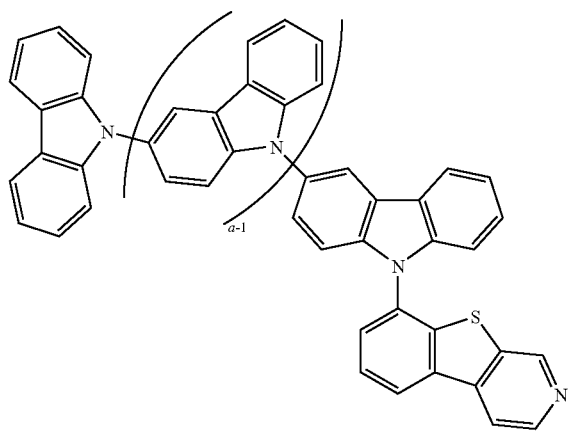
Compound 56G
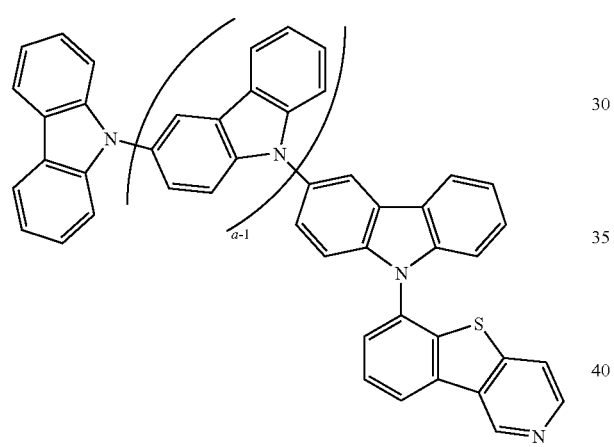
Compound 57G
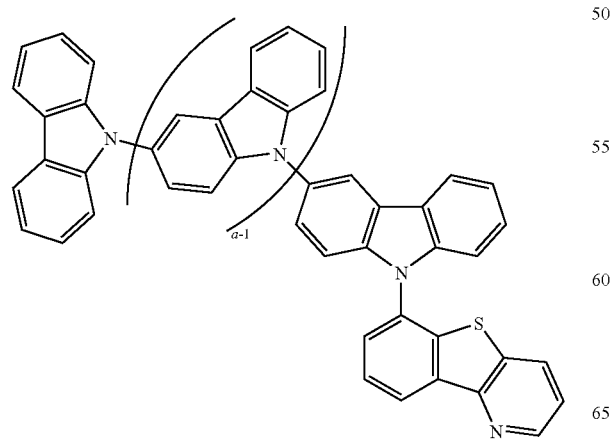
Compound 58G
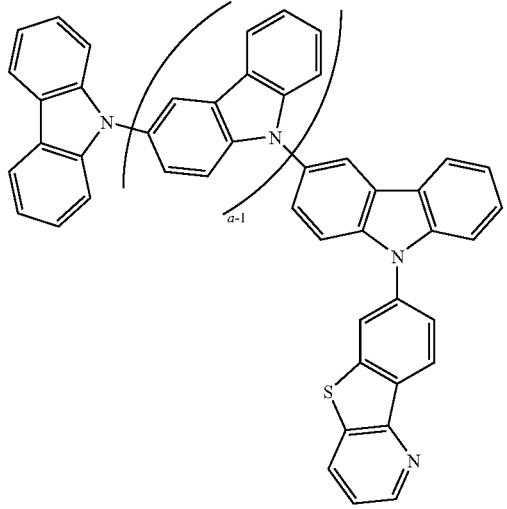
Compound 59G
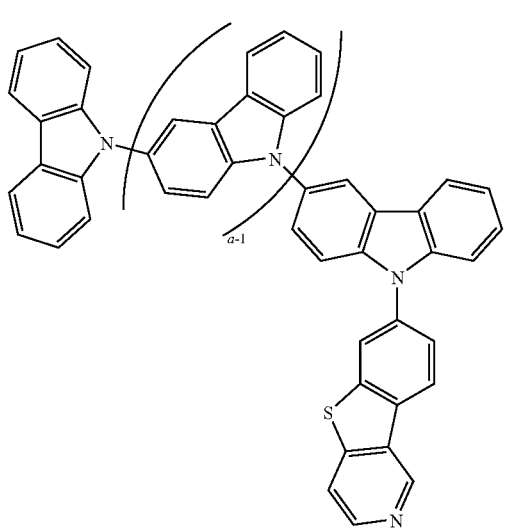
Compound 60G
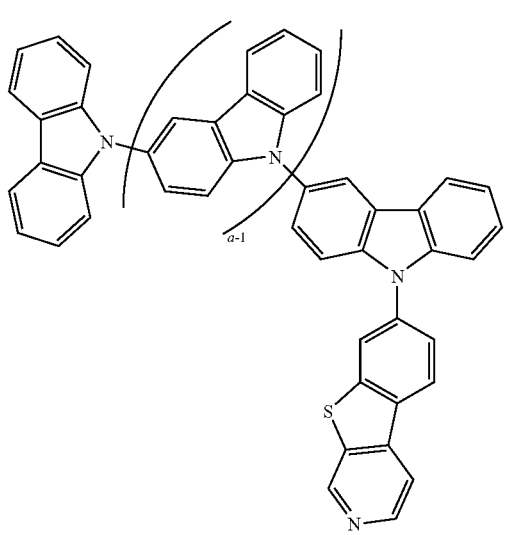

Compound 61G
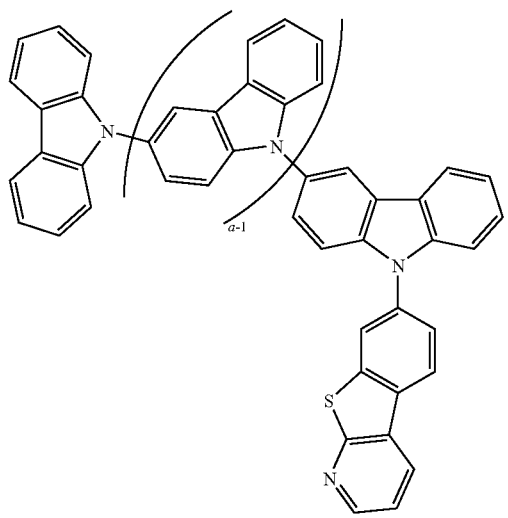
Compound 62G
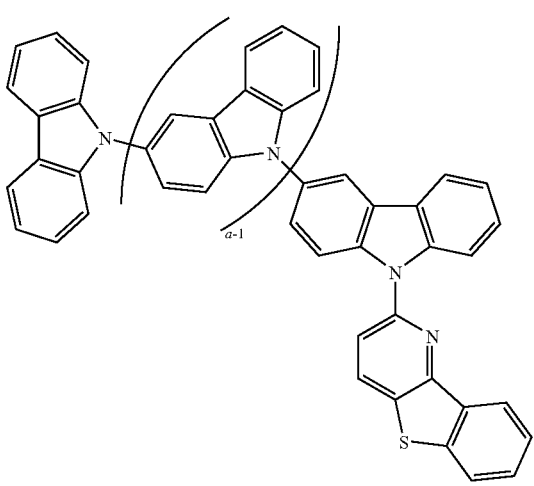
Compound 63G
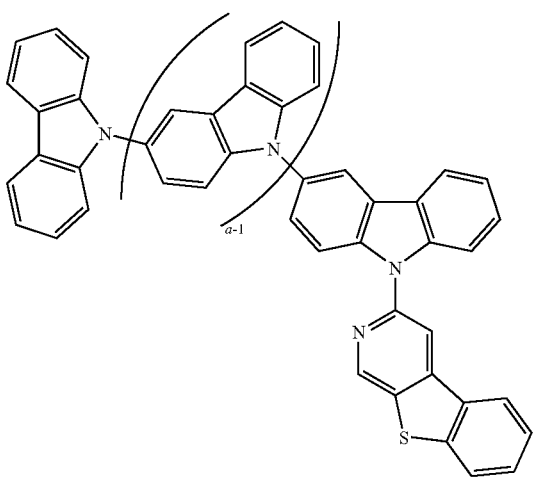
Compound 64G
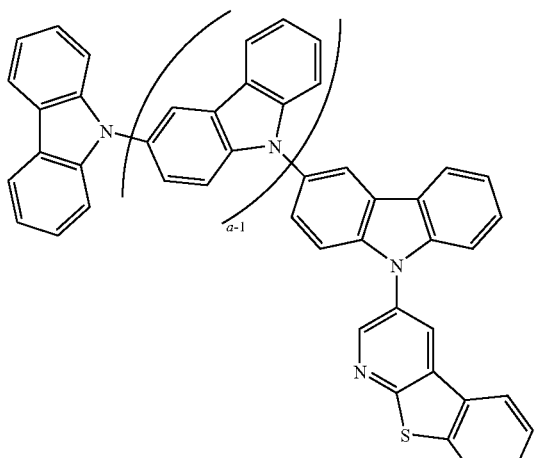
Compound 65G
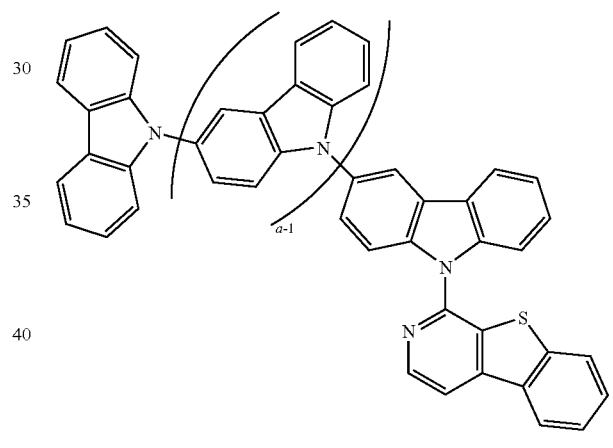
Compound 66G
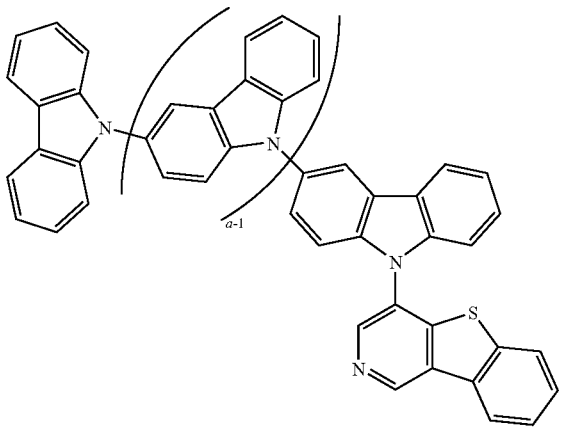

Compound 67G
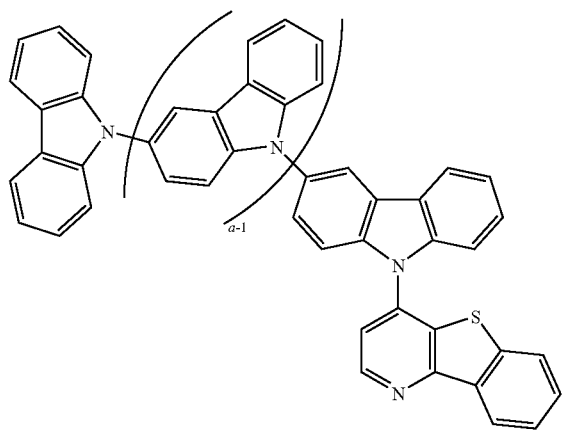
Compound 68G
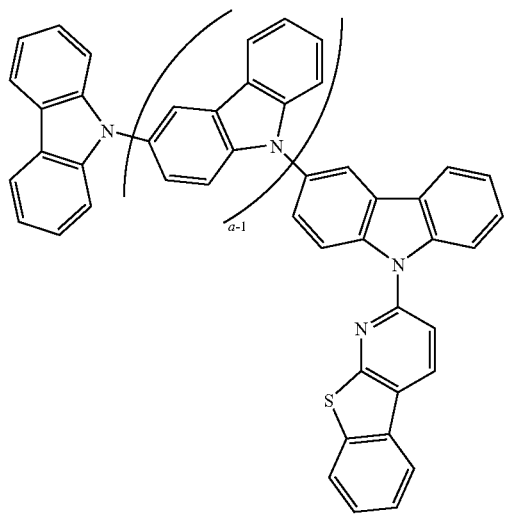
Compound 69G
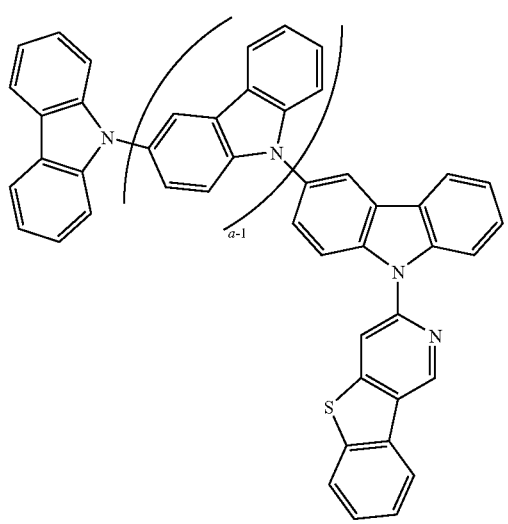
Compound 70G
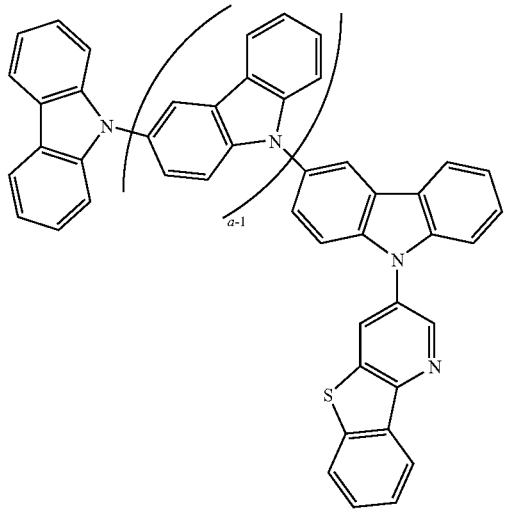
Compound 71G
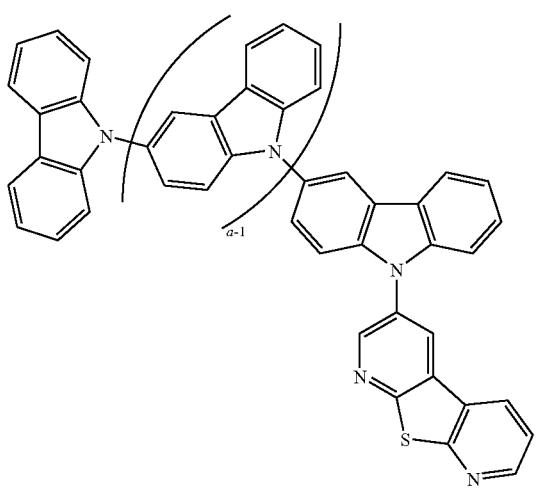
Compound 72G
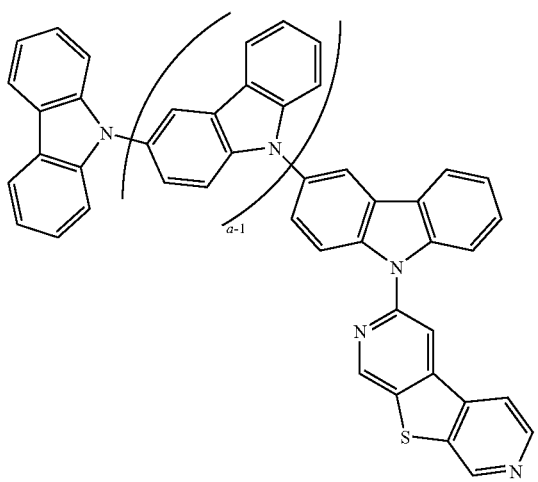

Compound 73G
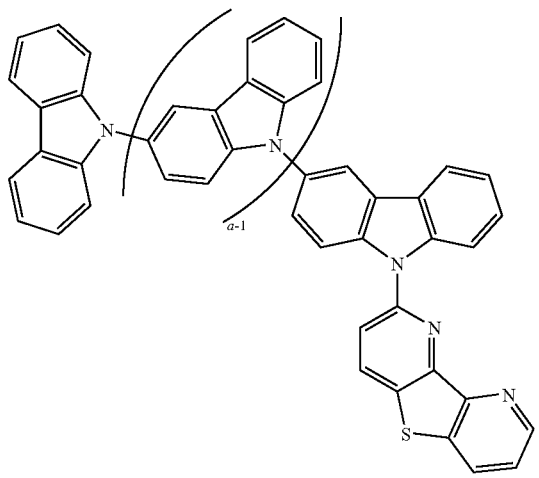
Compound 74G
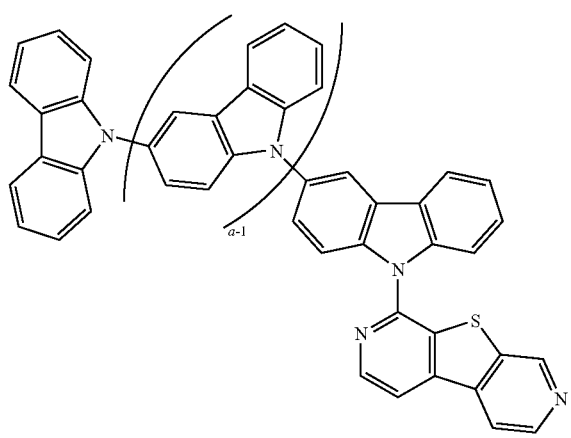
Compound 75G
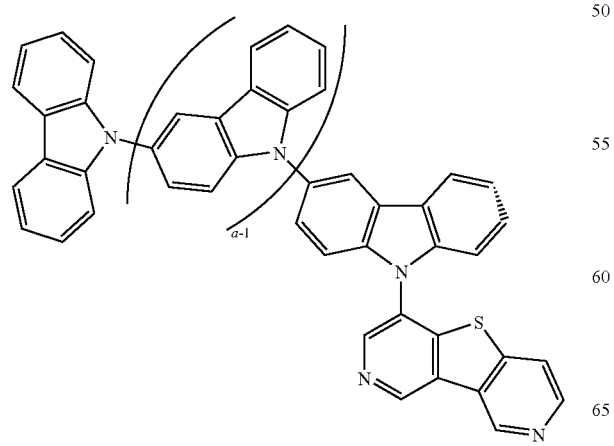
Compound 76G
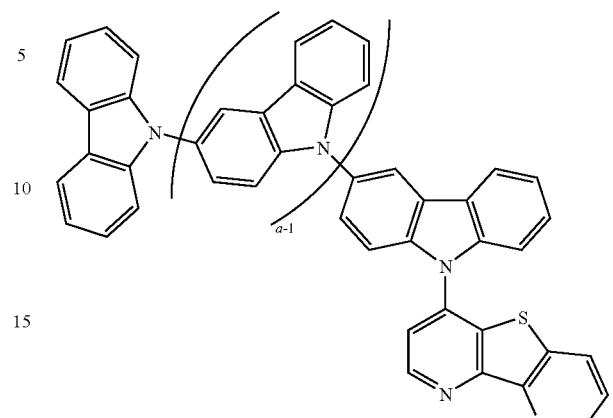
Compound 77G
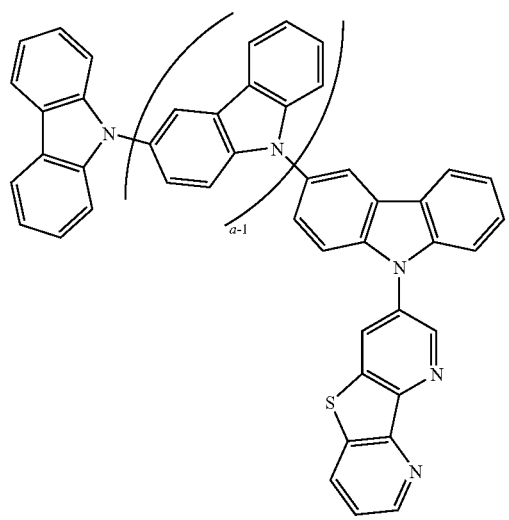
Compound 78G
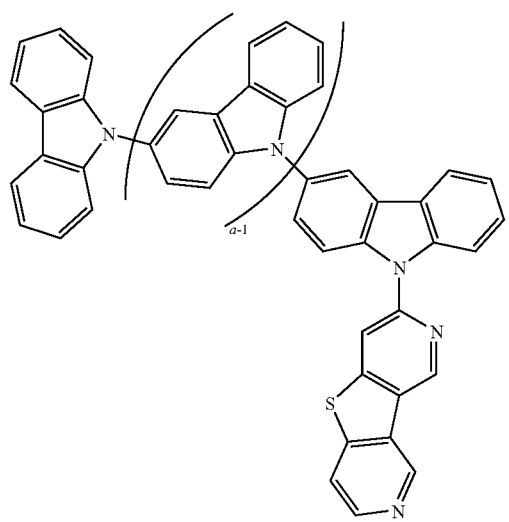

Compound 79G
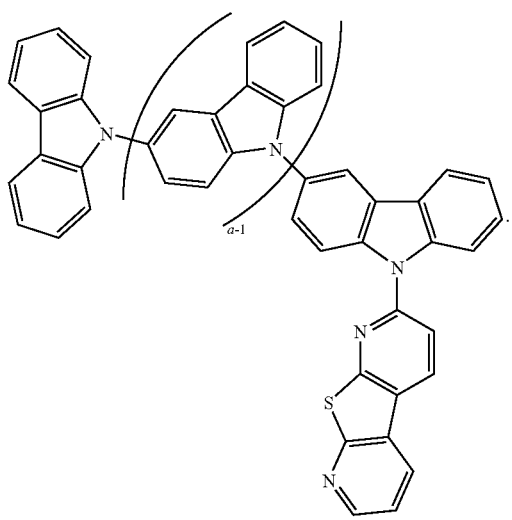
Compound 18G
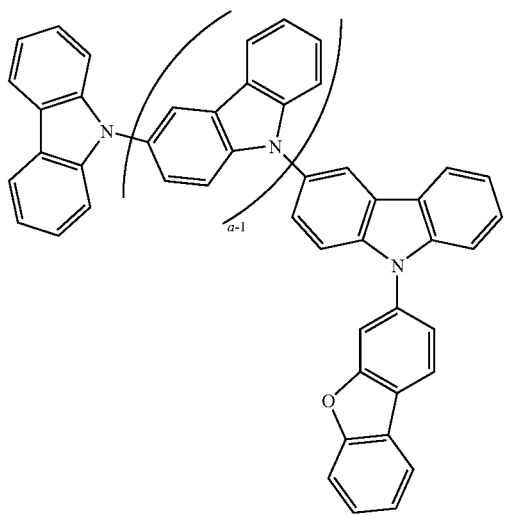
13. The compound of claim 11, wherein the compound is selected from the group consisting of:
Compound 14G
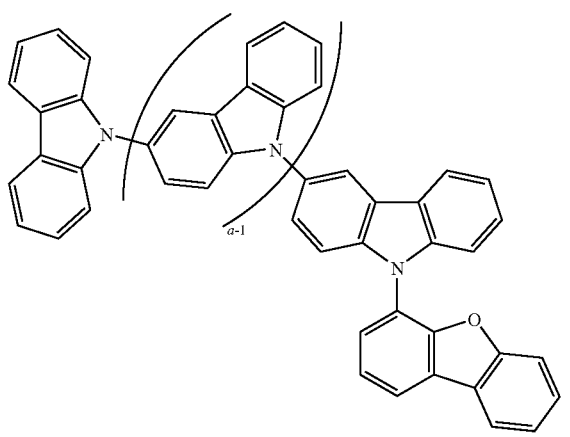
Compound 20G
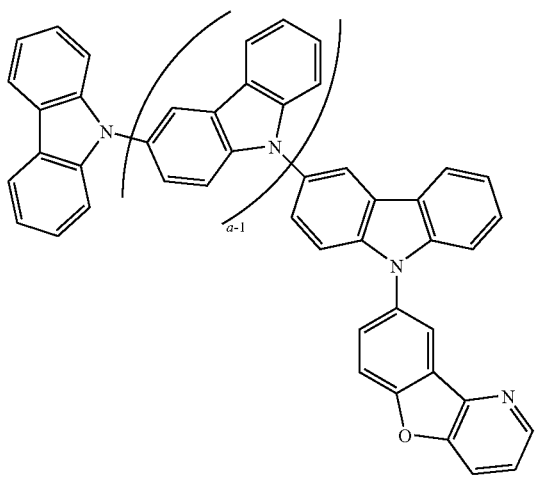
Compound 16G
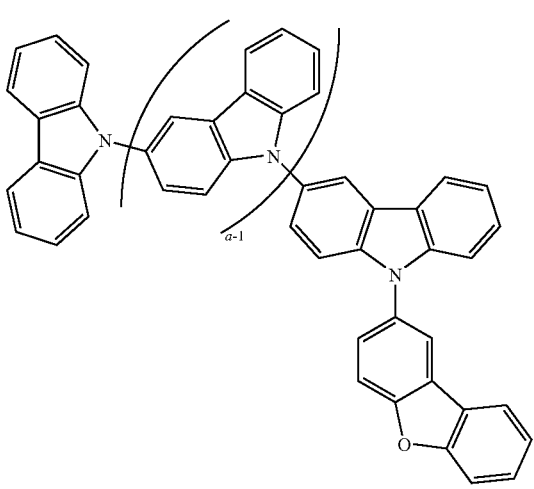
Compound 21G
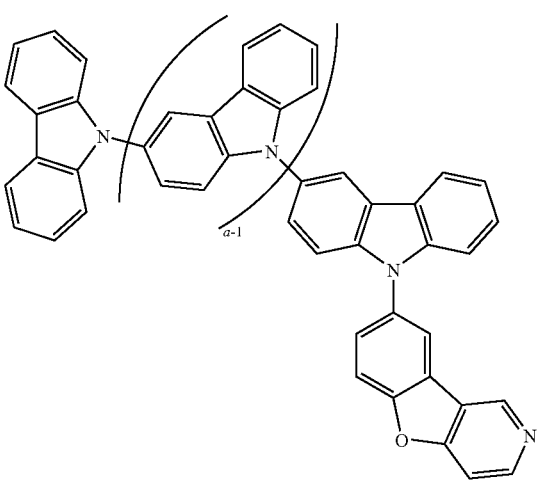

Compound 22G
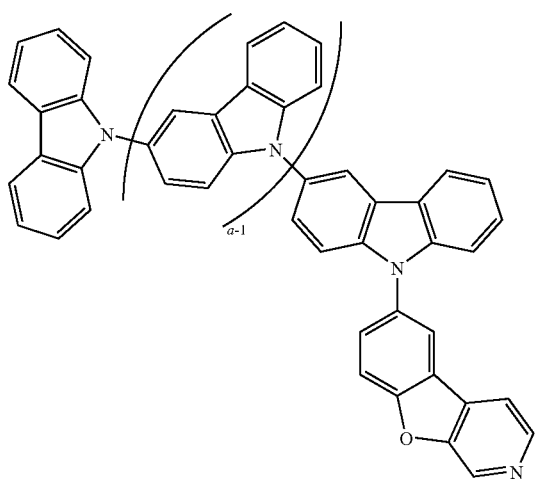
Compound 25G
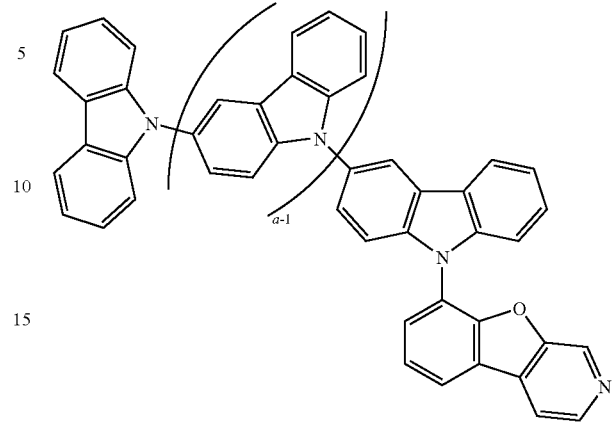
Compound 23G
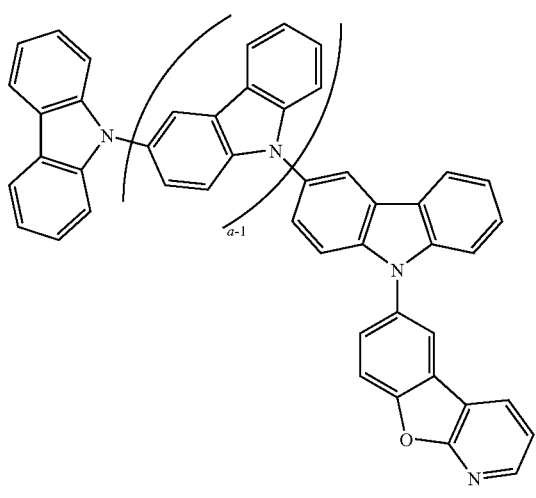
Compound 26G
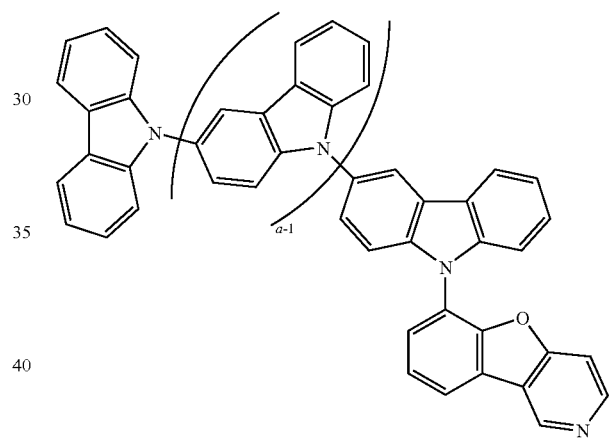
Compound 24G
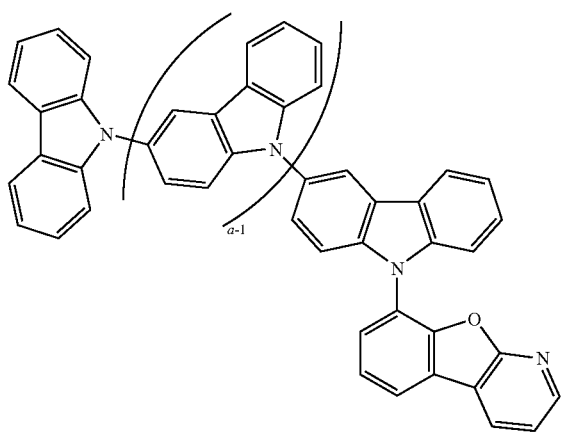
Compound 27G
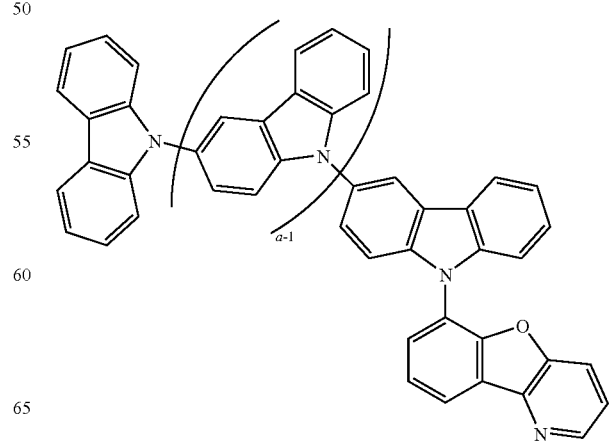

Compound 28G
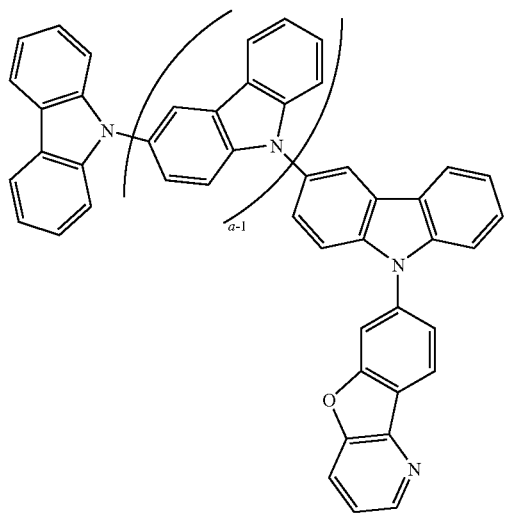
Compound 29G
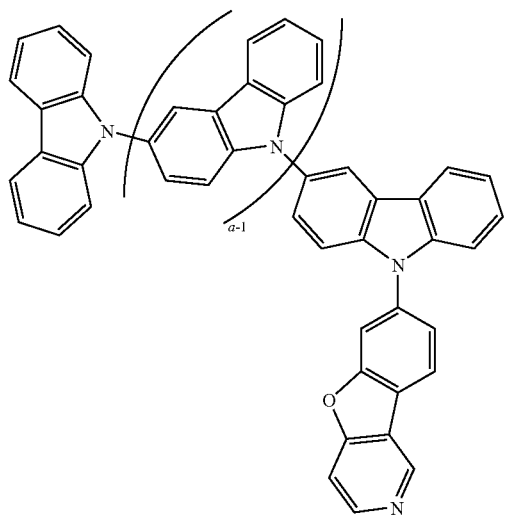
Compound 30G
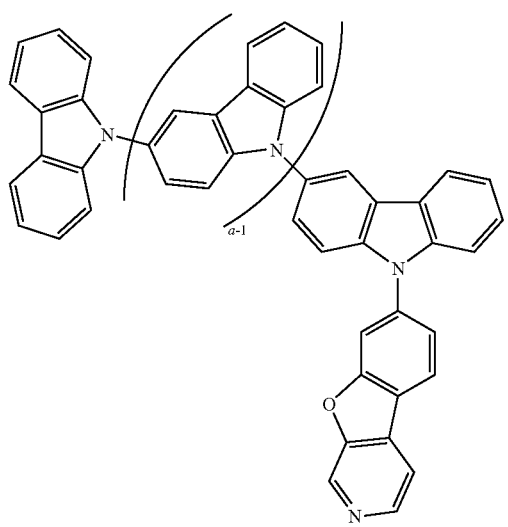
Compound 31G
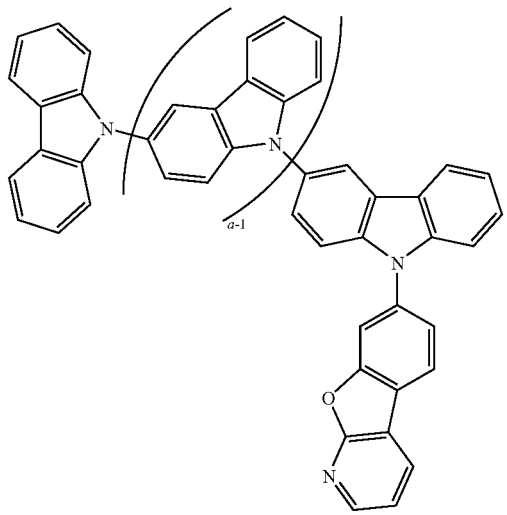
Compound 32G
Compound 33G -continued
Compound 34G
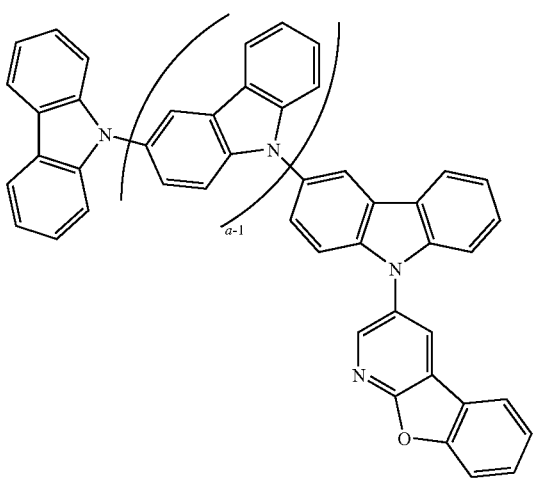
Compound 35G
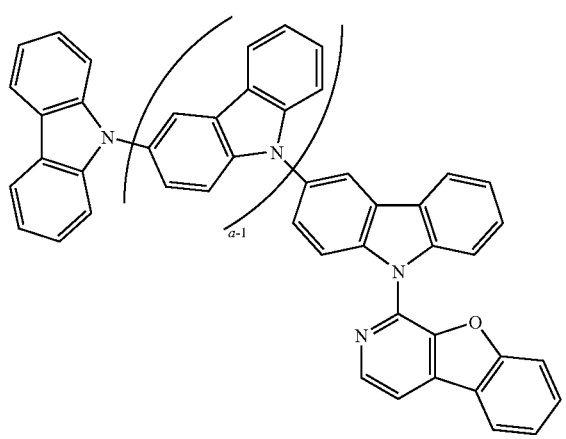
Compound 36G
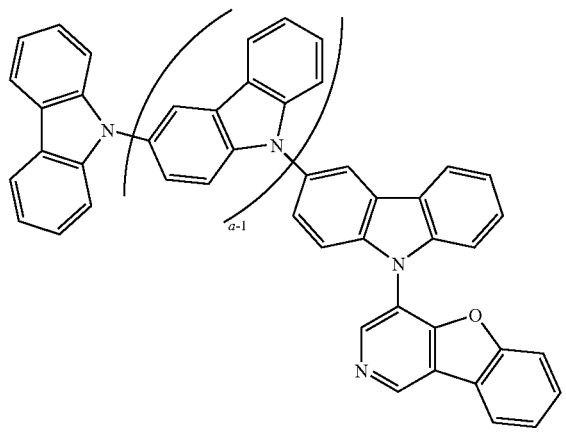
-continued
Compound 37G
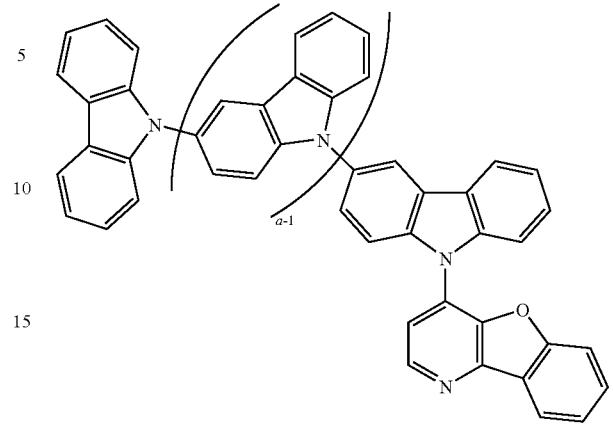
Compound 38G
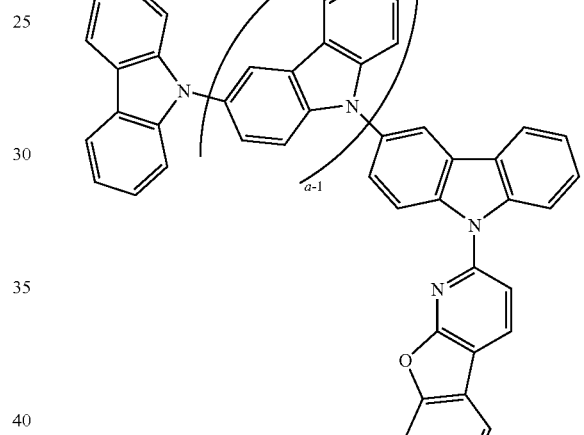
Compound 39G
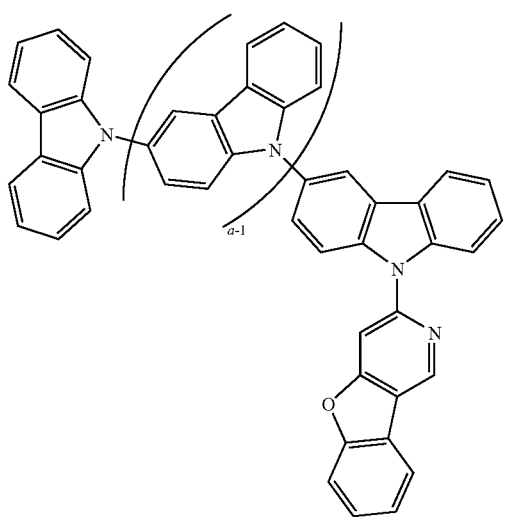

Compound 40G
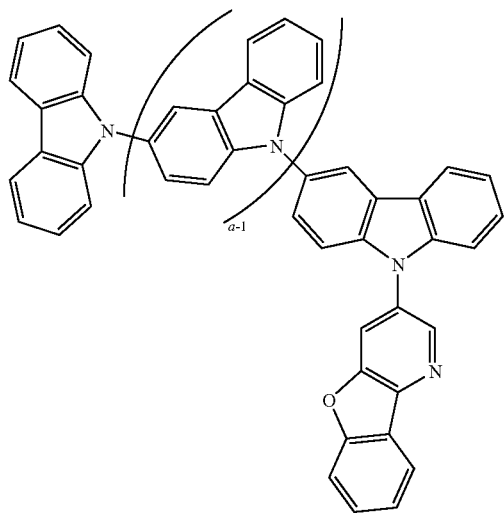
Compound 41G
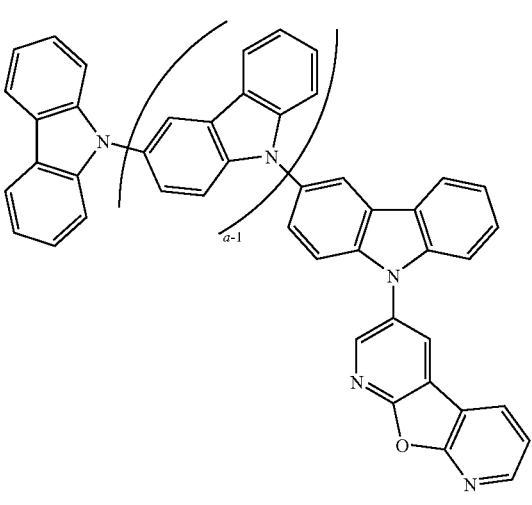
Compound 42G
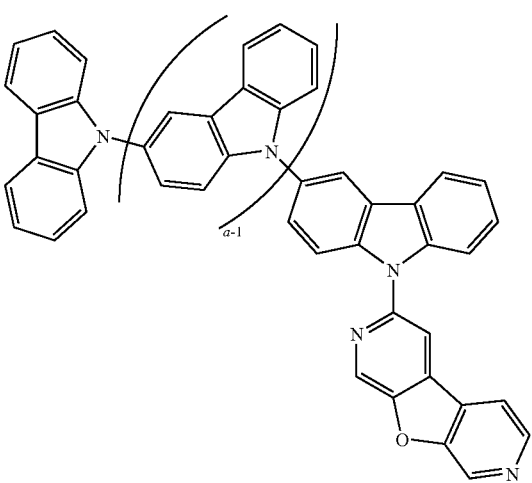
Compound 43G
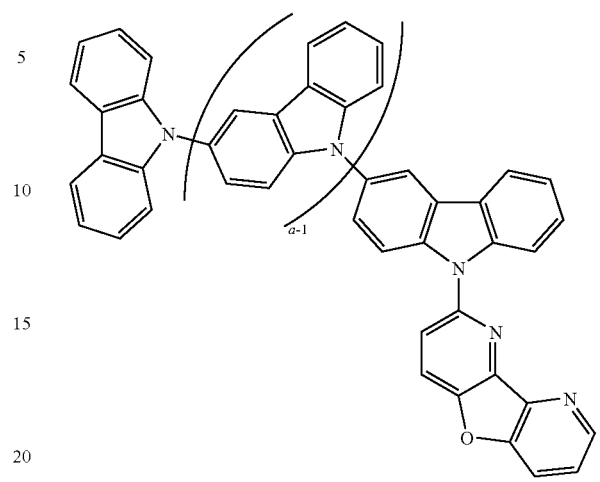
Compound 44G
Compound 45G
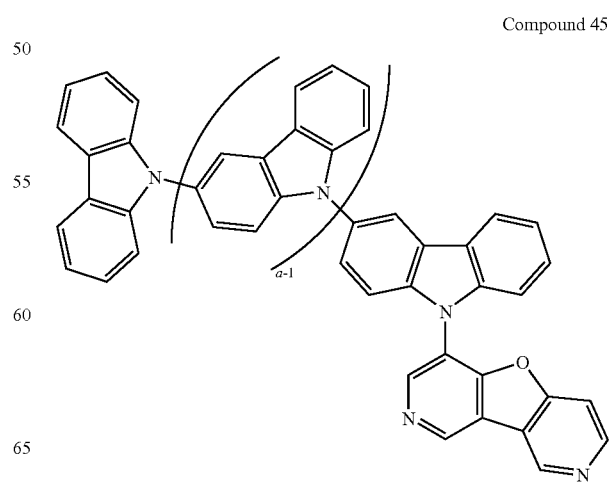

Compound 46G
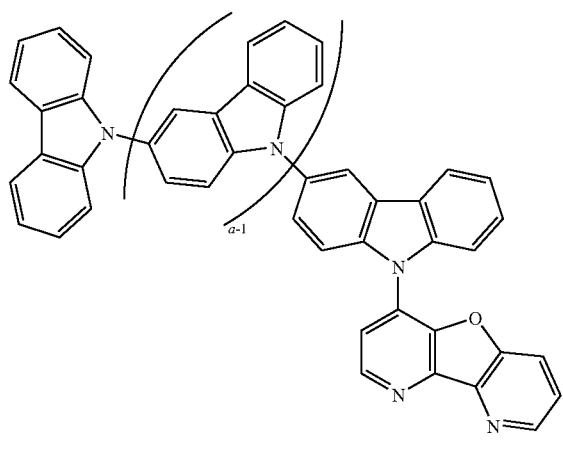
Compound 47G
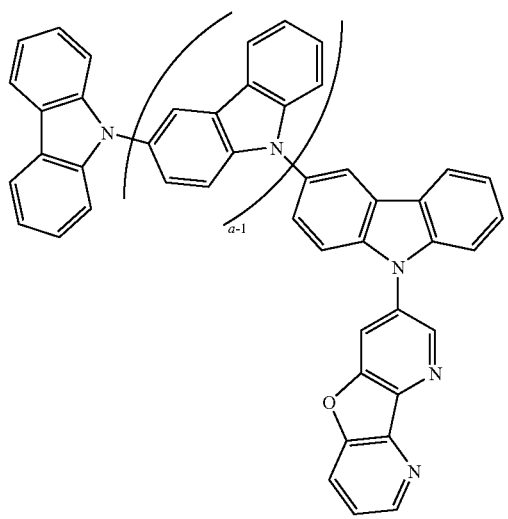
Compound 48G
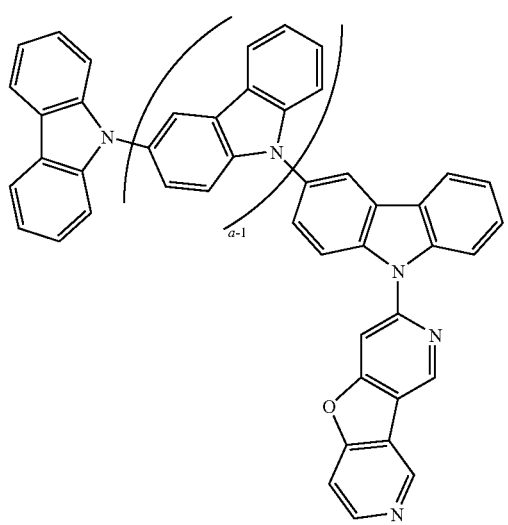
Compound 49G
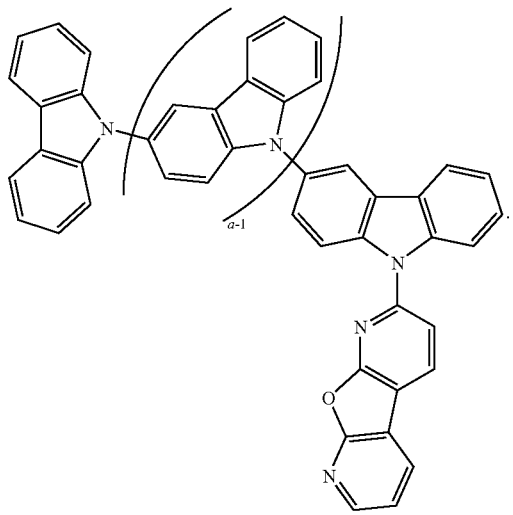
14. The compound of claim 11, wherein the compound is selected from the group consisting of:
Compound 6G
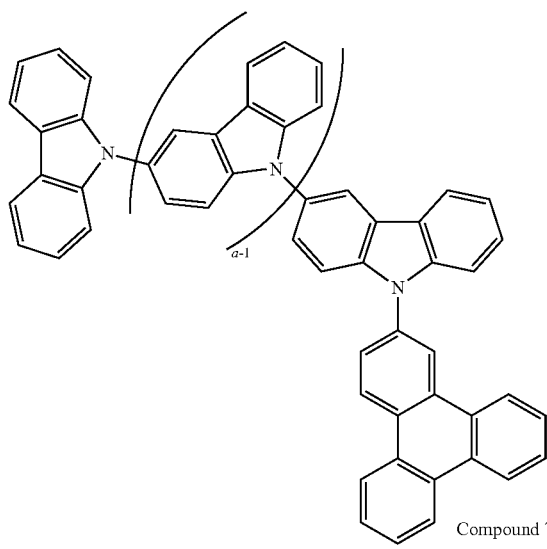
Compound 7G
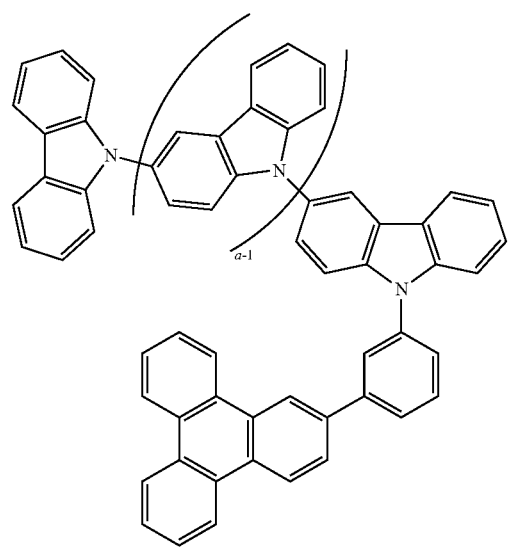

Compound 13G
Compound 3G
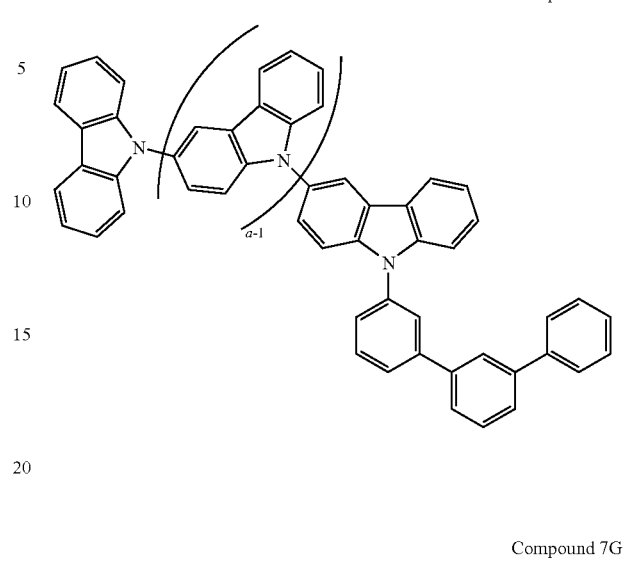
15. The compound of claim 11, wherein the compound is selected from the group consisting of:
Compound 1G
Compound 7G
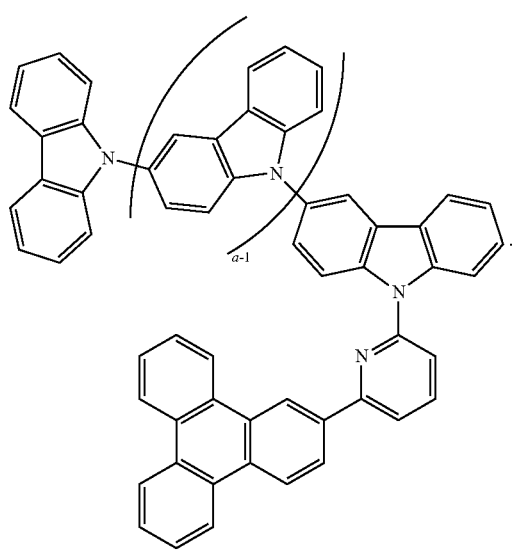
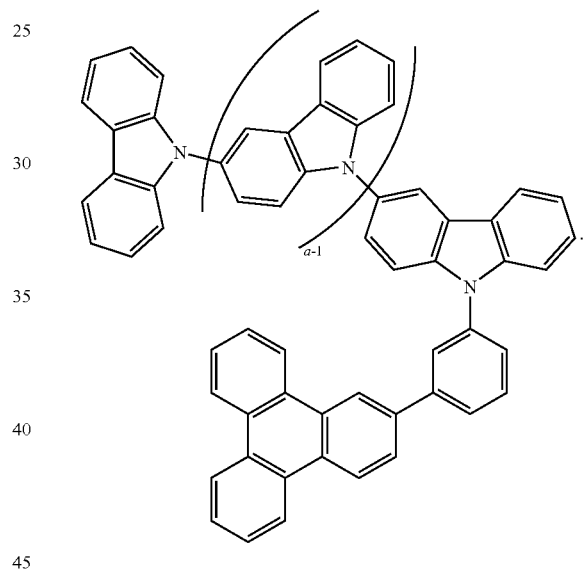
Compound 2G
16. The compound of claim 11, wherein the compound is selected from the group consisting of:
Compound 8G
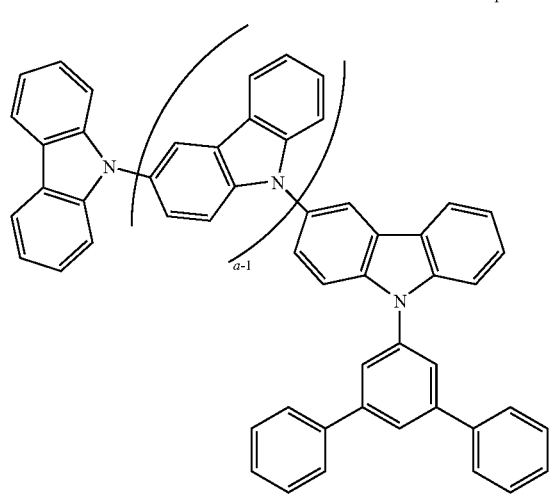
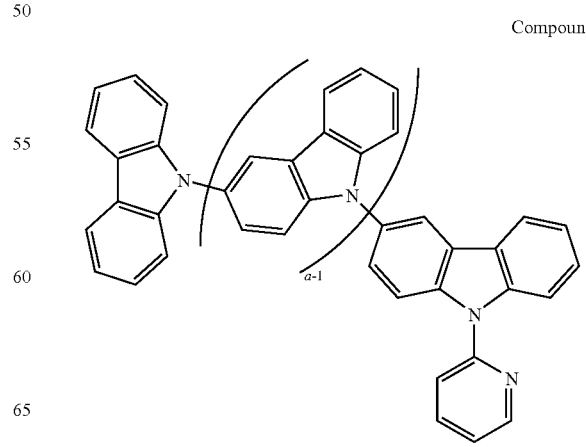

-continued
Compound 9G
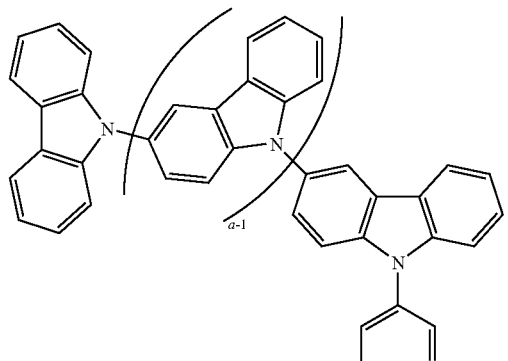
Compound 10G
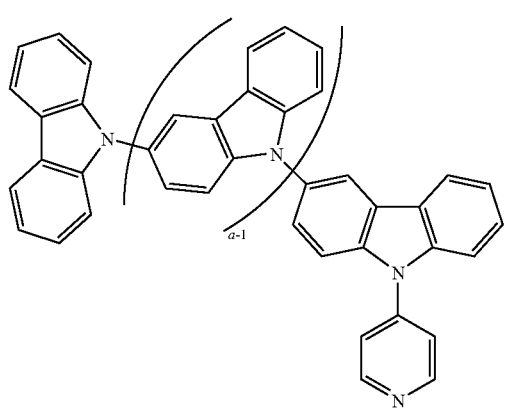
Compound 11G
Compound 12G
-continued
Compound 13G
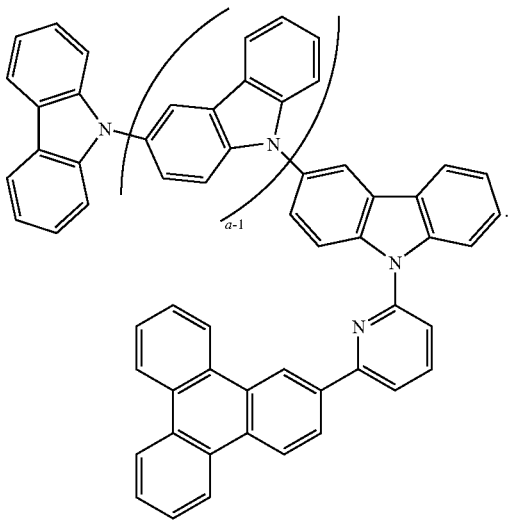
17. The compound of claim 11, wherein the compound is selected from the group consisting of:
Compound 4G
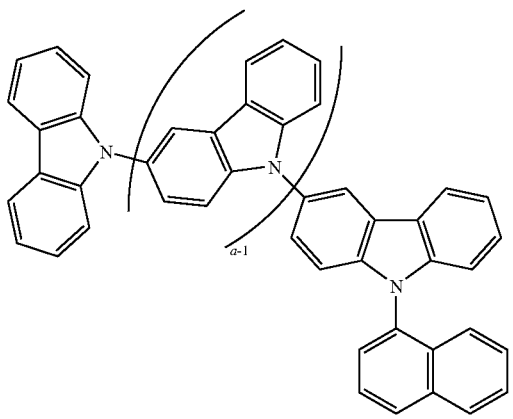
Compound 5G
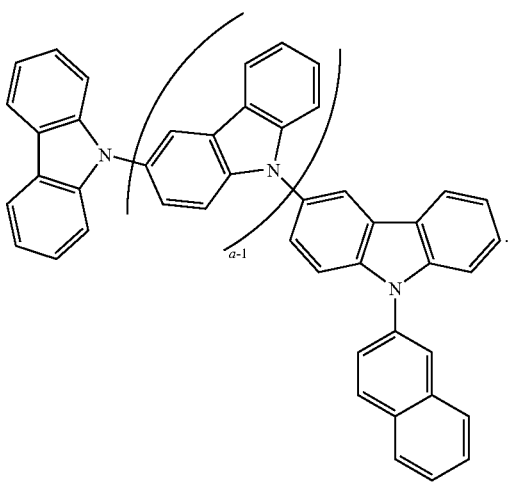
18. An organic light emitting device, comprising:
an anode;

a cathode; and a first organic layer disposed between the anode and the cathode, wherein the organic layer comprises a carbazole-containing compound, comprising

FORMULA I

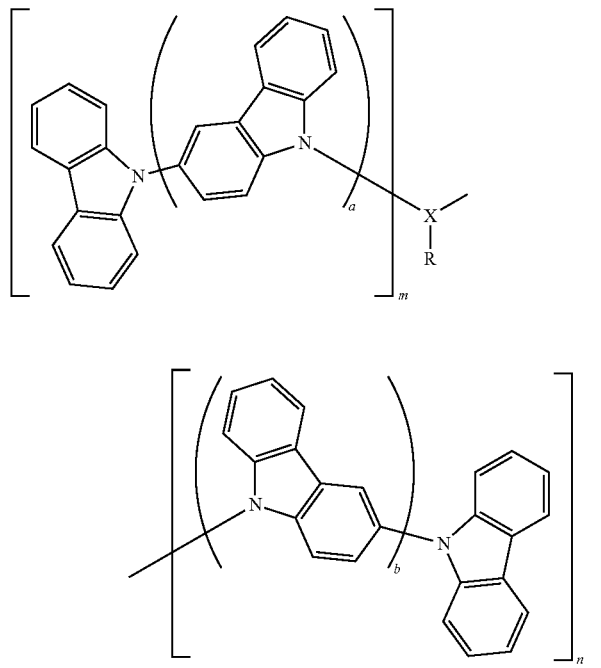

wherein a is 1 to 20;
wherein b is 0 to 20;
wherein m is 0 to 2;
wherein n is 0 to 2;
wherein m+n is at least 1;
wherein X is selected from the group consisting of biphenyl, terphenyl, naphthalene, triphenylene, phenanthrene, fluorene, chrysene, dibenzothiophene, dibenzofuran, benzofuran, benzothiophene, pyrazole, imidazole, triazole, oxazole, thiazole, oxadiazole, oxatriazole, dioxazole, thiadiazole, pyridine, pyridazine, pyrimidine, pyrazine, triazine, indole, benzimidazole, indazole, benzoxazole, benzisoxazole, benzothiazole, quinoline, isoquinoline, cinnoline, quinazoline, quinoxaline, naphthyridine, phthalazine, pteridine, xanthene, phenothiazine, phenoxazine, benzofuropyridine, furodipyridine, benzothienopyridine, and thienodipyridine; and
wherein X is substituted by R, where R is selected from the group consisting of hydrogen, alkyl, heteroalkyl, benzene, biphenyl, terphenyl, naphthalene, phenalene, phenanthrene, fluorene, chrysene, dibenzothiophene, dibenzofuran, benzofuran, benzothiophene, pyrazole, imidazole, triazole, oxazole, thiazole, oxadiazole, oxatriazole, dioxazole, thiadiazole, pyridine, pyridazine, pyrimidine, pyrazine, triazine, indole, benzimidazole, indazole, benzoxazole, benzisoxazole, benzothiazole, quinoline, isoquinoline, cinnoline, quinazoline, quinoxaline, naphthyridine, phthalazine, pteridine, xanthene, phenothiazine, phenoxazine, benzofuropyridine, furodipyridine, benzothienopyridine, and thienodipyridine.

19. The device of claim 18, wherein the carbazole-containing compound is selected from the group consisting of:

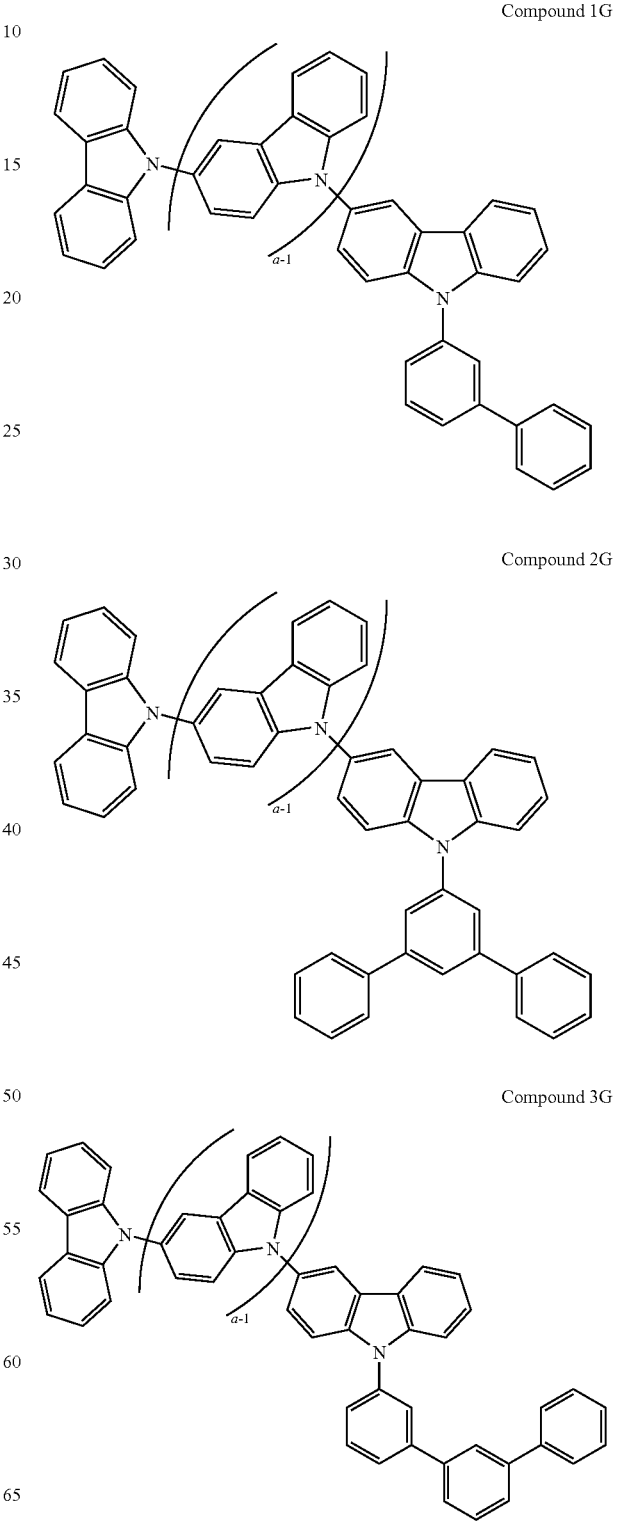

Compound 4G
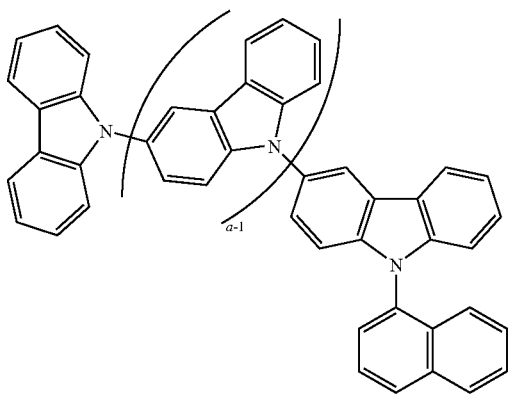
Compound 5G
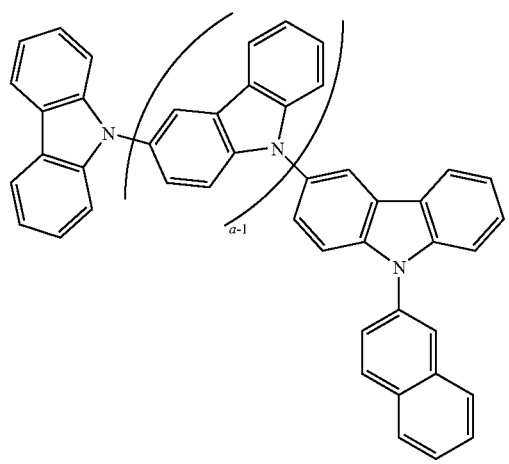
Compound 6G
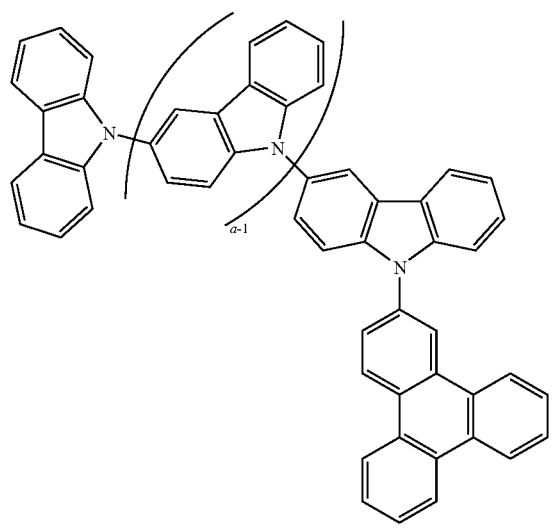
Compound 7G
Compound 8G
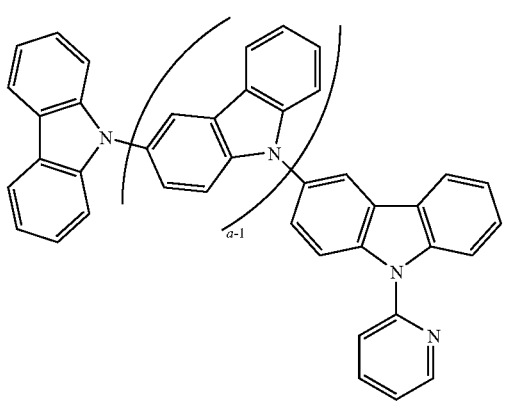
Compound 9G
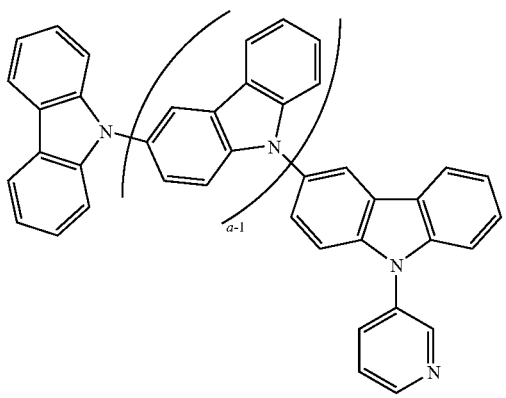

Compound 10G
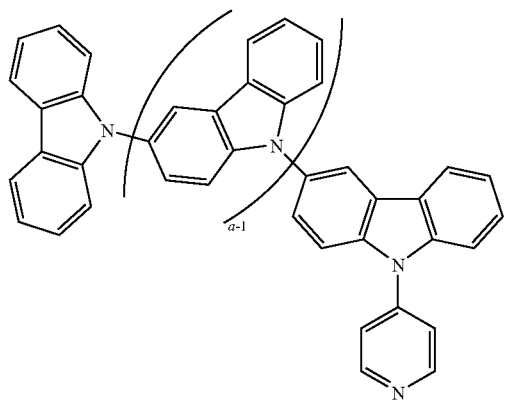
Compound 11G
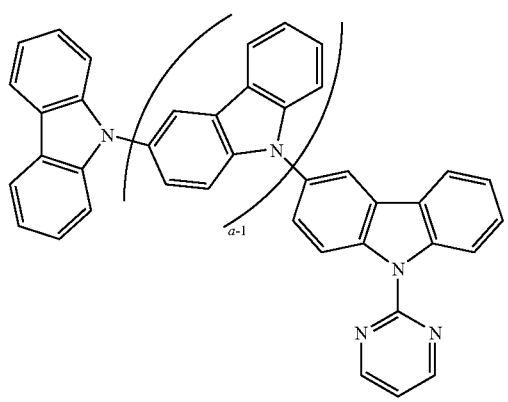
Compound 12G
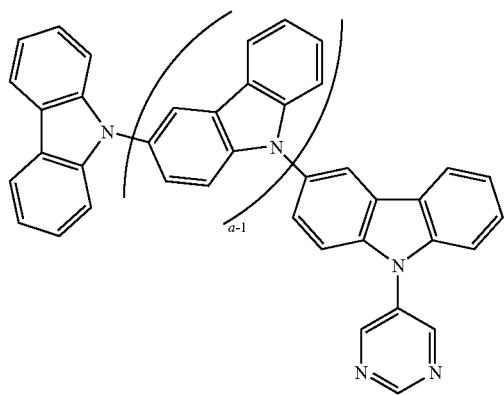
Compound 13G
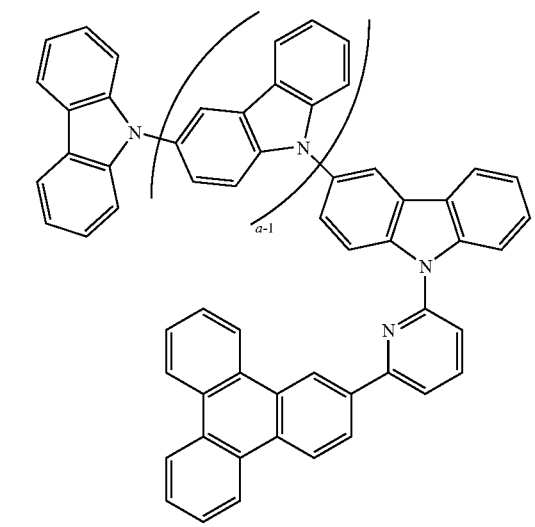
Compound 14G
Compound 15G
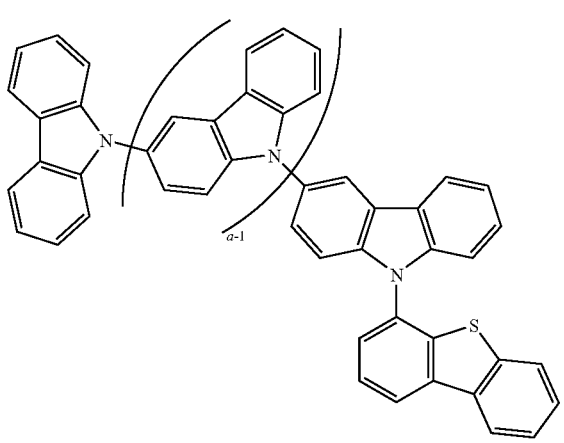

Compound 16G
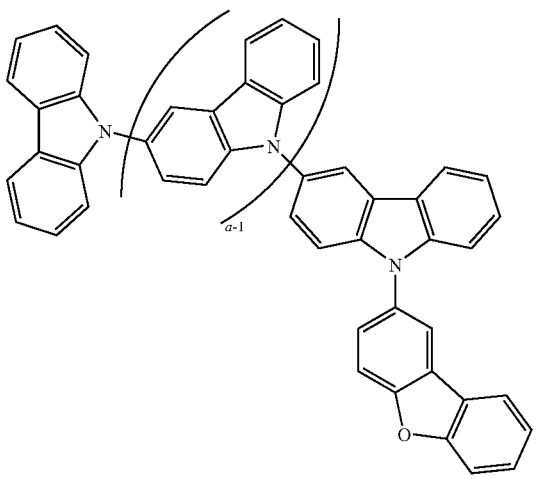
Compound 19G
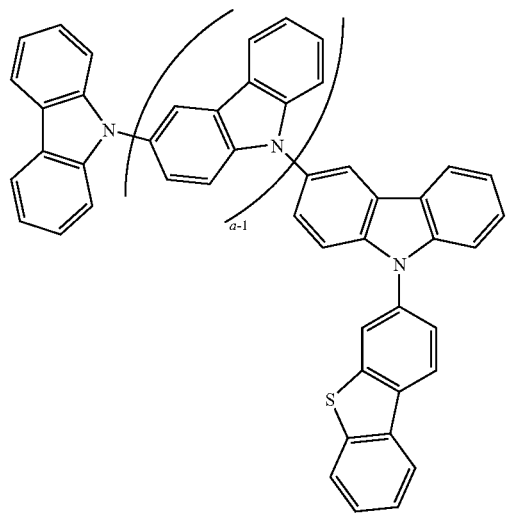
Compound 17G
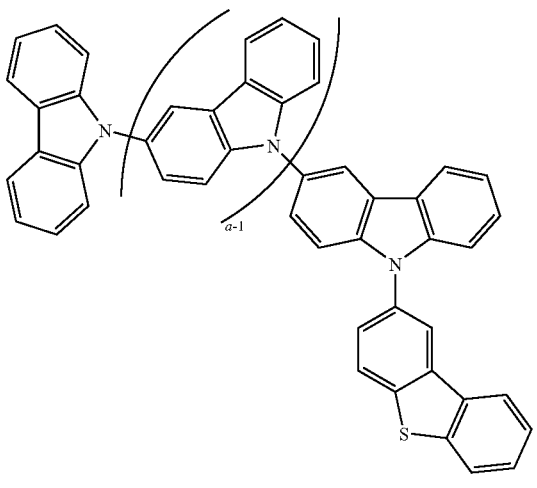
Compound 20G
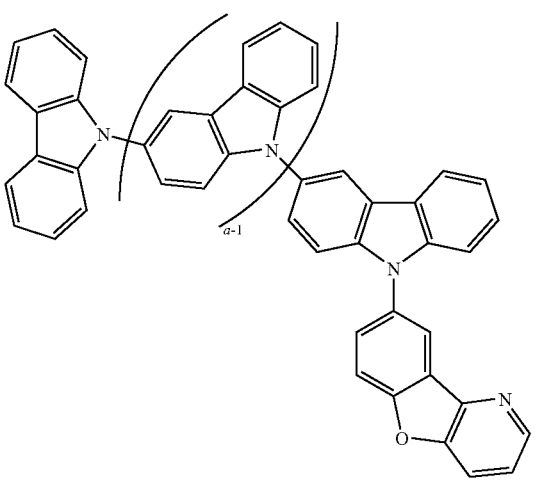
Compound 18G
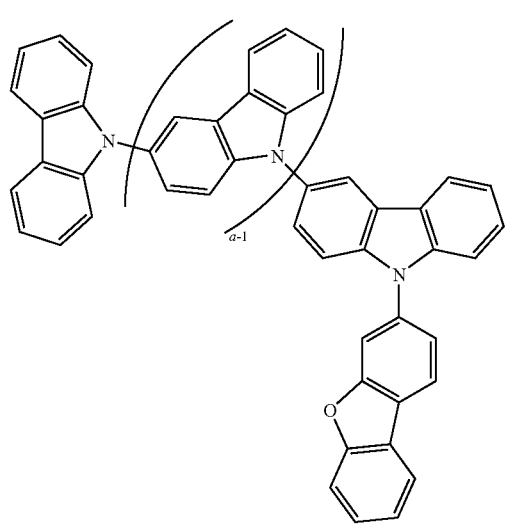
Compound 21G
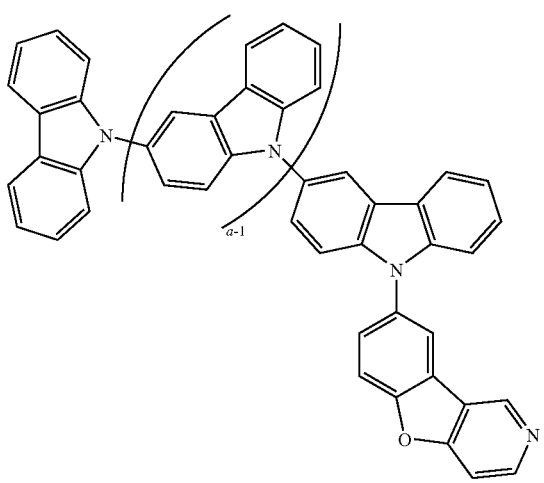

-continued
Compound 22G
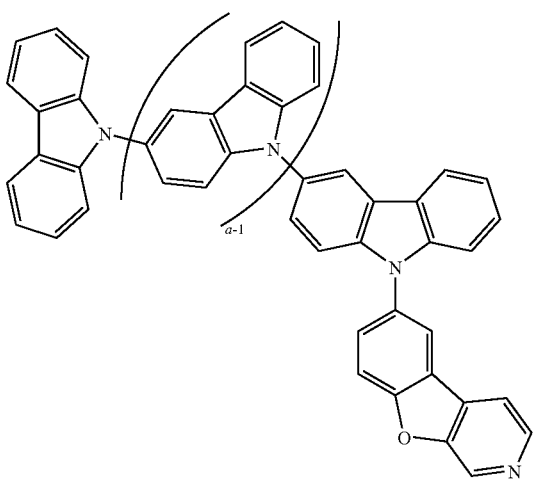
Compound 23G
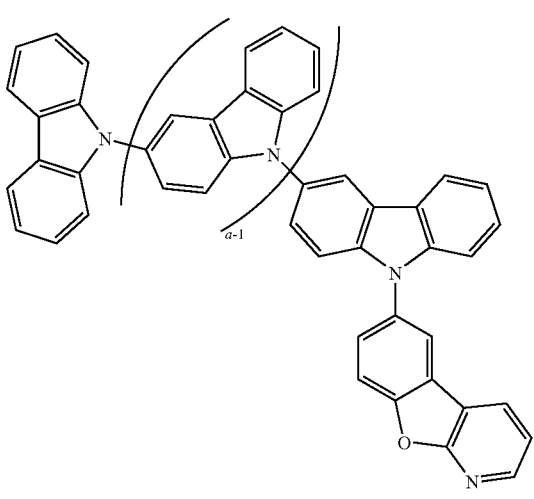
Compound 24G
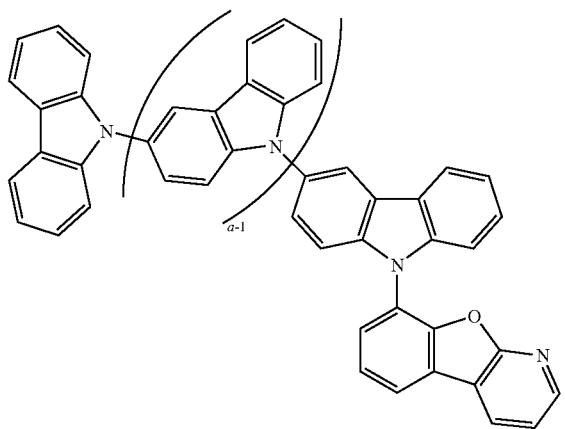
-continued
Compound 25G
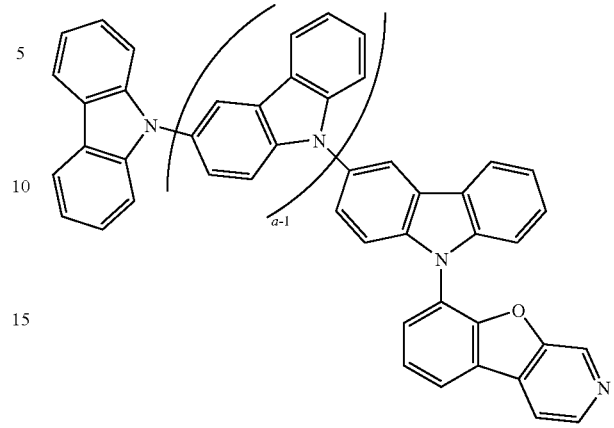
Compound 26G
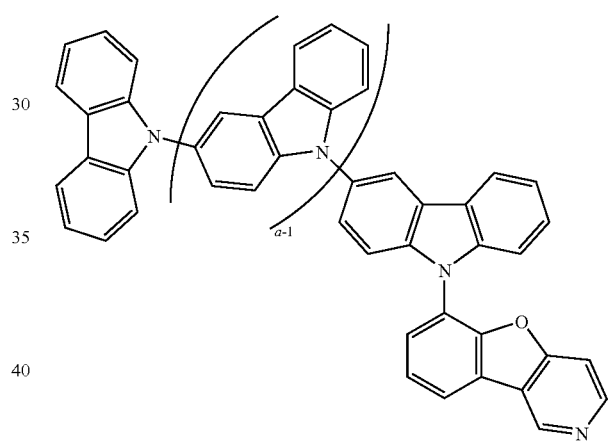
Compound 27G
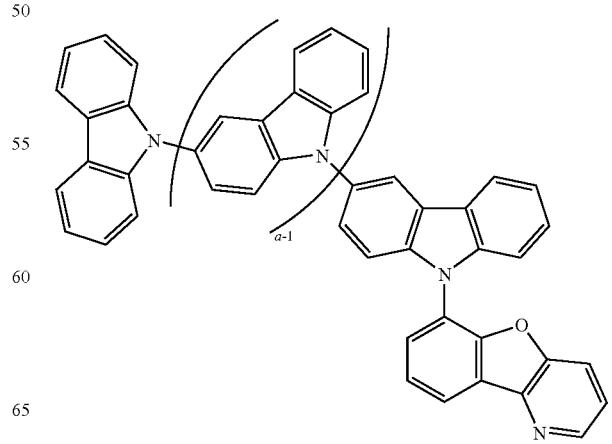

Compound 28G
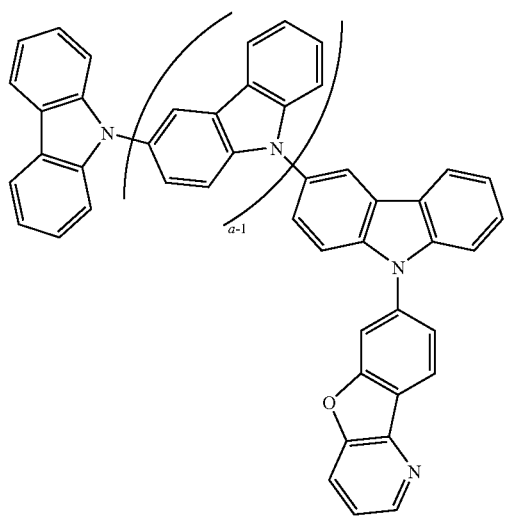
Compound 31G
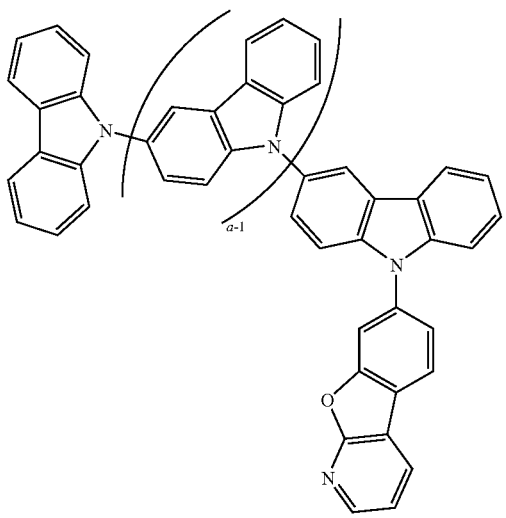
Compound 29G
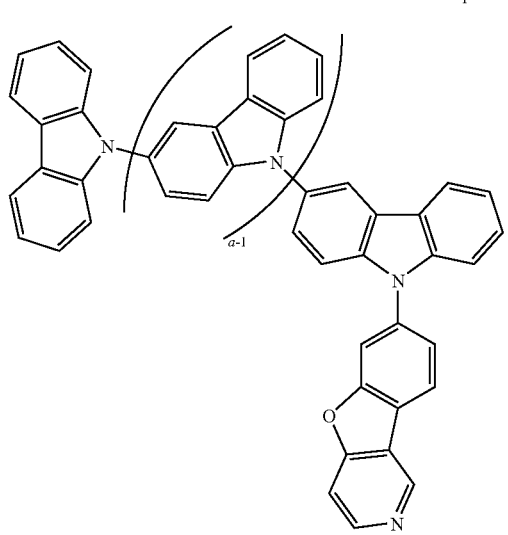
Compound 32G
Compound 30G
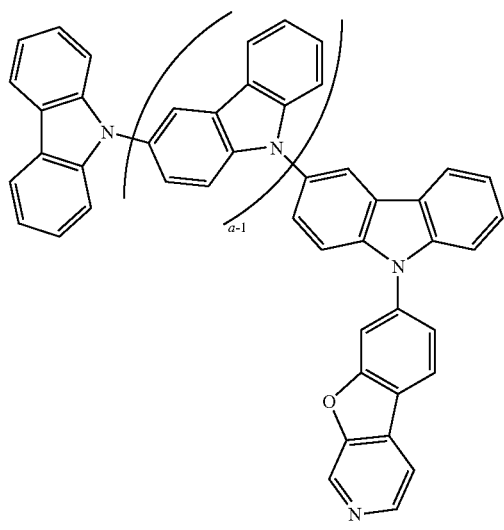
Compound 33G
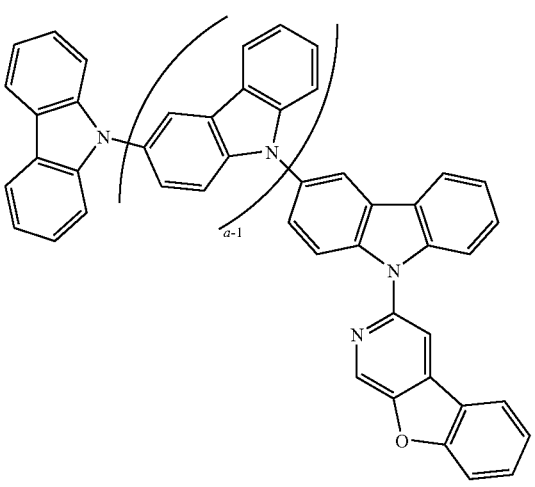

Compound 34G
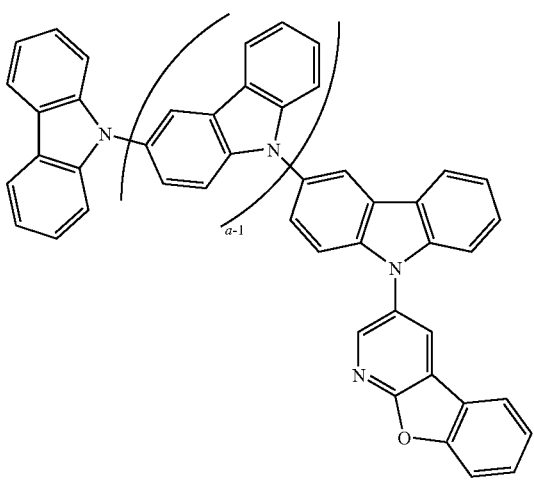
Compound 35G
Compound 36G
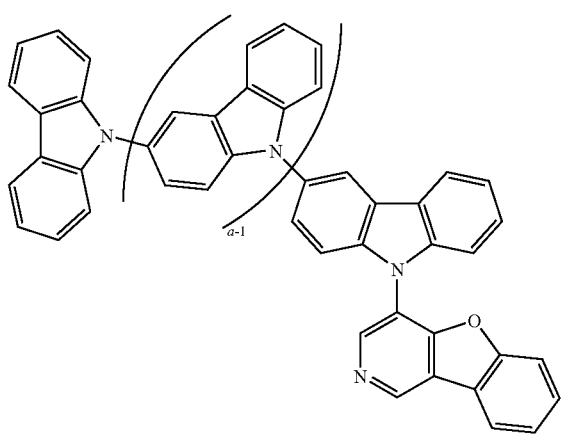
Compound 37G
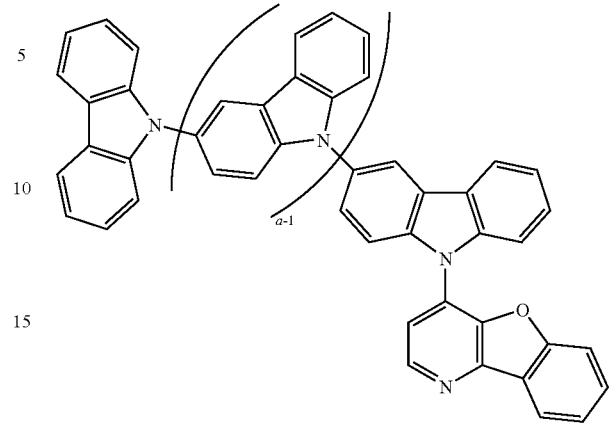
Compound 38G
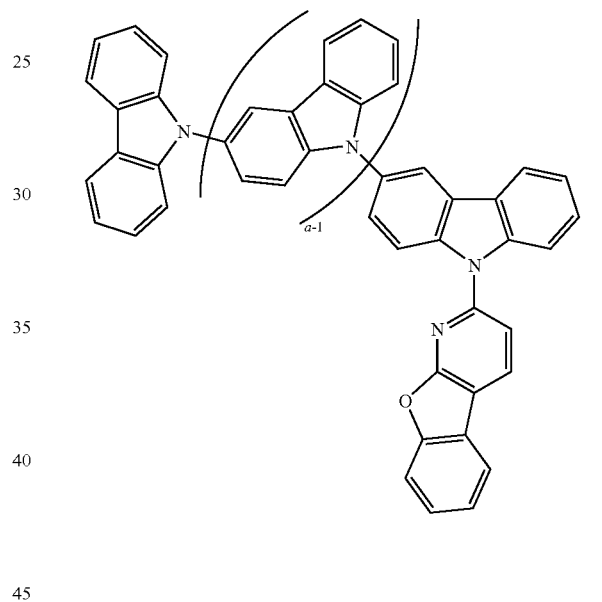
Compound 39G
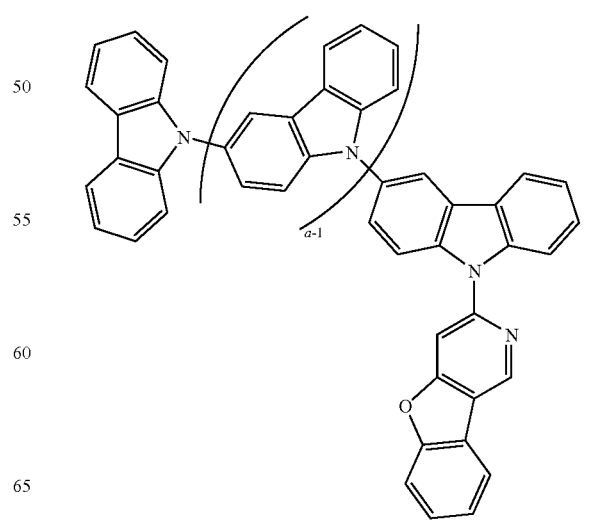

Compound 40G
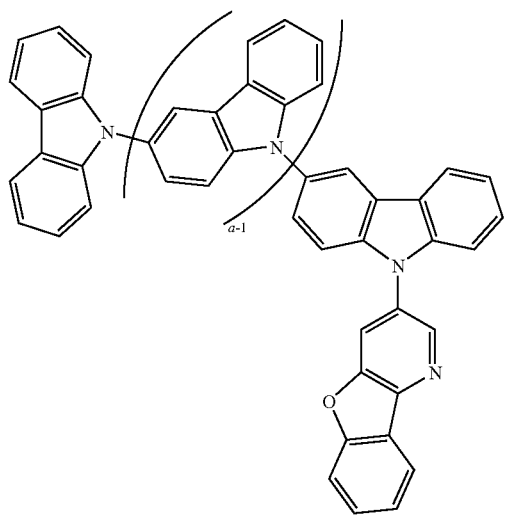
Compound 41G
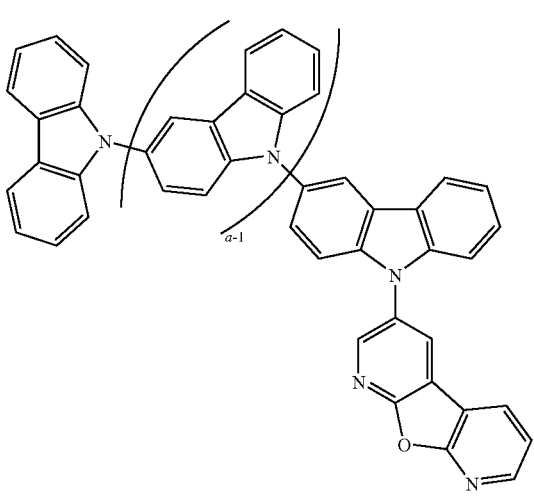
Compound 42G
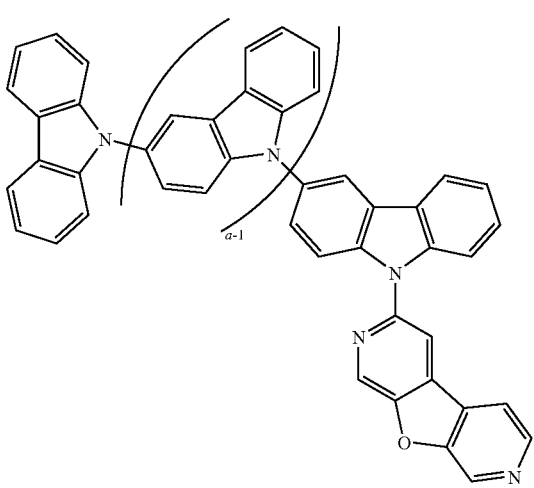
Compound 43G
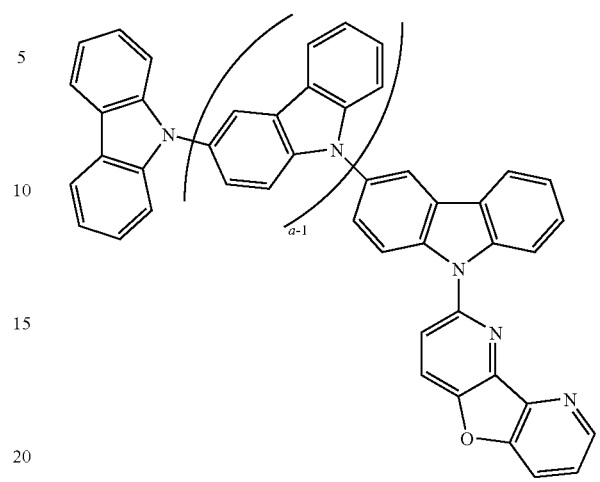
Compound 44G
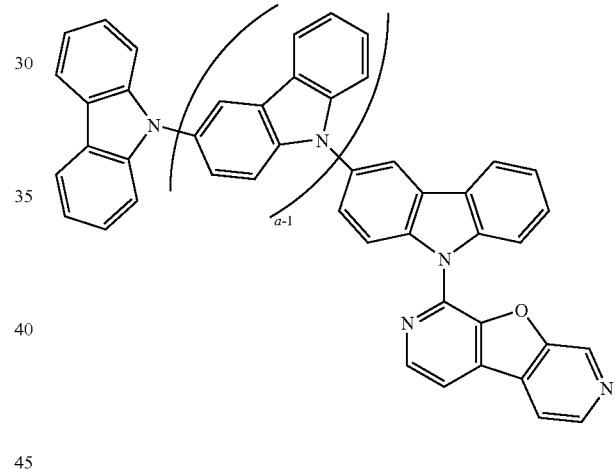
Compound 45G
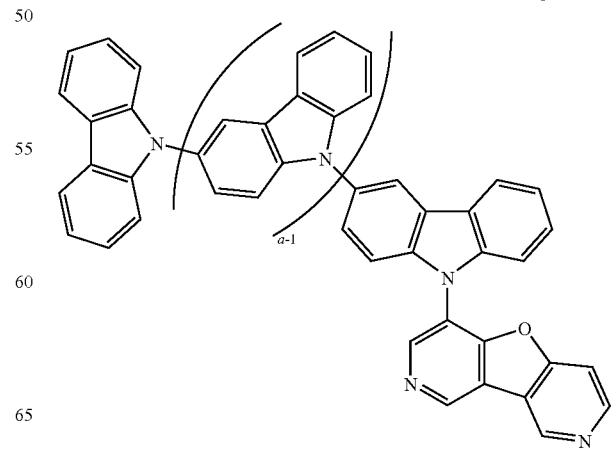

Compound 46G
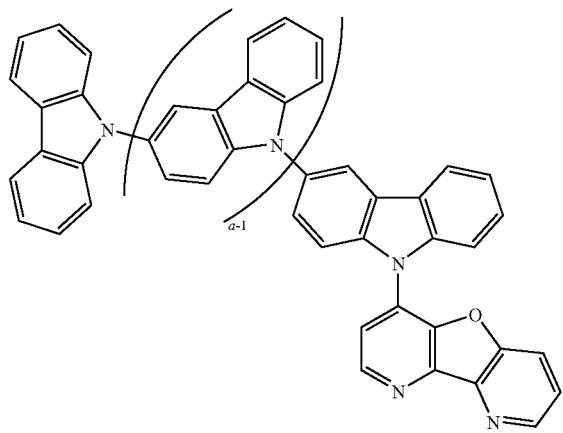
Compound 47G
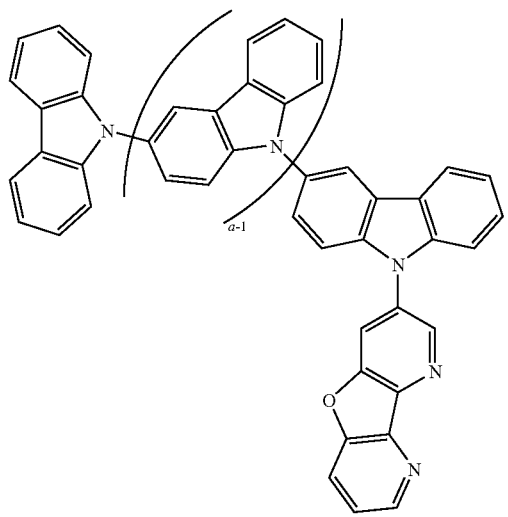
Compound 48G
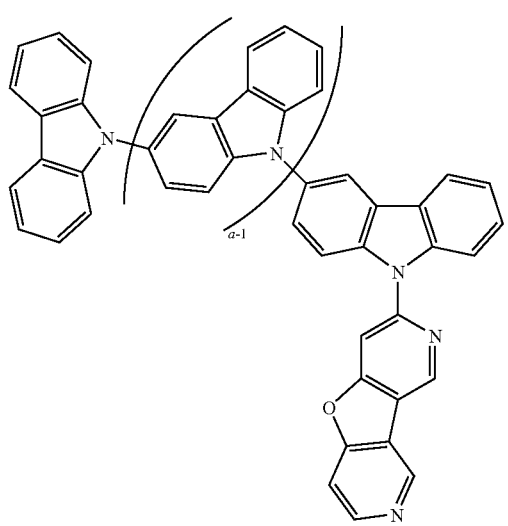
Compound 49G
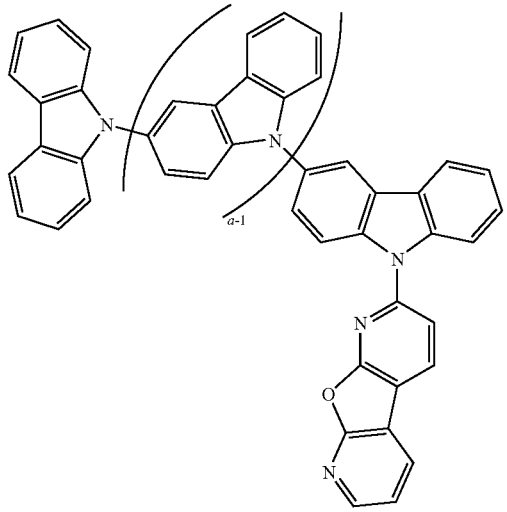
Compound 50G
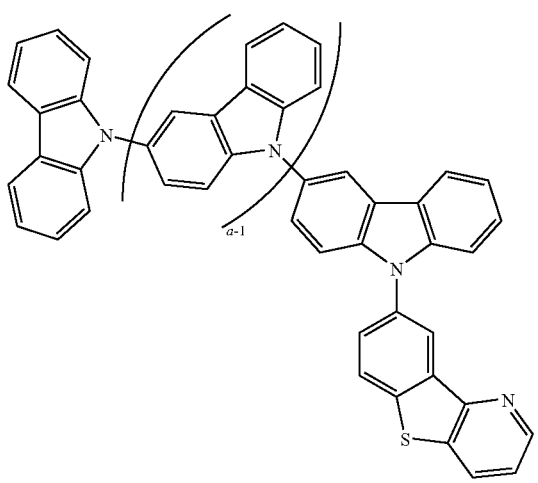
Compound 51G
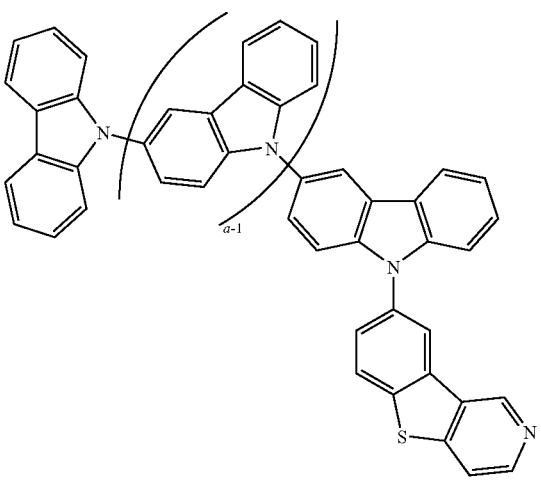

Compound 52G
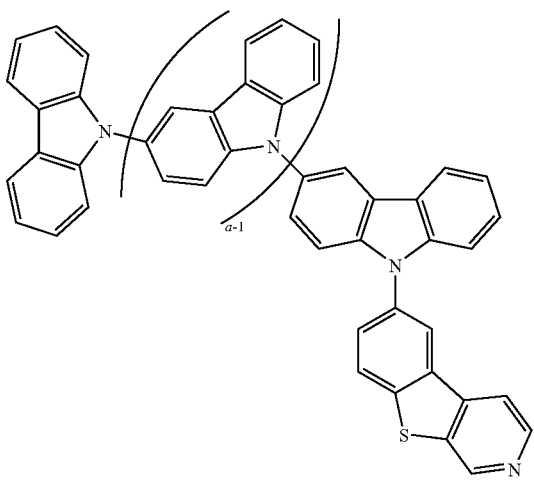
Compound 55G
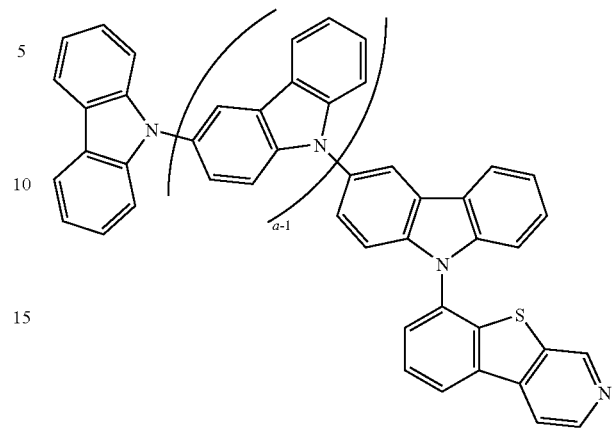
Compound 53G
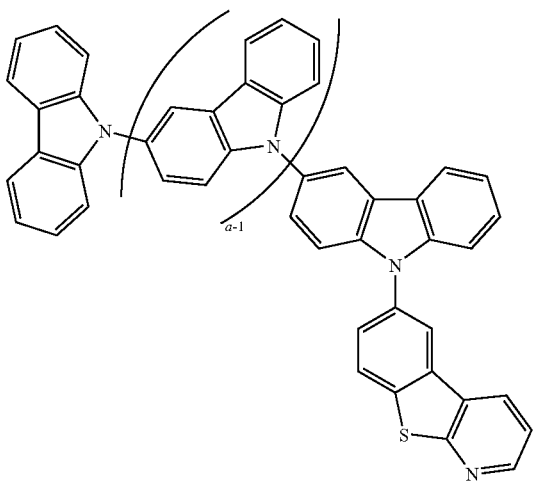
Compound 56G
Compound 54G
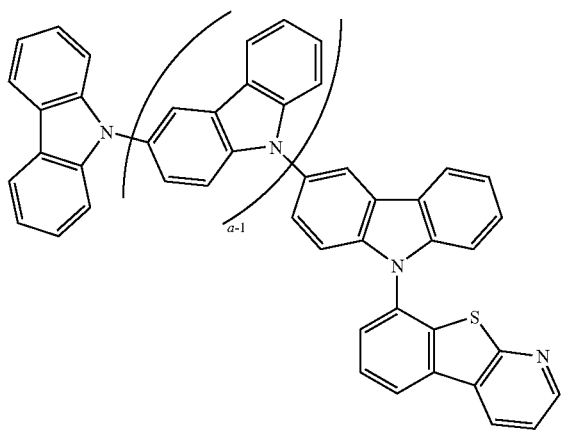
Compound 57G
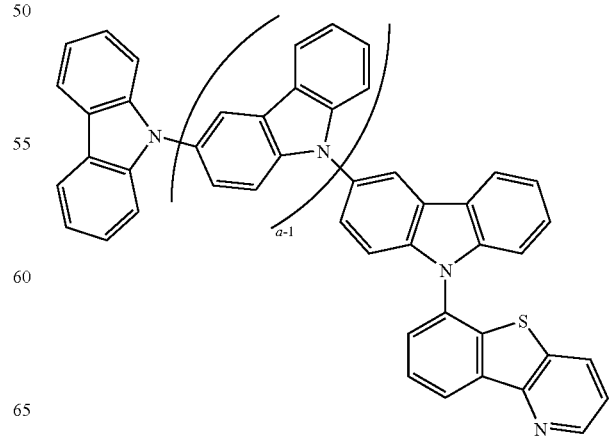

Compound 58G
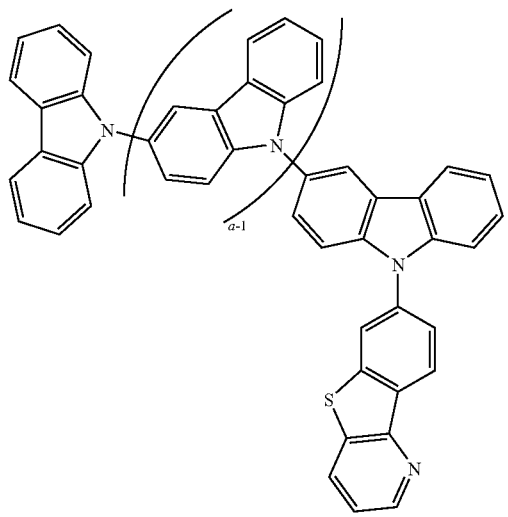
Compound 59G
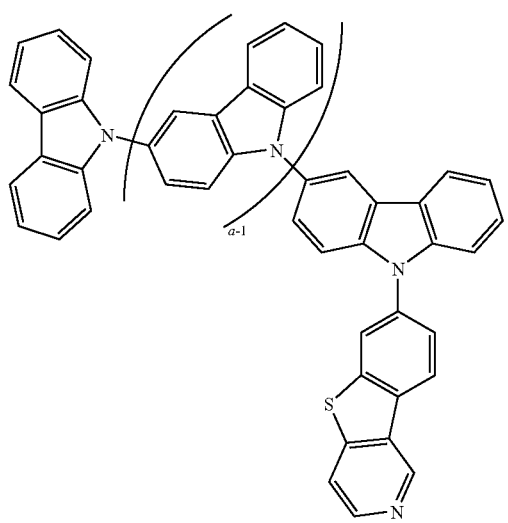
Compound 60G
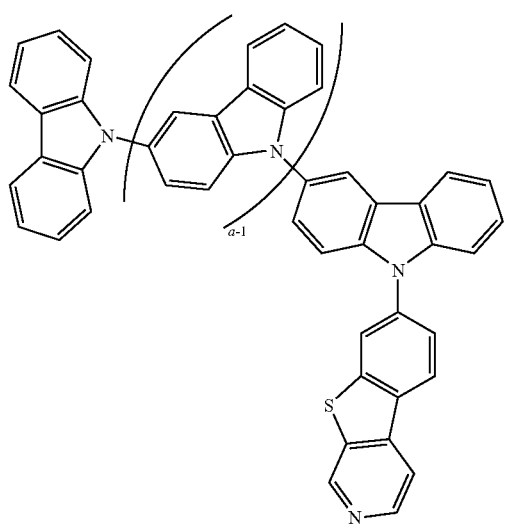
Compound 61G
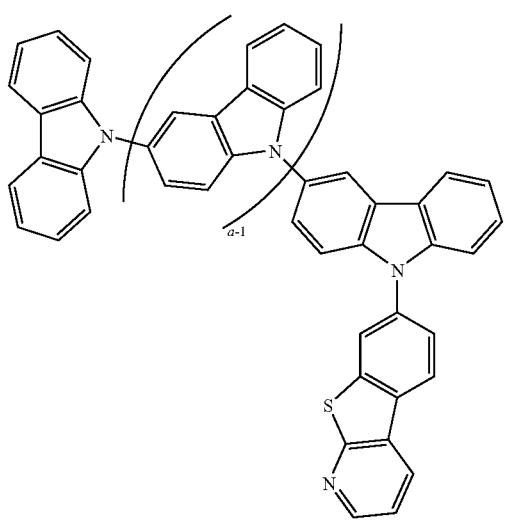
Compound 62G
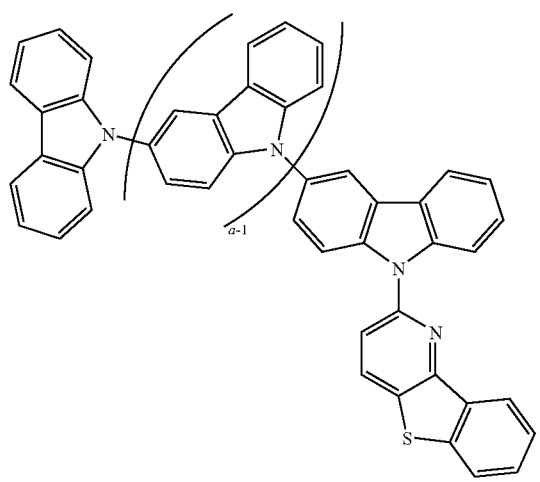
Compound 63G
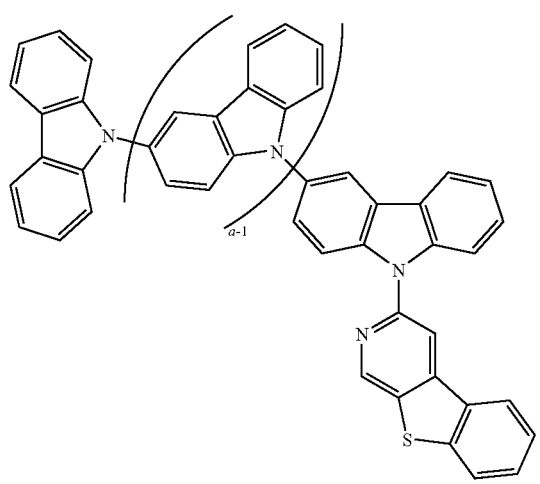

Compound 64G
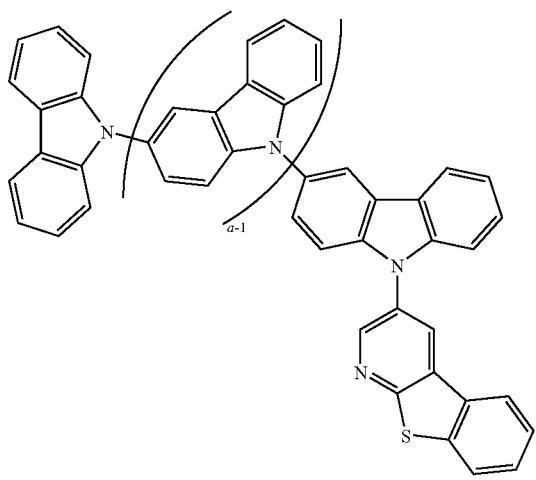
Compound 65G
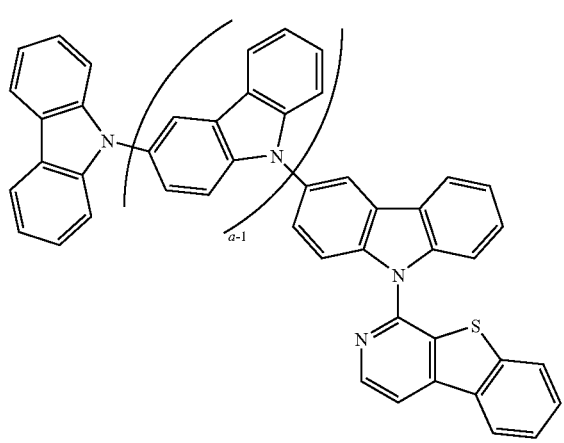
Compound 66G
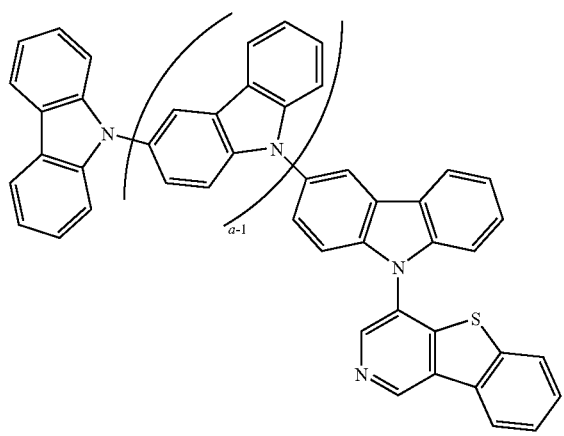
Compound 67G
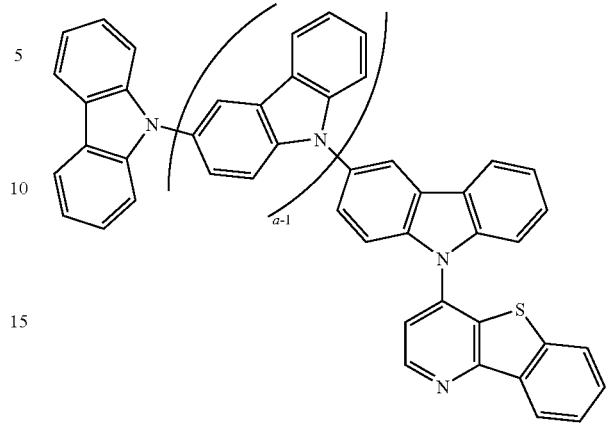
Compound 68G
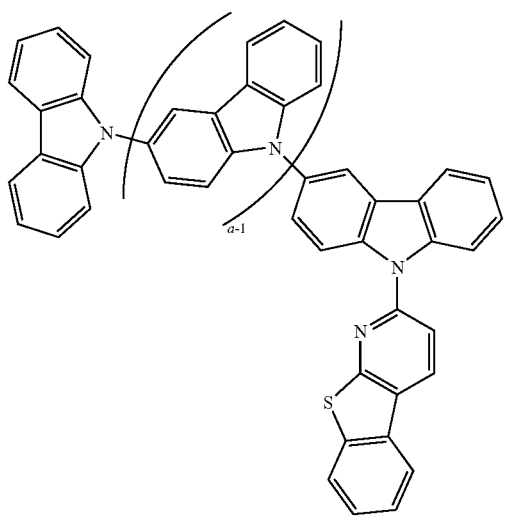
Compound 69G
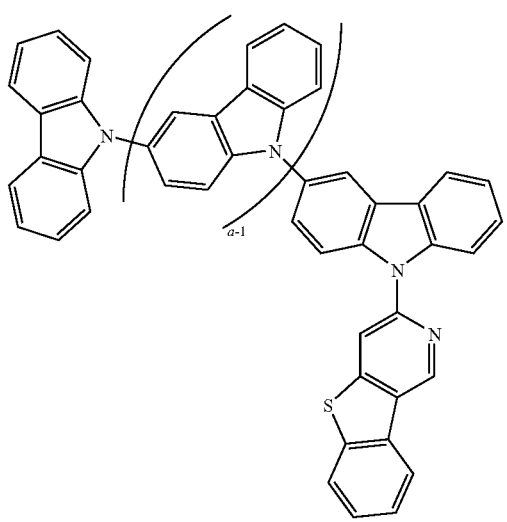

Compound 70G
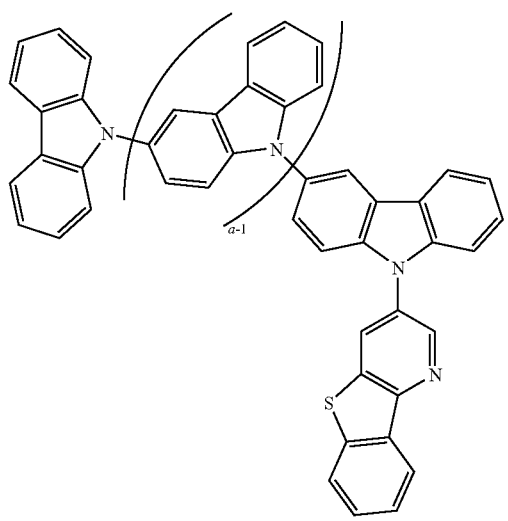
Compound 71G
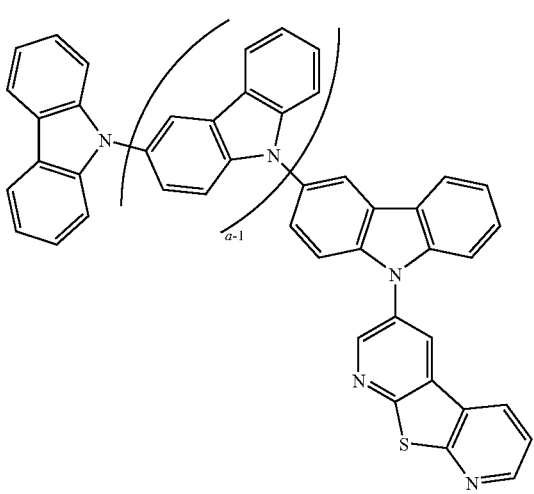
Compound 72G
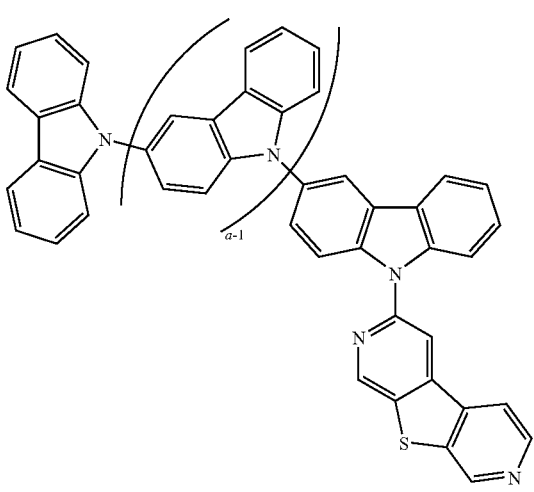
Compound 73G
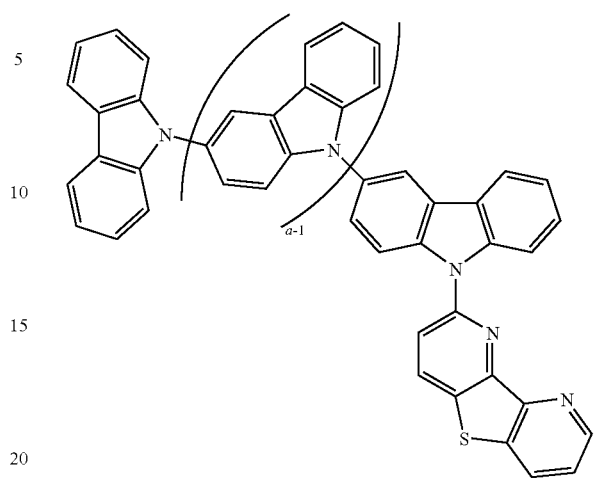
Compound 74G
Compound 75G Compound 76G

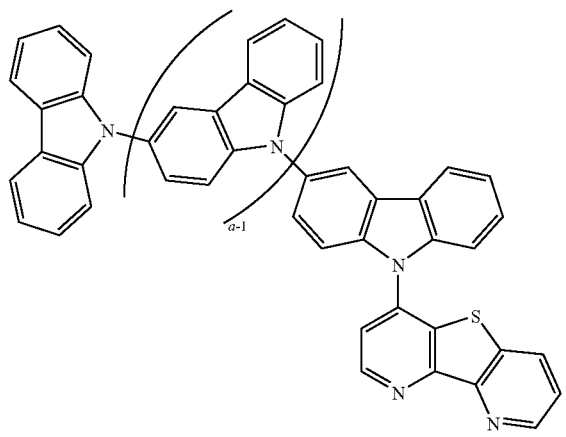

Compound 77G

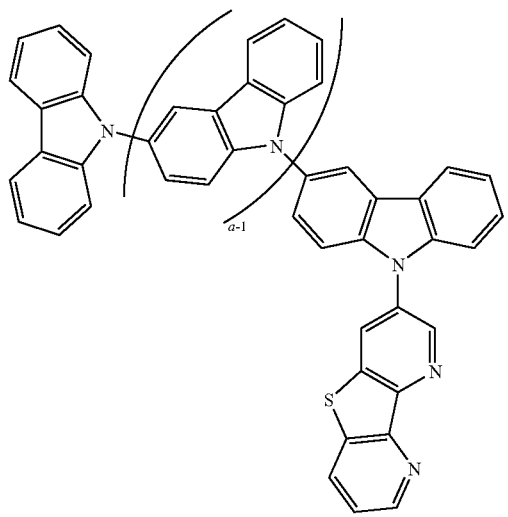

Compound 78G

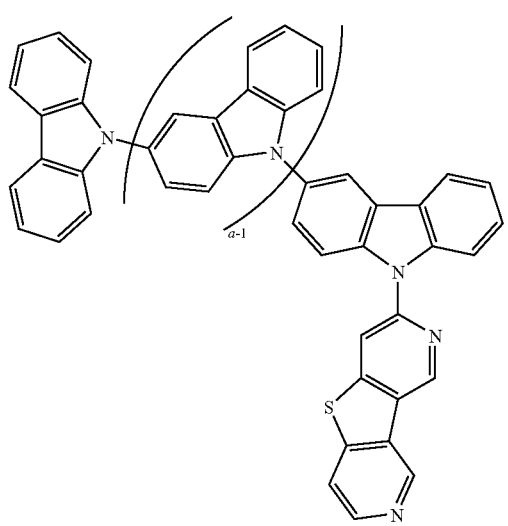

Compound 79G

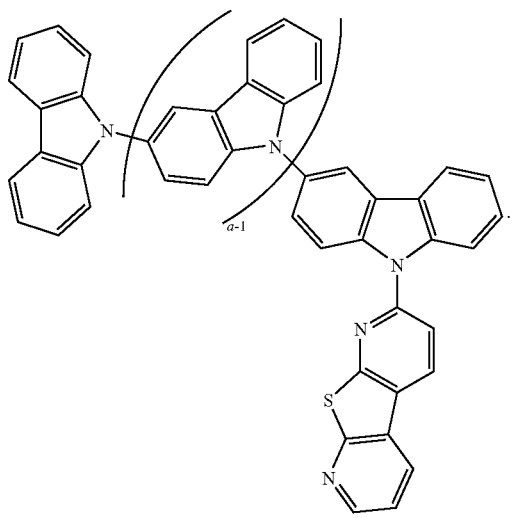

20. The device of claim 19, wherein the first organic layer is an emissive layer and the carbazole-containing compound is a host in the first organic layer.

21. The device of claim 20, wherein the emissive layer further comprises a phosphorescent emitter.

22. The device of claim 21, wherein the phosphorescent emitter is an iridium complex having the formula:

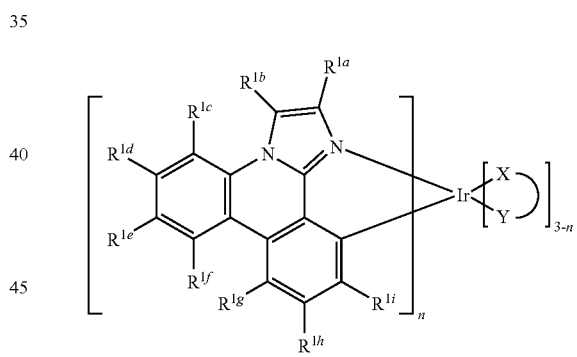

wherein n=1, 2 or 3;

wherein $R^{1a}$, $R^{1b}$, $R^{1c}$, $R^{1d}$, $R^{1e}$, $R^{1f}$, $R^{1g}$, $R^{1h}$, and $R^{1i}$ are each, independently, H, hydrocarbyl, heteroatom substituted hydrocarbyl, cyano, fluoro, $OR^{2a}$, $SR^{2a}$, $NR^{2a}R^{2b}$, $BR^{2a}R^{2b}$, or $SiR^{2a}R^{2b}R^{2c}$, wherein $R^{2a-c}$ are each, independently, hydrocarbyl or heteroatom substituted hydrocarbyl, and wherein any two of $R^{1a-i}$ and $R^{2a-c}$ may be linked to form a saturated or unsaturated, aromatic or non-aromatic ring; and wherein X-Y is an ancillary ligand.

23. The device of claim 21, wherein the phosphorescent emitter is a compound comprising a phosphorescent metal complex comprising a monoanionic, bidentate ligand having the formula:

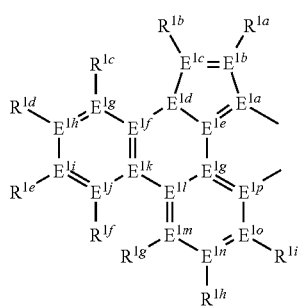

wherein $E^{1a-q}$ are selected from the group consisting of C and N and collectively comprise an 18 pi-electron system; provided that $E^{1a}$ and $E^{1p}$ are different;

wherein $R^{1a-i}$ are each, independently, H, hydrocarbyl, heteroatom substituted hydrocarbyl, cyano, fluoro, $OR^{2a}$, $SR^{2a}NR^{2a}R^{2b}$, $BR^{2a}$, $R^{2b}$, or $SiR^{2a}R^{2b}R^{2c}$, where $R^{2a-c}$ are each, independently, hydrocarbyl or heteroatom substituted hydrocarbyl, and where any two of $R^{1a-i}$ and $R^{2a-c}$ may be linked to form a saturated or unsaturated, aromatic or non-aromatic ring; provided that $R^{1a-i}$ is other than H when attached to N;

wherein the metal is selected from the group consisting of the non-radioactive metals with atomic numbers greater than 40; and wherein the bidentate ligand may be linked with other ligands to comprise a tridentate, tetradentate, pentadentate or hexadentate ligand.

24. The device of claim 20, wherein the device further comprises a second organic layer that is a non-emissive layer.

25. The device of claim 24, wherein the first organic layer is adjacent to the second organic layer.

26. The device of claim 21, wherein the phosphorescent emitter has a triplet energy of 425 nm to 495 nm, X is selected from dibenzothiophene, dibenzofuran, benzofuropyridine, furodipyridine, benzothienopyridine, thienodipyridine, and triphenylene, and R is selected from hydrogen, alkyl, benzene, biphenyl, terphenyl, dibenzothiophene, dibenzofuran.

27. The device of claim 26, wherein the triplet energy is 440 nm to 480 nm.

28. The device of claim 21, wherein the phosphorescent emitter has a triplet energy of 495 nm to 570 nm, X is selected from biphenyl, terphenyl, triphenylene, phenanthrene, fluorene, dibenzothiophene, dibenzofuran, pyridine, pyridazine, pyrimidine, pyrazine, triazine, benzimidazole, benzothiazole, quinoline, isoquinoline, benzofuropyridine, furodipyridine, benzothienopyridine, and thienodipyridine, and R is selected from hydrogen, alkyl, benzene, biphenyl, terphenyl, triphenylene, phenanthrene, fluorene, dibenzothiophene, dibenzofuran, pyridine, pyridazine, pyrimidine, pyrazine, triazine, benzimidazole, benzothiazole, quinoline, isoquinoline, benzofuropyridine, furodipyridine, benzothienopyridine, and thienodipyridine.

29. The device of claim 28, wherein the triplet energy is 510 nm to 530 nm.

30. The device of claim 18, wherein the oligocarbazole-containing compound has a concentration of 10-100 wt %.

31. The device of claim 30, wherein the oligocarbazole-containing compound has a concentration of 40-99.9 wt %.

32. The device of claim 31, further comprising a phosphorescent emitter having a concentration of 0.1 to 30 wt %.

33. A consumer product comprising a device, the device further comprising:
an anode;
a cathode; and
an organic layer, disposed between the anode and the cathode, the organic layer further comprising a carbazole-containing compound, comprising:

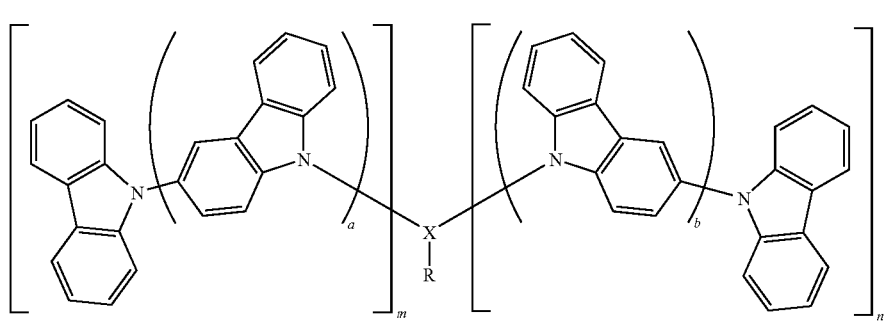

FORMULA I wherein a is 1 to 20;
wherein b is 0 to 20;
wherein m is 0 to 2;
wherein n is 0 to 2;

wherein m+n is at least 1;
wherein X is selected from the group consisting of biphenyl, terphenyl, naphthalene, triphenylene, phenanthrene, fluorene, chrysene, dibenzothiophene, dibenzofuran, benzofuran, benzothiophene, pyrazole, imidazole, triazole, oxazole, thiazole, oxadiazole, oxatriazole, dioxazole, thiadiazole, pyridine, pyridazine, pyrimidine, pyrazine, triazine, indole, benzimidazole, indazole, benzoxazole, benzisoxazole, benzothiazole, quinoline, isoquinoline, cinnoline, quinazoline, quinoxaline, naphthyridine, phthalazine, pteridine, xanthene, phenothiazine, phenoxazine, benzofuropyridine, furodipyridine, benzothienopyridine, and thienodipyridine; and wherein X is substituted by R, where R is selected from the group consisting of hydrogen, alkyl, heteroalkyl, benzene, biphenyl, terphenyl, naphthalene, phenalene, phenanthrene, fluorene, chrysene, dibenzothiophene, dibenzofuran, benzofuran, benzothiophene, pyrazole, imidazole, triazole, oxazole, thiazole, oxadiazole, oxatriazole, dioxazole, thiadiazole, pyridine, pyridazine, pyrimidine, pyrazine, triazine, indole, benzimidazole, indazole, benzoxazole, benzisoxazole, benzothiazole, quinoline, isoquinoline, cinnoline, quinazoline, quinoxaline, naphthyridine, phthalazine, pteridine, xanthene, phenothiazine, phenoxazine, benzofuropyridine, furodipyridine, benzothienopyridine, and thienodipyridine.

34. A method of fabricating an organic light emitting device, comprising:
providing a first electrode;
co-depositing a host and a phosphorescent emitter to form an emissive layer;
wherein the emissive layer comprises an oligocarbazole-containing wherein m is 0 to 2;
wherein n is 0 to 2;
wherein m+n is at least 1;
wherein X is selected from the group consisting of biphenyl, terphenyl, naphthalene, triphenylene, phenanthrene, fluorene, chrysene, dibenzothiophene, dibenzofuran, benzofuran, benzothiophene, pyrazole, imidazole, triazole, oxazole, thiazole, oxadiazole, oxatriazole, dioxazole, thiadiazole, pyridine, pyridazine, pyrimidine, pyrazine, triazine, indole, benzimidazole, indazole, benzoxazole, benzisoxazole, benzothiazole, quinoline, isoquinoline, cinnoline, quinazoline, quinoxaline, naphthyridine, phthalazine, pteridine, xanthene, phenothiazine, phenoxazine, benzofuropyridine, furodipyridine, benzothienopyridine, and thienodipyridine; and wherein X is substituted by R, where R is selected from the group consisting of hydrogen, alkyl, heteroalkyl, benzene, biphenyl, terphenyl, naphthalene, phenalene, phenanthrene, fluorene, chrysene, dibenzothiophene, dibenzofuran, benzofuran, benzothiophene, pyrazole, imidazole, triazole, oxazole, thiazole, oxadiazole, oxatriazole, dioxazole, thiadiazole, pyridine, pyridazine, pyrimidine, pyrazine, triazine, indole, benzimidazole, indazole, benzoxazole, benzisoxazole, benzothiazole, quinoline, isoquinoline, cinnoline, quinazoline, quinoxaline, naphthyridine, phthalazine, pteridine, xanthene, phenothiazine, phenoxazine, benzofuropyridine, furodipyridine, benzothienopyridine, and thienodipyridine; and depositing a second electrode.

35. The method of claim 32, wherein the first electrode is an anode and the second electrode is a cathode.

36. The method of claim 32, wherein an organic layer is deposited after the first electrode and before the emissive layer.

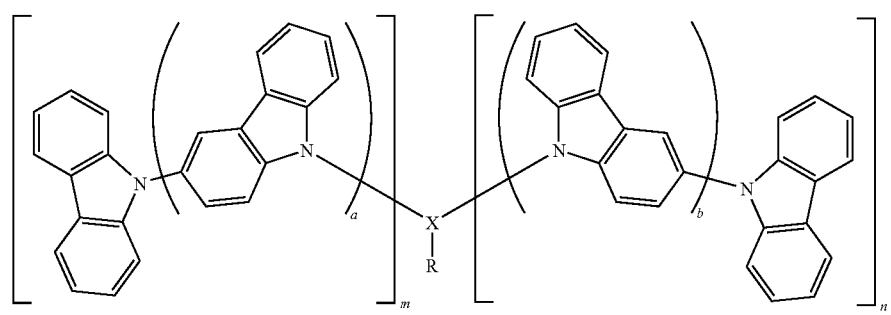

FORMULA I compound, comprising:
wherein a is 1 to 20;
wherein b is 0 to 20;

37. The method of claim 34, wherein the organic layer is a hole transport layer.

* * * * *

UNITED STATES PATENT AND TRADEMARK OFFICE
CERTIFICATE OF CORRECTION

PATENT NO. : 8,221,905 B2  Page 1 of 1
APPLICATION NO. : 12/275894
DATED : July 17, 2012
INVENTOR(S) : Chun Lin et al.

It is certified that error appears in the above-identified patent and that said Letters Patent is hereby corrected as shown below:

Column 171, line 21, change "$SR^{2a}$" to read --$SR^{2a}$,--;
Column 171, line 21, change "$BR^{2a}$, $R^{2b}$," to read --$BR^{2a}R^{2b}$,--.

Signed and Sealed this
Twenty-third Day of October, 2012

David J. Kappos
*Director of the United States Patent and Trademark Office*